(12) United States Patent
Lubin et al.

(10) Patent No.: US 8,796,241 B2
(45) Date of Patent: Aug. 5, 2014

(54) THERAPY OF TUMORS AND INFECTIOUS AGENTS DEFICIENT IN METHYLTHIOADENOSINE PHOSPHORYLASE

(76) Inventors: Adam Lubin, Norwich, VT (US); Martin Lubin, Hanover, NH (US)

( * ) Notice: Subject to any disclaimer, the term of this patent is extended or adjusted under 35 U.S.C. 154(b) by 598 days.

(21) Appl. No.: 12/675,276

(22) PCT Filed: Aug. 15, 2008

(86) PCT No.: PCT/US2008/009779
§ 371 (c)(1),
(2), (4) Date: May 24, 2011

(87) PCT Pub. No.: WO2009/032057
PCT Pub. Date: Mar. 12, 2009

(65) Prior Publication Data
US 2012/0094947 A1    Apr. 19, 2012

Related U.S. Application Data

(60) Provisional application No. 61/034,975, filed on Mar. 8, 2008, provisional application No. 60/968,566, filed on Aug. 29, 2007.

(51) Int. Cl.
  *A61K 31/7076* (2006.01)
  *A61K 31/198* (2006.01)
  *A61K 31/519* (2006.01)
  *A61K 45/06* (2006.01)

(52) U.S. Cl.
  CPC ............ *A61K 31/7076* (2013.01); *A61K 45/06* (2013.01); *A61K 2300/00* (2013.01)
  USPC .............................. 514/46; 435/375; 514/243

(58) Field of Classification Search
  CPC  A61K 31/7076; A61K 45/06; A61K 2300/00
  USPC .................................. 514/46, 243; 435/375
  See application file for complete search history.

(56) References Cited

U.S. PATENT DOCUMENTS

| | | | |
|---|---|---|---|
| 3,472,838 A | 10/1969 | Hanessian | |
| 4,663,313 A | 5/1987 | Bristol et al. | |
| 4,782,173 A | 11/1988 | Burrington et al. | |
| 4,985,409 A | 1/1991 | Yamada et al. | |
| 5,106,837 A | 4/1992 | Carson et al. | |
| 5,180,714 A | 1/1993 | Sufrin et al. | |
| 5,219,839 A | 6/1993 | Bru-Magniez et al. | |
| 5,446,139 A | 8/1995 | Seela et al. | |
| 5,459,255 A | 10/1995 | Cook et al. | |
| 5,484,946 A | 1/1996 | Abood et al. | |
| 5,571,510 A | 11/1996 | Nobori et al. | |
| 5,773,424 A * | 6/1998 | el Kouni et al. ................ | 514/45 |
| 5,889,178 A | 3/1999 | Gregson et al. | |
| 5,942,393 A | 8/1999 | Nobori et al. | |
| 6,210,917 B1 * | 4/2001 | Carson et al. .................... | 435/18 |
| 6,214,571 B1 | 4/2001 | Carrera et al. | |
| 7,157,551 B2 | 1/2007 | Leoni | |
| 2004/0043959 A1 | 3/2004 | Bloom et al. | |
| 2007/0280946 A1 | 12/2007 | Numata et al. | |

FOREIGN PATENT DOCUMENTS

| | | |
|---|---|---|
| WO | WO 99/20791 A1 | 4/1999 |
| WO | WO-99/67634 A1 | 12/1999 |
| WO | WO-03/074083 A1 | 9/2003 |

OTHER PUBLICATIONS

Karikari et al. Homozygous deletions of methylthioadenosine phosphorylase in human biliary tract cancers. Mol Cancer Ther 4:1860-1866, Dec. 2005.*
Chaudhary et al. Toxoplasma gondii Purine Nucleoside Phosphorylase Biochemical Characterization, Inhibitor Profiles, and Comparison with the Plasmodium falciparum Ortholog. J Biol Chem 281:2S652-2S658, 2006.*
Chaudhary et al. Purine Salvage Pathways in the Apicomplexan Parasite Toxoplasma gondii. J Biol Chem 279:31221-31227, 2004.*
Bertino et al., Targeting tumors that lack methylthioadenosine phosphorylase (MTAP) activity: Current strategies. Cancer Biol Ther. Apr. 1, 2011;11(7). [Epub ahead of print].
Lubin et al., A proposed new therapy of tumors deficient in methylthioadenosine phosphorylase (MTAP). Targets and screening approaches: poster presentations. 99th AACR Annual Meeting. Apr. 12-16, 2008. San Diego, CA. Abstract #1531. 2 pages.
Lubin et al., Strategy for selective killing of tumors deficient in methylthioadenosine phosphorylase (MTAP): a progree report. 100th AACR Annual Meeting. Proc Am Assoc Cancer Res; Apr. 18-22, 2009; Denver, CO. Philadelphia (PA): AACR; 2009. Abstract #LB-29.
Collins et al., 2012, Next Generation Sequencing of Prostate Cancer from a Patient Identifies a Deficiency of Methylthioadenosine Phosphorylase, an Exploitable Tumor Target, Mol. Cancer Ther. 11(3):775-784.
[No Author Listed] Biochemistry of the Amino Acids, 2nd Edition. Ed. Meister 1965;2:231-68.
Barker et al., P16 deletion and mutation analysis in human brain tumors. J Neurooncol. Jan. 1997;31(1-2):17-23.
Batova et al., Frequent deletion in the methylthioadenosine phosphorylase gene in T-cell acute lymphoblastic leukemia: strategies for enzyme-targeted therapy. Blood. Oct. 15, 1996;88(8):3083-90.
Batova et al., Use of alanosine as a methylthioadenosine phosphorylase-selective therapy for T-cell acute lymphoblastic leukemia in vitro. Cancer Res. Apr. 1, 1999;59(7):1492-7.
Bello et al., Chromosome aberrations in metastatic ovarian cancer: relationship with abnormalities in primary tumors. Int J Cancer. Jan. 15, 1990;45(1):50-4.

(Continued)

*Primary Examiner* — Brandon Fetterolf
*Assistant Examiner* — Yih-Horng Shiao
(74) *Attorney, Agent, or Firm* — Wolf, Greenfield & Sacks, P.C.

(57) ABSTRACT

Methods for treating diseases in humans and vertebrate animals are provided using competitive antagonists of cellular metabolites combined with a protective agent for protecting host cells from toxic effects of the drugs. Also provided are kits comprising competitive antagonists and suitable protective agents. In addition, screening methods for identifying competitive antagonists, protective agents and potentiating agents, for use according to the methods of the invention, are provided.

10 Claims, 10 Drawing Sheets

(56) References Cited

OTHER PUBLICATIONS

Borsi et al., Rescue after intermediate and high-dose methotrexate: background, rationale, and current practice. Pediatr Hematol Oncol. 1990;7(4):347-63.

Burchenal et al., The effects of the folic acid antagonists and 2,6-diaminopurine on neoplastic disease, with special reference to acute leukemia. Cancer. May 1951;4(3):549-69.

Caldas et al., Frequent somatic mutations and homozygous deletions of the p16 (MTS1) gene in pancreatic adenocarcinoma. Nat Genet. Sep. 1994;8(1):27-32.

Chen et al., Gene deletion chemoselectivity: codeletion of the genes for p16(INK4), methylthioadenosine phosphorylase, and the alpha- and beta-interferons in human pancreatic cell carcinoma lines and its implications for chemotherapy. Cancer Res. Mar. 1, 1996;56(5):1083-90.

Cornell et al., Characterization of recombinant *Eschericha coli* 5'-methylthioadenosine/S-adenosylhomocysteine nucleosidase: analysis of enzymatic activity and substrate specificity. Biochem Biophys Res Commun. Nov. 21, 1996;228(3):724-32.

Cowan et al., Cytogenetic analysis of melanocytes from premalignant nevi and melanomas. J Natl Cancer Inst. Sep. 21, 1988;80(14):1159-64.

Della Ragione e al., *Escherichia coli* S-adenosylhomocysteine/5'-methylthioadenosine nucleosidase. Purification, substrate specificity and mechanism of action. Biochem J. Dec. 1, 1985;232(2):335-41.

Della Ragione et al., 5'-Deoxy-5'-methylthioadenosine phosphorylase and p16INK4 deficiency in multiple tumor cell lines. Oncogene. Mar. 2, 1995;10(5):827-33.

Dreyling et al., Codeletion of CDKN2 and MTAP genes in a subset of non-Hodgkin's lymphoma may be associated with histologic transformation from low-grade to diffuse large-cell lymphoma. Genes Chromosomes Cancer. May 1998;22(1):72-8.

Efferth et al., Methylthioadenosine phosphorylase as target for chemoselective treatment of T-cell acute lymphoblastic leukemic cells. Blood Cells Mol Dis. Jan.-Feb. 2002;28(1):47-56.

Eleff et al., Analysis of "early" thymidine/inosine protection as an adjunct to methotrexate therapy. Cancer Treat Rep. Jul.-Aug. 1985;69(7-8):867-74.

Elion, The purine path to chemotherapy. Nobel lecture in physiology or medicine—1988. Nobel lectures—Physiology or Medicine. Dec. 8, 1988, pp. 447-468.

Fitchen et al., Methylthioadenosine phosphorylase deficiency in human leukemias and solid tumors. Cancer Res. Oct. 1986;46(10):5409-12.

Garcia-Castellano et al., Methylthioadenosine phosphorylase gene deletions are common in osteosarcoma. Clin Cancer Res. Mar. 2002;8(3):782-7.

Harasawa et al., Chemotherapy targeting methylthioadenosine phosphorylase (MTAP) deficiency in adult T cell leukemia (ATL). Leukemia. Sep. 2002;16(9):1799-807.

Hori et al., Methylthioadenosine phosphorylase cDNA transfection alters sensitivity to depletion of purine and methionine in A549 lung cancer cells. Cancer Res. Dec. 15, 1996;56(24):5653-8.

Hori et al., The methylthioadenosine phosphorylase gene is frequently co-deleted with the p16INK4a gene in acute type adult T-cell leukemia. Int J Cancer. Jan. 5, 1998;75(1):51-6.

Illei et al., Detection of homozygous deletion of CDKN2A and methythioadenosine phosphorylase (MTAP) by FISH in 95 cases of pleural mesothelioma. United States and Canadian Academy of Pathology. 91st Annual Meeting. Feb. 23-Mar. 1, 2002.

Jagasia et al., Chromosome 9 related aberrations and deletions of the CDKN2 and MTS2 putative tumor suppressor genes in human chondrosarcomas. Cancer Lett. Jul. 19, 1996;105(1):91-103.

Jagasia et al., Partial deletions of the CDKN2 and MTS2 putative tumor suppressor genes in amyxoid chondrosarcoma. Cancer Lett. Jul. 19, 1996;105(1):77-90.

Kadariya et al., Deletion of dinucleotide repeat (Delta 14 allele) in the methylthioadenosine phosphorylase (MTAP) promoter and the allelotype of MTAP promoter in the Japanese population. Jpn J Cancer Res. Apr. 2002;93(4):369-73.

Kamatani et al., Abnormal regulation of methylthioadenosine and polyamine metabolism in methylthioadenosine phosphorylase-deficient human leukemic cell lines. Cancer Res. Nov. 1980;40(11):4178-82.

Kamatani et al., Selective killing of human malignant cell lines deficient in methylthioadenosine phosphorylase, a purine metabolic enzyme. Proc Natl Acad Sci U S A. Feb. 1981;78(2):1219-23.

Kikugawa et al., Platelet aggregation inhibitors. 2. Inhibition of platelet aggregation by 5'-, 2-, 6-, and 8-substituted adenosines. J Med Chem. Apr. 1972;15(4):387-90.

Kokkinakis et al., Effect of long-term depletion of plasma methionine on the growth and survival of human brain tumor xenografts in athymic mice. Nutr Cancer. 1997;29(3):195-204.

Kung et al., Design, synthesis, and biological evaluation of novel human 5'-deoxy-5'-methylthioadenosine phosphorylase (MTAP) substrates. Bioorg Med Chem Lett. Jun. 2, 2005;15(11):2829-33.

Li et al., Status of methylthioadenosine phosphorylase and its impact on cellular response to L-Alanosine and methylmercaptopurine riboside in human soft tissue sarcoma cells. Oncology Res. 2004;14:373-9.

Merlo et al., Homozygous deletion on chromosome 9p and loss of heterozygosity on 9q, 6p, and 6q in primary human small cell lung cancer. Cancer Res. May 1, 1994;54(9):2322-6.

M'Soka et al., Detection of methylthioadenosine phosphorylase (MTAP) and p16 gene deletion in T cell acute lymphoblastic leukemia by real-time quantitative PCR assay. Leukemia. May 2000;14(5):935-40.

Nobori et al., Absence of methylthioadenosine phosphorylase in human gliomas. Cancer Res. Jun. 15, 1991;51(12):3193-7.

Nobori et al., Methylthioadenosine phosphorylase deficiency in human non-small cell lung cancers. Cancer Res. Mar. 1, 1993;53(5):1098-101.

Olopade et al., Homozygous loss of the interferon genes defines the critical region on 9p that is deleted in lung cancers. Cancer Res. May 15, 1993;53(10 Suppl):2410-5.

Riscoe et al., Methionine recycling as a target for antiprotozoal drug development. Parasitol Today. Oct. 1989;5(10):330-3.

Robins et al., Nucleic acid related compounds. 66. Improved syntheses of 5'-chloro-5'-deoxy- and 5'-S-aryl(or alkyl)-5'-thionucleosides. Can J Chem. Sep. 1991;69(9):1468-74.

Robins et al., Nucleic acid related compounds. 80. Synthesis of 5'-S-(Alkyl and aryl)-5'- fluoro-5'-thioadenosines with Xenon Difluoride or (Diethylamido)sulfur Trifluoride, hydrolysis in aqueous buffer, and inhibition of S-Adenosyl-L-homocysteine hydrolase by derived "Adenosine 5'-Aldehyde" species. J Org Chem. 1994;59(3):544-555.

Schmid et al., Homozygous deletions of methylthioadenosine phosphorylase (MTAP) are more frequent than p16INK4A (CDKN2) homozygous deletions in primary non-small cell lung cancers (NSCLC). Oncogene. Nov. 19, 1998;17(20):2669-75.

Schwartz et al., A phase I trial of a modified, dose intensive FAMTX regimen (high dose 5-fluorouracil+doxorubicin+high dose methotrexate+leucovorin) with oral uridine rescue. Cancer. Nov. 1, 1996;78(9):1988-95.

Sharma et al., Polyamine metabolism in some helminth parasites. Exp Parasitol. Jan. 1991;72(1):15-23.

Smaaland et al., Methylthioadenosine phosphorylase in human breast cancer. Breast Cancer Res Treat. 1987;9(1):53-9.

Stadler et al., The 9p21 region in bladder cancer cell lines: large homozygous deletion inactivate the CDKN2, CDKN2B and MTAP genes. Urol Res. 1996;24(4):239-44.

Stadler et al., Alterations of the 9p21 and 9q33 chromosomal bands in clinical bladder cancer specimens by fluorescence in situ hybridization. Clin Cancer Res. Jun. 2001:7(6):1676-82.

Sufrin et al., Synthesis and antiproliferative effects of novel 5'-fluorinated analogues of 5'- deoxy-5'-(methylthio)adenosine. J Med Chem. May 1989;32(5):997-1001.

Tekwani et al., Polyamine uptake by a rodent filariid, Acanthocheilonema viteae (Nematoda: Filarioidea). Int J Biochem Cell Biol. Aug. 1995;27(8):851-5.

Tisdale, Methionine synthesis from 5'-methylthioadenosine by tumour cells. Biochem Pharmacol. Oct. 1, 1983;32(19):2915-20.

(56) References Cited

OTHER PUBLICATIONS

Toohey, Methylthio group cleavage from methylthioadenosine. Description of an enzyme and its relationship to the methylthio requirement of certain cells in culture. Biochem Biophys Res Commun. Oct. 24, 1977;78(4):1273-80.

Van Der Riet et al., Frequent loss of chromosome 9p21-22 early in head and neck cancer progression. Cancer Res. Mar. 1, 1994;54(5):1156-8.

Verdorfer et al., Cytogenetic characterization of 22 human renal cell tumors in relation to a histopathological classification. Cancer Genet Cytogenet. May 1999;111(1):61-70.

Wong et al., MTAP gene deletion in endometrial cancer. Gynecol Obstet Invest. 1998;45(4):272-6.

Zhang et al., Codeletion of the genes for p16INK4, methylthioadenosine phosphorylase, interferon-alpha1, interferon-beta1, and other 9p21 markers in human malignant cell lines. Cancer Genet Cytogenet: Jan. 1996;86(1):22-8.

Lubin et al., Selective killing of tumors deficient in methylthioadenosine phosphorylase: a novel strategy. PLoS One. May 29, 2009;4(5):e5735.

Bertino et al., Regression of a human T-cell leukemia lacking the methylthioadenosine phosphorylase (MTAP) gene without toxicity of 6-thioguanine (6TG) by pretreatment with methylthioadenosine (MTA). Poster and abstract. Presented at the AACR 101st Annual Meeting on Apr. 19, 2010. 2 pages.

Sartorelli et al., Some inhibitory properties of 6-n-hydroxylaminopurine: an analog of adenine and hypoxanthine. Biochem Pharmacol. Mar. 1964;13:507-15.

Basu et al., A transition state analogue of 5'-methylthioadenosine phosphorylase induces apoptosis in head and neck cancers. J Biol Chem. Jul. 20, 2007;282(29):21477-86. Epub Jun. 4, 2007. Supplemental materials included.

Ikeguchi et al., Aminopropyltransferases: function, structure and genetics. J Biochem. Jan. 2006;139(1):1-9.

Wu et al., Crystal structure of human spermine synthase: implications of substrate binding and catalytic mechanism. J Biol Chem. Jun. 6, 2008;283(23):16135-46. Epub Mar. 26, 2008.

\* cited by examiner

Schematic depiction of the MTAP-pathway in mammalian cells, and its interconnections with the pathways of polyamine biosynthesis, the activated methyl cycle, and purine metabolism Effects of four days treatment with DAP(100μM) and MTA(25μM) on MCF7 and HF cells grown in coculture Start of Coculture Four Days with DAP + MTA Four days DAP + MTA; then culture split 1:5 into drug-free medium and fixed two days later Four days DAP + MTA; then culture split 1:5 into drug-free medium and fixed five days later

Effects of three days treatment with DAP(200µM) and MTA(50µM) on MCF7 and HF cells grown in coculture

Start of Coculture

Three Days without Drugs

Three Days with DAP

Three Days with DAP + MTA

Protection of Murine Hematopoietic Cell Progenitors from MeP Toxicity by 5'-dAdo and Adenine

8 Days, NO DRUGS

8 Days, 5μM MeP

8 Days, 5μM MeP + 15μM Ade

8 Days, 5μM MeP + 15μM 5'-dAdo

8 Days, 15μM MeP + 15μM Ade

8 Days, 5μM MeP + 15μM 5'-dAdo

THERAPY OF TUMORS AND INFECTIOUS AGENTS DEFICIENT IN METHYLTHIOADENOSINE PHOSPHORYLASE

RELATED APPLICATIONS

This application claims priority under 35 USC §119 to U.S. Provisional Application No. 60/968,566, filed Aug. 29, 2007, and U.S. Provisional Application No. 61/034,975 filed Mar. 8, 2008, the entire contents of which are hereby incorporated by reference.

FIELD OF THE INVENTION

The invention relates to the treatment of diseases such as infectious disease and cancer. The invention relates in part to the use of chemotherapeutic agents effective against such diseases in combination with agents for reducing the host toxicity of such chemotherapeutic agents.

BACKGROUND OF THE INVENTION

Antimetabolites can be used clinically for the treatment of diseases, such as, for example, bacterial and viral, as well as parasitical infections and in chemotherapies directed at tumors. Although antimetabolites, such as folate analogs and purine and pyrimidine analogs, have proven useful in the chemotherapy of cancer and in some cases, viral and other diseases, these therapeutic agents have significant side effects. As is the case with most chemotherapies directed at, for example, tumors, antimetabolites lack specificity for only tumor cells, and generally inhibit and kill, indiscriminately, all dividing cells, whether neoplastic or normal. Particularly vulnerable to the toxic effects of antimetabolites are the rapidly dividing progenitor cells of the hematopoietic system and of the gastrointestinal and oral mucosal epithelium. These serious side effects frequently compromise the health of the patient, and they limit the usable dosages of these agents, as a consequence of which tumor cells often evade destruction and develop drug resistance.

In addition to folate and purine and pyrimidine antimetabolites, many analogs of amino acids with good activity against various target cells, including tumors, viruses, bacteria, and protozoa (A. Meister, ed., *Biochemistry of the Amino Acids*, 2nd ed., Volume 1, 1965, 231-268), have been synthesized and investigated. However, amino acid analogs, like the aforementioned purine and pyrimidine and folate analogs, are not specific in their action and inhibit the proliferation of both normal and target cells, again leading to serious side effects, which reduce their utility and effectiveness.

Some proposals for ameliorating the toxic side effects of antimetabolites have been made and have been attempted in clinical studies. (J. D. Borsi et al, Rescue after Intermediate and High-dose Methotrexate: Background, Rationale, and Current Practice, Pediatric Hematology and Oncology, 7:347-363, 1990; M. Eleff et al. Analysis of "early" thymidine/inosine protection as an adjunct to methotrexate therapy, Cancer Research Rep., 69:867-874, 1985; G. K. Schwartz et al, A phase I trial of a modified, dose intensive FAMTX regimen (high dose 5-fluorouracil+doxorubicin+high dose methotrexate+leucovorin) with oral uridine rescue, Cancer, 78(9):1988-95, 1996). Because of many difficulties, none of these methods has been adopted into standard clinical practice, with the exception of "Leucovorin rescue."

SUMMARY OF THE INVENTION

In one aspect the invention is a method for treating a subject having a disease by administering to the subject a competitive antagonist of a cell metabolite in an amount effective to treat the disease; and administering to the subject a protective agent in an amount effective to increase the level of the cell metabolite in a population of host cells of the subject, thereby reducing the toxicity of the competitive antagonist to the subject. The protective agent may be administered to the subject prior to the competitive antagonist or vice versa. In other embodiments the two agents may be administered together.

In other aspects a method for the selective protection of a host cell exposed to a competitive antagonist of a cell metabolite is provided. The method involves contacting the host cell with a protective agent in an amount effective to increase the level of the cell metabolite in the host cell thereby reducing the toxicity of the competitive antagonist to the host cell. In some embodiments a subject having the host cell is treated with the competitive antagonist to inhibit a target cell.

In some embodiments the cell metabolite is a product of the MTAP-pathway. The protective agent in some embodiments may be a MTAP substrate. In other embodiments the protective agent is a MTA compound, such as, for instance, 5'-deoxyadenosine, 2',5'-dideoxyadenosine, 2'-deoxy-5'-deoxy-5'-methylthioadenosine, 5'-deoxy-5'-chloroadenosine, 5'-deoxy-5'-fluoroadenosine, 5'-deoxy-5'-methyloxyadenosine, 5'-deoxy-5'-methylselenoadenosine, 5'-deoxy-5'-ethylthioadenosine, 9-β-D-erythrofuranosyladenine, 5'-deoxy-5'-methylthio-2-methyladenosine, or 5'-deoxy-5'-methylthio-1-deazaadenosine. In other embodiments the protective agent is a methionine salvage pathway substrate.

In other embodiments the competitive antagonist is a structural analog of the cell metabolite such as an analog of adenine. Analogs of adenine include for instance 2,6-diaminopurine, 6-methylpurine, 2-fluoroadenine, 8-azaadenine, 2-azaadenine, 4-aminopyrazolo[3,4-d]pyrimidine, 8-aza-2,6-diaminopurine, 1-methyladenine, 7-deaza-8-azaadenine, 6-methylaminopurine, 6-N-hydroxylaminopurine, 6-hydrazinopurine, 7-methyladenine, 8-methyladenine, 8-hydroxyadenine, and the 2-methyl-, 2-chloro-, 2-iodo-, 2-hydroxy, 2-methylthio, 2-mercapto-derivatives of adenine. The competitive antagonist of adenine in some embodiments is a substrate for a phosphoribosyltransferase which utilizes 5-phosphoribosyl-1-pyrophosphate (PRPP) as the phosphoribosyl donor. The phosphoribosyltransferase may be APRT, HGPRT, OPRT, QPRT, NAPRT, or NAMPRT. In other embodiments the competitive antagonist is an analog of methionine, such as ethionine, selenomethionine, methoxinine, selenoethionine, α-methylmethionine, and trifluoromethionine.

The subject has a disease, such as for instance, cancer or an infectious disease. The methods of the invention are also useful in the transplant setting, for instance, to protect the recipient from receiving infected tissues.

A method of treating a subject having a MTAP positive target cell by contacting the MTAP positive target cell with an agent that inhibits the production or activity of MTAP in the cells; administering to the subject a competitive antagonist of adenine or methionine in an amount sufficient to inhibit the MTAP positive target cell; and administering to the subject a protective agent that increases the production of adenine or methionine by the MTAP-pathway in a host cell in the subject, thereby decreasing the toxic mechanism of action on the subject is provided according to other aspects of the invention. In one embodiment the MTAP positive target cell is a tumor cell.

In another aspect the invention is a composition of a sterile protective agent capable of increasing a level of a cell metabolite in a host cell, formulated in a carrier for delivery to a cancer patient in an effective amount for reducing the toxicity of a competitive antagonist of the cell metabolite in the subject.

A kit is provided according to other aspects of the invention. The kit includes a container housing a protective agent capable of increasing a level of a cell metabolite in a host cell in a sterile formulation and instructions for administering the protective agent to a subject in an effective amount for reducing the toxicity of a competitive antagonist of a cell metabolite in the subject.

In some embodiments the container houses a single dose for administration to a human subject. The human subject may have cancer such as a MTAP negative cancer. In other embodiments the subject has an infectious disease.

In other embodiments the kit includes a container housing a competitive antagonist of a cell metabolite.

In some embodiments the cell metabolite is a product of the MTAP-pathway. The protective agent in some embodiments may be a MTAP substrate. In other embodiments the protective agent is a MTA compound, such as, for instance, 5'-deoxyadenosine, 2',5'-dideoxyadenosine, 2'-deoxy-5'-deoxy-5'-methylthioadenosine, 5'-deoxy-5'-chloroadenosine, 5'-deoxy-5'-fluoroadenosine, 5'-deoxy-5'-methyloxyadenosine, 5'-deoxy-5'-methylselenoadenosine, 5'-deoxy-5'-ethylthioadenosine, 9-β-D-erythrofuranosyladenine, 5'-deoxy-5'-methylthio-2-methyladenosine, or 5'-deoxy-5'-methylthio-1-deazaadenosine. In other embodiments the protective agent is a methionine salvage pathway substrate.

In other embodiments the competitive antagonist is a structural analog of the cell metabolite such as an analog of adenine. Analogs of adenine include for instance 2,6-diaminopurine, 6-methylpurine, 2-fluoroadenine, 8-azaadenine, 2-azaadenine, 4-aminopyrazolo[3,4-d]pyrimidine, 8-aza-2,6-diaminopurine, 1-methyladenine, 7-deaza-8-azaadenine, 6-methylaminopurine, 6-N-hydroxylaminopurine, 6-hydrazinopurine, 7-methyladenine, 8-methyladenine, 8-hydroxyadenine, and the 2-methyl-, 2-chloro-, 2-iodo-, 2-hydroxy, 2-methylthio, 2-mercapto-derivatives of adenine. The competitive antagonist of adenine in some embodiments is a substrate for a phosphoribosyltransferase which utilizes 5-phosphoribosyl-1-pyrophosphate (PRPP) as the phosphoribosyl donor. The phosphoribosyltransferase may be APRT, HGPRT, OPRT, QPRT, NAPRT, or NAMPRT. In other embodiments the competitive antagonist is an analog of methionine, such as ethionine, selenomethionine, methoxinine, selenoethionine, α-methylmethionine, and trifluoromethionine.

The foregoing features, as well as other features, of the invention will be more readily understood by reference to the following detailed description, taken with reference to the accompanying drawings.

DETAILED DESCRIPTION OF THE INVENTION

Figure 1:
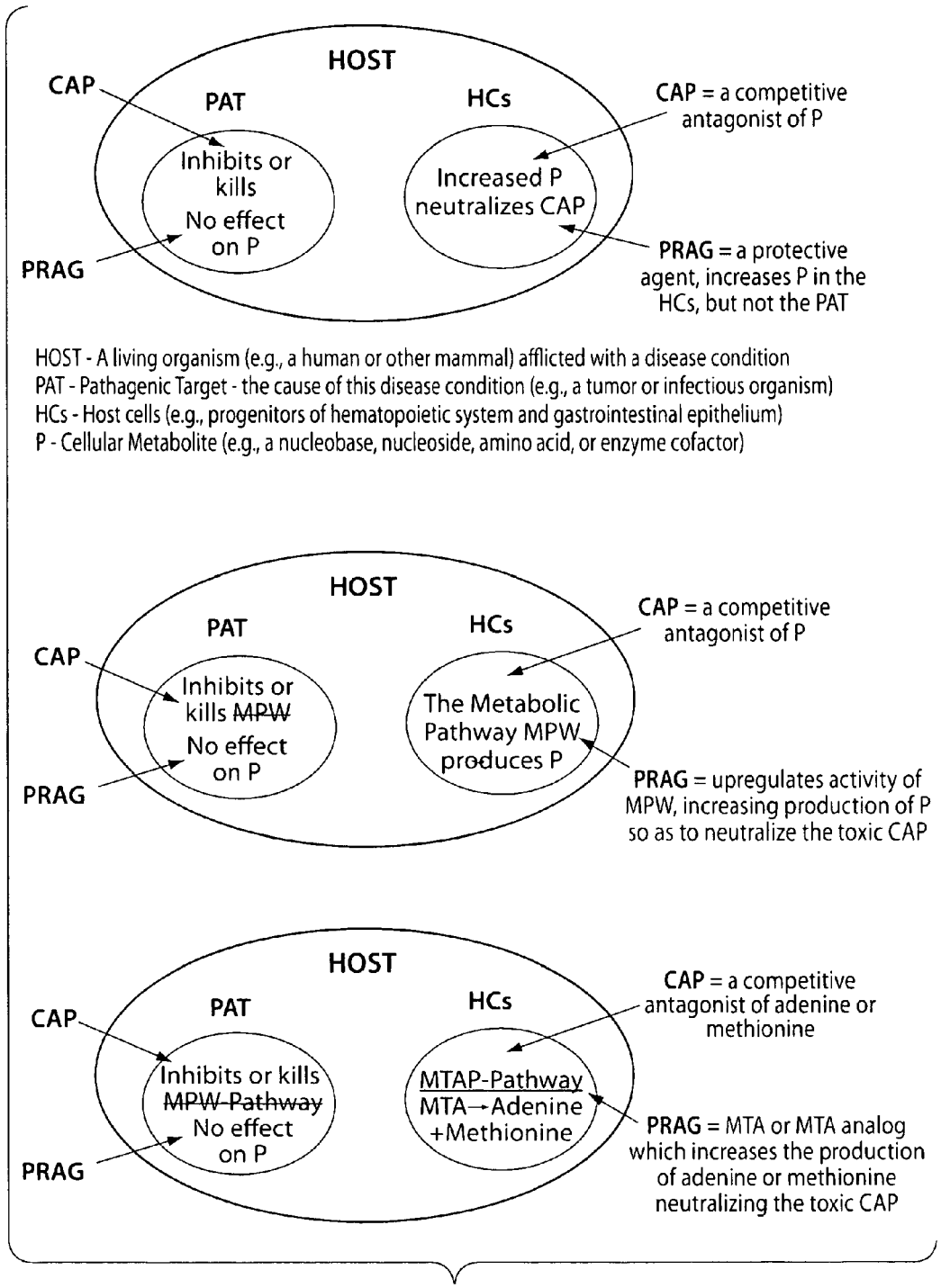
FIG. 1 is a schematic depiction of some embodiments described herein relating to selective therapeutic methods.

The present invention in certain embodiments provides methods for treating a disease in a subject, with low, or non-existent, toxicity to the subject. Such a therapy with minimal host toxicity is commonly referred to as a "selective" therapy. The methods described herein are useful, for instance, in the treatment of a variety of diseases, including those caused by aberrant target cells, such as tumor cells, and infectious organisms such as viruses, bacteria, protozoa, rickettsiae, chlamydiae, mycoplasmas, fungi, and helminths.

The present invention provides a selective therapeutic method involving treatment with a drug which is a competitive antagonist of a cellular metabolite, in a dose sufficient to inhibit or kill a target cell, combined with a protective agent to increase the level of the cellular metabolite in cells which are important for the health of the subject (host cells), to a degree sufficient to protect these cells (and hence the subject) from the toxic effects of the drug.

Thus, the invention enables the use of toxic drugs for therapeutic purposes while protecting the host cells from toxic damage due to the drugs. The host cells which are to be protected from the toxic effects of competitive antagonist may be rapidly dividing progenitors of some of the subject's critical tissues, particularly the progenitors of the hematopoietic system and the epithelium of the gastrointestinal and oral mucosa. In certain embodiments host cells may also include other rapidly dividing cell populations, such as those of the epidermis, including hair follicles, and the testis. In younger, growing subjects in need of treatment, the host cell population which may be protected by a selective therapeutic method described herein may include stem cells and other progenitors of most, or all, of the major organ systems and tissues.

A "host" or "subject" shall mean a human or vertebrate animal or mammal including but not limited to a dog, cat, horse, cow, pig, sheep, goat, mouse, rat, rabbit, guinea pig, hamster, gerbil, turkey, chicken, and non-human primate, e.g., monkey. In some embodiments, methods described herein can also be useful in veterinary medicine and in biomedical research. Organs, tissues, and cells derived or originating from these subjects, or other mammals, may also be treated, in some embodiments, according to methods described herein, for either therapeutic or research purposes. In some embodiments, methods described herein may be useful in the prophylaxis of disease in humans and other mammals.

The methods are performed in some instances to inhibit target cells. The methods of the invention may be utilized in the treatment of disease caused by aberrant populations of target cells while minimizing the effects to host cells. The particular disease-causing entities to be inhibited or eradicated as described herein, whether tumor or other aberrant host cells, or infectious organisms, will be referred to, generically, as the target cell.

A "target cell" as used herein is any cell, virus, microorganism or other organism, endogenous or exogenous (i.e., intrinsic or foreign) to the subject, that causes an adverse effect to the subject. A target cell might be, for example, a cancer or tumor cell, a non-tumor aberrant cell, or an infectious or parasitic organism, such as, a virus, a bacterium, an insect, a protozoan, a *rickettsia*, a *chlamydia*, an arachnid, a helminth, a nematode, an annelid, a mollusk, a mycoplasma, or a fungus, but is not so limited. An "adverse condition" shall mean a disorder or disease, for example, a cancer, a tumor, an infectious disease, or an allergic reaction.

In some embodiments, the target cell is a MTAP negative cell. A MTAP negative cell is one in which the enzyme MTAP is absent from the target cell, or has substantially lowered activity and/or expression therein, or can be specifically downmodulated in the target cell. When the treatment regimen is performed on a MTAP negative cell, such treatment regimen may result in protection of the subject from the toxicity of the adenine or methionine antagonist without compromising its inhibitory or lethal action against the target cell.

The therapies of the invention are based on the manipulation of a cellular metabolite. The methods described herein involve treating with a drug which is a competitive antagonist of a cellular metabolite, in a dose sufficient to inhibit or kill the target cell, combined with a protective agent to increase the level of cellular metabolite in cells which are critical to the health of the subject, to a degree sufficient to protect these cells (and hence the subject) from the toxic effects of the drug. The therapeutic effects are accomplished by increasing the level of the cellular metabolite in the host cells while avoiding a significant increase in the level of the cellular metabolite available to the target cell. Thus, the target cell may be inhibited or killed by the competitive antagonist, while the treated subject may be protected from the toxic effects of this drug by maintaining a reasonable level of the cellular metabolite.

In some embodiments, the cellular metabolite may be a metabolite involved in nucleic acid synthesis, protein synthesis, or some other metabolic function essential to growth and proliferation of cells or viruses; for example, the cellular metabolite may be a nucleobase, a nucleoside, an amino acid, or an enzyme cofactor. Metabolites include for instance adenine and methionine. A "cell metabolite," as used herein, shall mean a substance or compound in some way involved in a cellular metabolic pathway, such as, for example, but not limited to, enzyme cofactors, vitamins, amino acids, nucleobases and nucleosides, purines and pyrimidines. As used herein, "cell metabolite" and "cellular metabolite" are used interchangeably.

Nucleobases, nucleosides, amino acids, and enzyme cofactors are natural metabolites of small size. For many of these metabolites there exist efficient systemic transport and distribution mechanisms in mammals and good uptake mechanisms into target cells. Many analogs of these metabolites, employed as therapeutic agents in some embodiments, may have favorable pharmacological characteristics that may include, but are not limited to, depending on the agent: high in vivo stability and long half-life; good systemic bioavailability (including effective penetration of pharmacological sanctuaries, such as the central nervous system and testis); and good uptake into target cells. In certain embodiments, metabolite analogs may be formulated for oral administration, greatly simplifying their clinical use. In certain embodiments, protective agents may be substrates of metabolic pathways, and may be small molecules and natural metabolites (or analogs of natural metabolites). Such protective agents may have good in vivo stability and prolonged half life, good systemic biodistribution, and good uptake into mammalian cells, pharmacological characteristics significantly enhancing their efficacy, and facilitating their use.

The therapeutic agents used in the methods of the invention are referred to as competitive antagonists. A "competitive antagonist," as defined herein, shall mean a substance or compound that competes reversibly or irreversibly, with the cell metabolite, for reaction with another cellular molecule. The other cellular molecule is one that reacts with the cellular metabolite and the competitive antagonist, such as a cellular enzyme or a non-enzyme molecule, such as an enzyme cofactor. The toxic action of the competitive antagonist in host cells is mediated, at least in part, by this reaction. As a competitive reactant with the cell metabolite, the toxic effects of the competitive antagonist in host cells will be blocked by increased levels of the cell metabolite achieved by the protective agent, using the methods of the invention. In certain embodiments, the toxic effects of the competitive antagonist in the target cell is not blocked by increased levels of the cell metabolite, because the toxic effects in the target cell are mediated by a different mechanism than they are in the host cells (such may be the case, for example, when the competitive antagonist is a substrate for different enzymes in the target and host cells). In other embodiments, the toxic effects of the competitive antagonist in the target cell is mediated by the same mechanism as in the host cell. In these latter embodiments, however, the target cell does not have the ability to produce significantly increased levels of the cell metabolite using the protective agent; hence the toxic effects of the competitive antagonist in the target cell are not blocked by exposure to the protective agent.

As used herein, the word "competitive" may sometimes be omitted, or its location may be moved, when denoting a competitive antagonist of a cell metabolite. For instance, as used herein, "an adenine antagonist" and "an adenine competitive antagonist" both mean the same as "a competitive antagonist of adenine". Also, as used herein, when denoting a competitive antagonist of a cell metabolite, the words "of a cell metabolite" may sometimes be omitted, for the sake of brevity.

In some embodiments the competitive antagonist is a structural analog of the cell metabolite whose toxic effects are mediated at least in part through its action as a competitive substrate or inhibitor for at least one enzyme that acts on the cell metabolite. The toxic effects of the competitive antagonist in the host cells will be competitively blocked, according to the methods of the invention, by increased levels of the cell metabolite.

In some embodiments the cellular metabolite and competitive antagonist may be competitive ligands for some cellular enzyme; in other embodiments the cellular metabolite and competitive antagonist might compete for reaction with, or binding to, a non-enzyme molecule, for example, another cellular metabolite, a transport molecule, a receptor, or a signaling or regulatory molecule or site. It should be appreciated that the toxic mode, or modes, of action of the competitive antagonist in the target cell may be the same as that in the host cells, or may not be the same, and the toxicity in the target cell may in fact be exerted through interaction with other enzymes or molecules in the target cell, distinct from those in the host cells. It will also be appreciated that there need not be any competitive antagonism whatsoever between the competitive antagonist and the cellular metabolite in the target cell, but only in the host cells; the competitive antagonist may inhibit the target cell by any mechanism. In some embodiments a therapeutic method described herein encompasses the inhibition of a target cell by a competitive antagonist of a cellular metabolite, wherein the toxic effects of the competitive antagonist in the host cells is mediated, at least in part, through the reaction of the competitive antagonist with a molecule that the cellular metabolite also reacts with, and wherein this reaction of the competitive antagonist with a molecule in the host cells, can be competitively blocked by increased levels of the cellular metabolite in the host cells.

In some instances the competitive antagonist is a competitive antagonist of adenine or methionine. Such antagonists are useful in treating, according to the methods described herein, various malignant, nonmalignant, and infectious diseases of humans. They are especially useful in the therapy of tumors which are deficient in the enzyme 5'-deoxy-5'-methylthioadenosine phosphorylase (EC 2.4.2.28; henceforth referred to simply as methylthioadenosine phosphorylase or MTAP). MTAP catalyzes the phosphorolysis of the thionucleoside 5'-deoxy-5'-methylthioadenosine (MTA) to adenine and 5-methylthioribose-1-phosphate (MTR-1-P). MTA, the enzyme's substrate, is produced from S-adenosyl-L-methionine (SAM) during the synthesis of the polyamines spermidine and spermine. Both of the products of the cleavage of MTA by MTAP are reused: adenine is returned to the adenine nucleotide pool via the enzyme adenine phosphoribosyltransferase (APRT, EC 2.4.2.7) and MTR-1-P is metabolized by a series of additional steps to methionine and formate. Thus the enzyme MTAP plays a crucial role in initiating the recycling of the adenine and methylthio moieties of SAM back to the metabolites from which SAM is formed (i.e., ATP and methionine). The entire metabolic pathway which leads from MTA to the formation of adenine, methionine, and formate is referred to herein as the MTAP-pathway, as its initiating step is the cleavage of MTA by the enzyme MTAP (see FIG. 2). The portion of the MTAP-pathway that leads from MTR-1-P to methionine and formate is sometimes referred to, in the art, as "the methionine salvage pathway" and will be referred to as such, herein.

Although it appears that all normal, proliferating mammalian cells contain active MTAP, many malignant cells have been found to lack MTAP activity. Such malignant cells do not metabolize MTA but instead simply excrete it (N. Kamatani et al, Cancer Research, 40:4178-4182, 1980). Two distinct approaches to the selective therapy of such MTAP-deficient tumors have previously been suggested—inhibition of de novo purine biosynthesis and methionine starvation. (N. Kamatani, W. A. Nelson-Rees, D. A. Carson, Selective killing of human malignant cell lines deficient in methylthioadenosine phosphorylase, a purine metabolic enzyme, Proc. Natl. Acad. Sci. USA, 78:1219-1223, 1981) and (M. J. Tisdale, Methionine Synthesis from 5'-Methylthioadenosine by Tumour Cells, Biochemical Pharmacology, 32(19):2915-2920, 1983)—leading to a number of follow-up studies (see e.g., T. Nobori et al, Cancer Research, 53(5):1098-1101, 1993; T. Nobori et al, U.S. Pat. No. 5,571,510; A. Batova et al, Blood, 88(8):3083-3090, 1996; H. Hori et al, Cancer Research, 56:5653-5658, 1996; A. Batova et al, Cancer Research, 59(7):1492-1497, 1999; C. Carrera et al, U.S. Pat. No. 6,214,571; J. M. Garcia-Castellano et al, Clinical Cancer Research 8(3):782-787, 2002; T. Efferth et al, Blood, Cells, Molecules, and Diseases 28(1):47-56, 2002); U.S. Publ. Pat. Appl. No. 2004/0043959).

Such methods of selective treatment of MTAP-negative tumors, methionine starvation and inhibition of de novo purine nucleotide biosynthesis, present major difficulties in effective implementation. A basic problem with the methionine deprivation approach is that methionine starvation of tumors requires significant, prolonged reductions in plasma methionine which can be very difficult to achieve in practice (D. M. Kokkinakis et al, Nutrition and Cancer, 29(30):195-204, 1997) and many tumor cells simply arrest, rather than die. Blockade of de novo purine nucleotide biosynthesis can be circumvented by alternative synthesis pathways. Moreover, both methionine starvation and purine nucleotide starvation of tumors have been found to have relatively low thresholds for reversal by supplied methionine or purines. Hence either of these therapeutic approaches might be seriously compromised by metabolic cooperation in which normal, MTAP-positive cells provide methionine or purines to the MTAP-negative tumor cells, especially when an exogenous methionine or purine source such as MTA is administered (T. Nobori et al, Cancer Research, 51(12):3193-3197, 1991; Zhi-Hao Chen et al, Cancer Research, 56:1083-1090, 1996).

The invention, in certain embodiments, provides methods for treating human tumors which are deficient in the enzyme MTAP. In these embodiments, a competitive antagonist of adenine or methionine, which is known to inhibit or kill the target cell in the afflicted subject, may be administered. At substantially the same time, or an earlier or later time, a protective agent such as methylthioadenosine (MTA), or an analog of MTA, is administered to the subject in order to generate adenine or methionine in host cells of the subject, via the MTAP-pathway, in an amount sufficient to neutralize the toxicity of the adenine or methionine antagonist to these host cells.

Figure 3A:
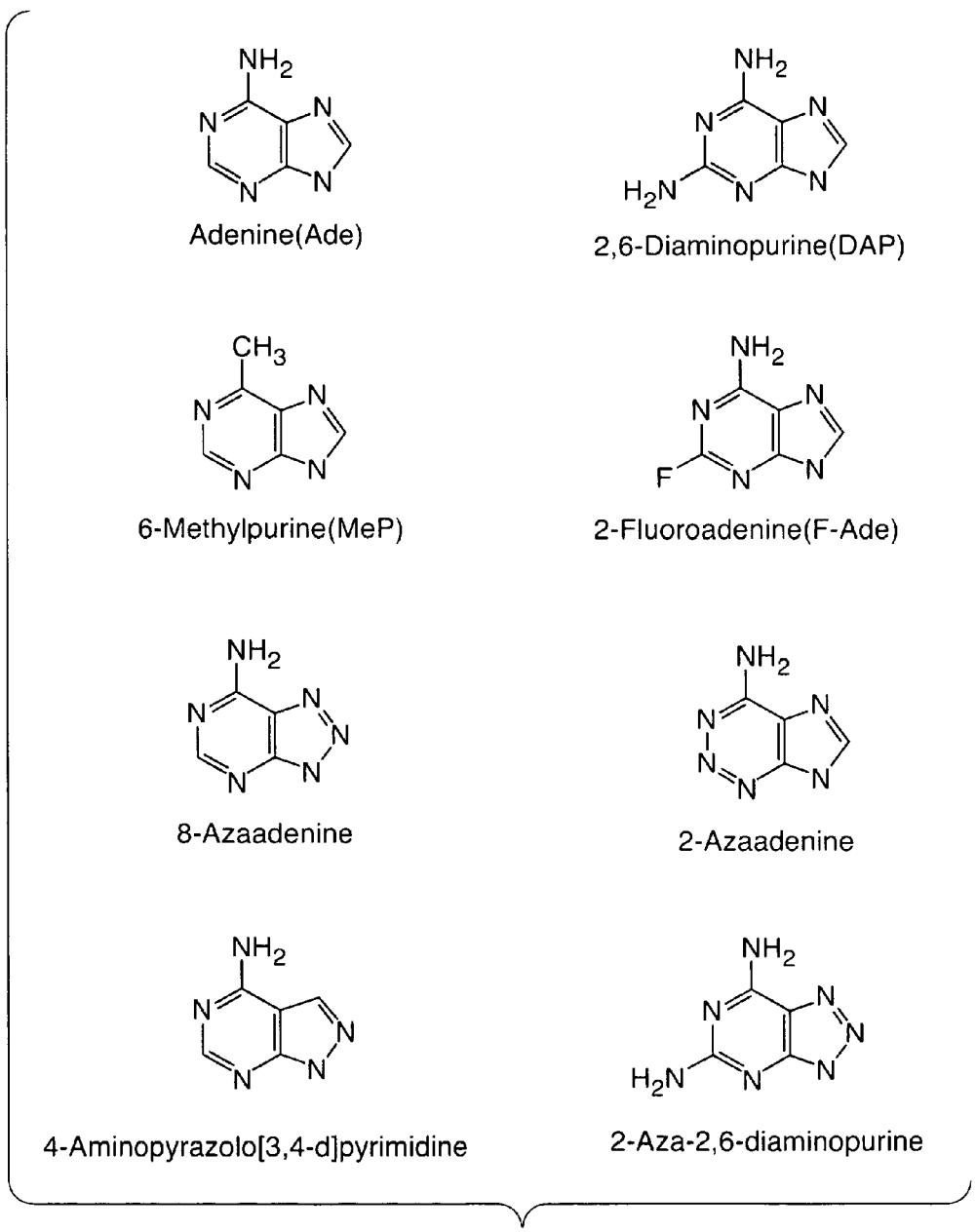
FIGS. 3a, 3b, and 3c depict the structure of adenine and some adenine analogs useful in certain embodiments of the invention.
Figure 3B:
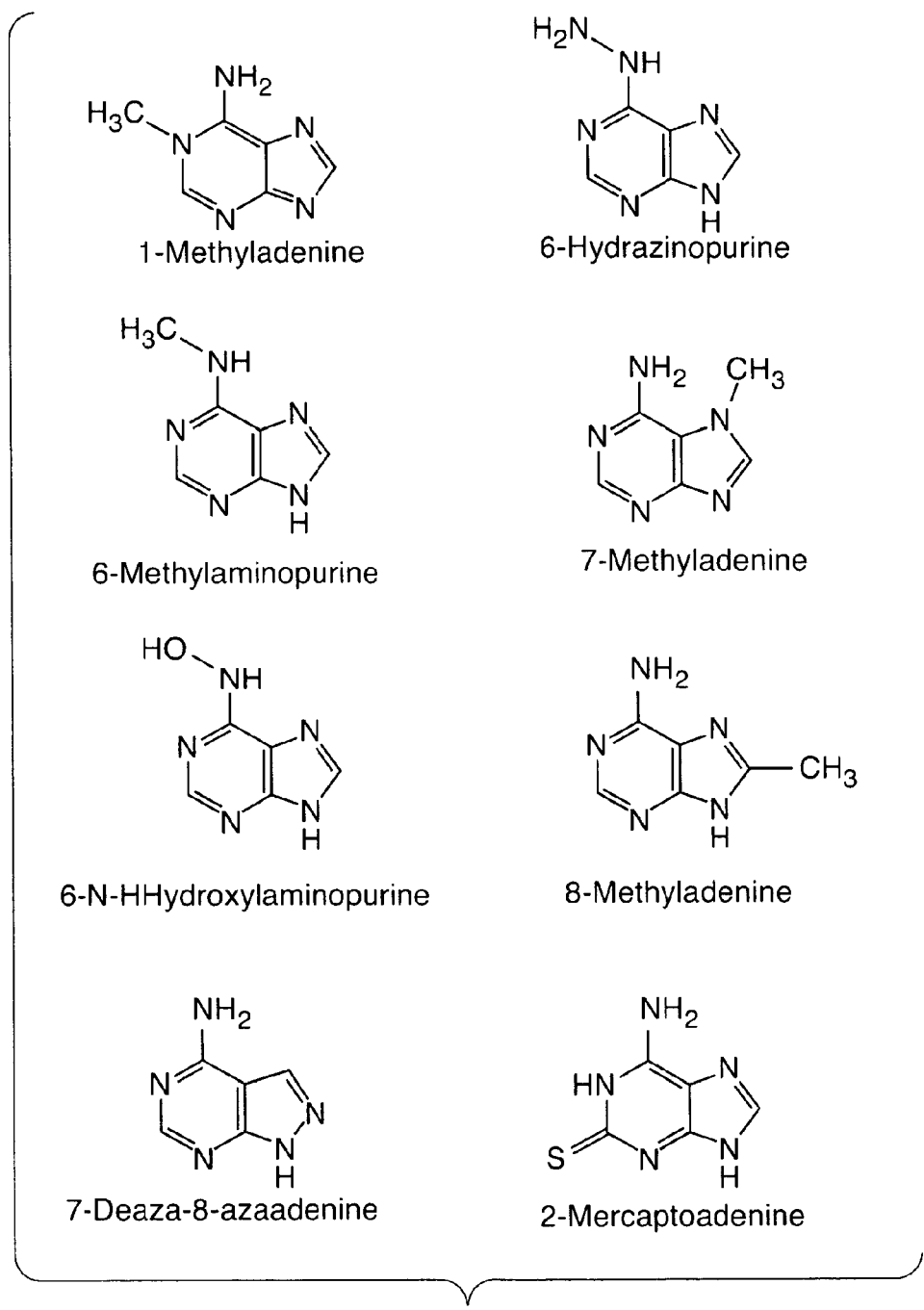
Figure 3C:
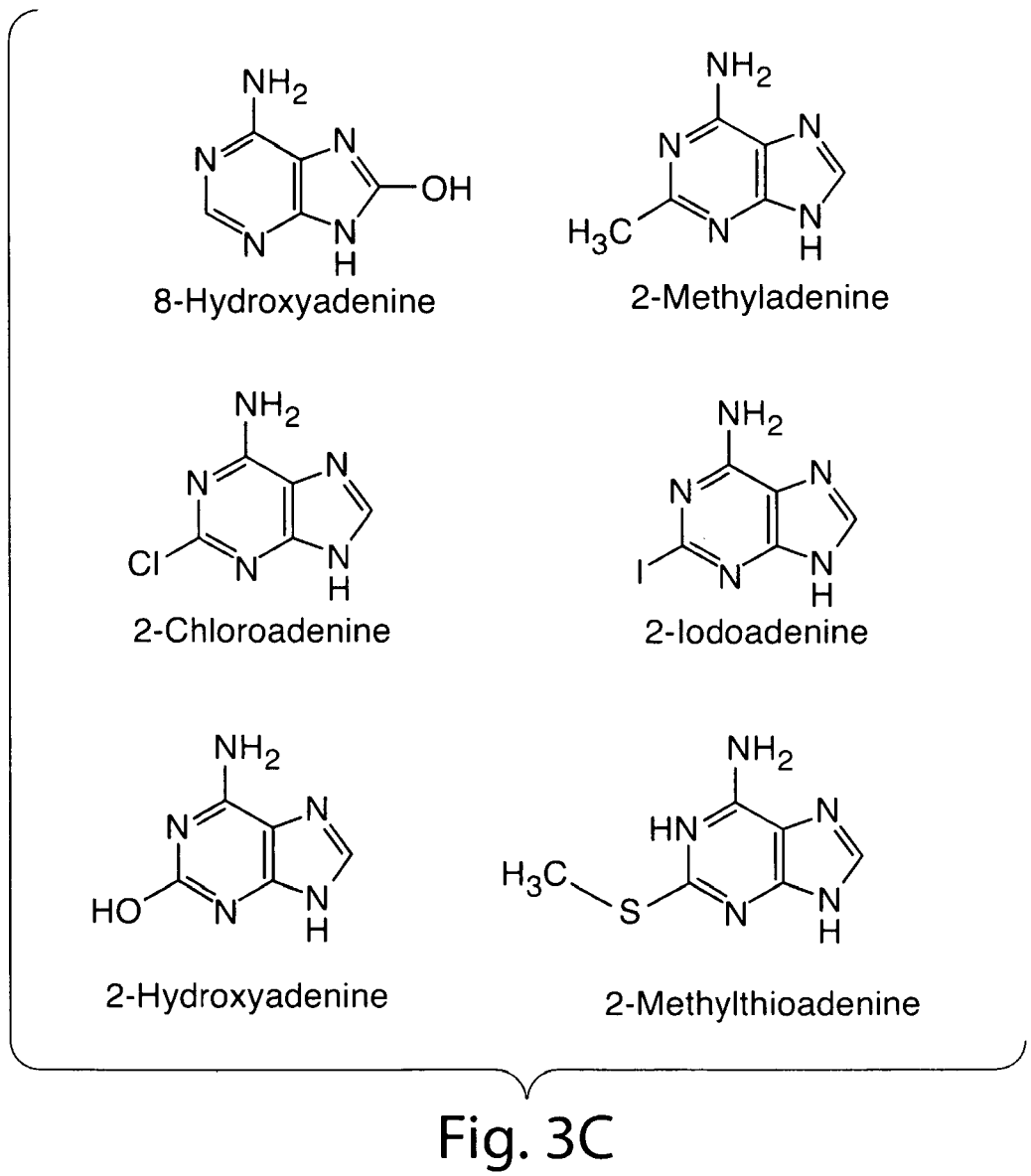

Thus, in some embodiments certain adenine competitive antagonists, including adenine analogs and inhibitors, may be useful in applying the selective therapeutic methods described herein against one or more target cells. An "adenine analog" as used herein refers to a compound which is structurally similar to adenine and which binds to and competitively inhibits the binding of adenine to other molecules. Adenine analogs include: 2,6-diaminopurine, 6-methylpurine, 2-fluoroadenine, 8-azaadenine, 2-azaadenine, 4-aminopyrazolo[3,4-d]pyrimidine, and 8-aza-2,6-diaminopurine. FIG. 3 depicts the chemical structure of various adenine analogs. An "adenine inhibitor" as used herein refers to a compound which inhibits the binding of adenine to other molecules but is not necessarily structurally similar to adenine.

In spite of the extensive data in the literature demonstrating the activity of these particular adenine antagonists against tumors, viruses, bacteria, and protozoa, none have been adopted into clinical practice, in part because of their toxic side effects (J. H. Burchenal et al. "The Effects of the Folic Acid Antagonists and 2,6-Diaminopurine on Neoplastic Disease," Cancer, 4(3): 549-569, May 1951; "The Purine Path to Chemotherapy," Nobel Lecture of Gertrude B. Elion, 12/8/88).

Numerous other adenine analogs and inhibitors, in addition to those mentioned above, are also useful according to the invention and include for instance: 1-methyladenine, 7-deaza-8-azaadenine, 6-methylaminopurine, 6-N-hydroxylaminopurine, 6-hydrazinopurine, 7-methyladenine, 8-methyladenine, 8-hydroxyadenine, and the 2-methyl, 2-chloro, 2-iodo, 2-hydroxy, 2-methylthio, and 2-mercapto derivatives of adenine. Additionally, other known adenine analogs and inhibitors, as well as new ones that may be synthesized, may be useful in the methods described herein.

Without wanting to be bound by any particular theory, adenine analogs which are toxic may require conversion to the corresponding adenine-analog nucleotide (by the enzyme APRT) in order to exert their toxic effects. However, the precise mechanism of the toxic effect may vary depending on the specific adenine analog and the target cell. In many cases, it has been demonstrated that the toxic effects of adenine analogs are due to the incorporation of the fraudulent bases into RNA and DNA with a consequent disruption of the functioning of these nucleic acids, but in other cases additional toxic mechanisms may also be involved, or even predominate, such as, for example, inhibition of the synthesis of nucleic acids, disruption of the synthesis or functioning of adenine -containing coenzymes or of S-adenosylmethionine, perturbations of the interconversions of purine nucleotides, inhibition of ATP-dependent enzymes or of DNA-repair enzymes, inhibition of protein synthesis or production of faulty protein.

The enzyme adenine phosphoribosyltransferase (APRT) which converts adenine, as well as toxic adenine analogs, to the corresponding nucleoside 5'-monophosphates, utilizes 5-phosphoribosyl-1-pyrophosphate (PRPP) as the donor of the phosphoribose group. Mammalian cells have a number of other phosphoribosyl transferase enzymes (PRTs), in addition to APRT, which also utilize PRPP as the phosphoribosyl donor. These other mammalian PRPP-dependent phosphoribosyltransferase include: hypoxanthine-guanine phosphoribosyltransferase (HGPRT; EC 2.4.2.8), which catalyzes the salvage of the purine bases hypoxanthine and guanine to IMP and GMP, respectively; orotate phosphoribosyltransferase (OPRT; EC 2.4.2.10), which, as the fourth step of de novo pyrimidine biosynthesis, converts orotate to OMP; nicotinate phosphoribosyltransferase (NAPRT; EC 2.4.2.11), which converts nicotinate to nicotinate mononucleotide; nicotinamide phosphoribosyltransferase (NAMPRT; EC 2.4.2.12), which converts nicotinamide to its mononucleotide; and quinolinate phosphoribosyltransferase (QPRT; EC 2.4.2.19), which converts quinolinate to nicotinate mononucleotide. (The three last phosphoribosyltransferases, NAPRT, NAMPRT, and QPRT, are all involved in the biosynthesis and metabolism of the coenzyme $NAD^+$—nicotinamide adenine dinucleotide.) Toxic analog substrates for these various other mammalian PRTs (HGPRT, OPRT, NAPRT, NAMPRT, and QPRT), even though they are not adenine analogs and not substrates for APRT, will nevertheless be competitive antagonists of adenine—that is, their conversion to their toxic nucleotide form will be competitively inhibited by adenine. The competitive antagonism in this case depends on competition between the toxic analog and adenine for reaction with 5-phosphoribosyl-1-pyrophosphate (PRPP), catalyzed by their respective phosphoribosyltransferase enzymes. In the case of toxic adenine analogs, by contrast, the competition with adenine is for reaction with PRPP in the same, APRT-catalyzed, reaction. Such toxic analog substrates for the other PRTs, which are competitive antagonists of adenine by this competition for the common PRPP co-reactant, may consequently have their toxic effects on host cells neutralized by increased concentrations of adenine produced by upregulation of the MTAP-pathway in these cells. The effectiveness of selective therapeutic methods described herein was demonstrated using this more extensive class of competitive antagonists of adenine.

As shown in the Examples below MTAP-positive cells, but not MTAP-negative cells, were selectively protected from the toxicity of several important (non-adenine) nucleobase analogs, including the guanine analogs 6-thioguanine (TG) and 8-azaguanine (AzaG)—which are converted to their corresponding nucleotide by HGPRT—and the pyrimidine analog 5-fluorouracil (FU), which is converted to its nucleotide by OPRT. It should be noted that, as in the case of adenine analogs, there may be a variety of mechanisms of action of the nucleotides derived from such other purine and pyrimidine base analogs. For instance, the toxicity of 6-thioguanine to mammalian cells has been shown to depend on the disruption, by the fraudulent nucleotides, of a variety of vital cellular functions, including DNA and RNA functioning and/or synthesis, DNA repair mechanisms, glycoprotein synthesis, and purine nucleotide interconversions.

Besides 6-thioguanine, 8-azaguanine, and 6-mercaptopurine, many other analogs of the purines guanine and hypoxanthine, which are also good alternative substrates for HGPRT, have been synthesized. Included among these other guanine analogs are: 3-deazaguanine, 1-methylguanine, 2-amino-6-methylthiopurine, 2-amino-6-methoxypurine, 2-amino-6-benzylthiopurine, and 1-methyl-6-thioguanine. Included among these other hypoxanthine analogs are: 8-azahypoxanthine, 6-chloropurine, 2,6-dimercaptopurine, 2-hydroxy-6-mercaptopurine, 6-methylthiopurine, 6-ethylthiopurine, 6-benzylthiopurine, 6-propylthiopurine, 9-ethyl-6-mercaptopurine, 9-butyl-6-mercaptopurine, 1-methylhypoxanthine, and 1-methylpurine-6-thione.

Some of these analogs have been shown to be toxic to various tumors or other target cells (such as viruses, bacteria, and protozoa). In some embodiments these guanine and hypoxanthine analogs, as well as others not yet examined or synthesized, may be used in selective therapeutic methods described herein against one or more target cells.

The cancer drug 5-fluorouracil (FU) is converted to its toxic nucleotide derivative by orotate phosphoribosyltransferase (OPRT). A number of other analogs of uracil and orotate have been synthesized and shown either to be good substrates for OPRT or to effectively inhibit the enzyme. Included among these uracil analogs are: 3-deazauracil, 3-oxauracil, 5-azauracil, 5-chlorouracil, 5-nitrouracil, 5-aza-3-deazauracil, 6-azauracil, 6-chlorouracil, 6-aminouracil, 6-hydroxyuracil, 6-carboxymethyluracil, and 6-methylsulfonyluracil. Included among these orotate analogs are: 5-azaorotate, 5-fluoroorotate, 5-nitroorotate, 6-methylorotate, and 1-deazaorotate. Some of these alternative substrates for OPRT have demonstrated inhibitory activity against various target cells, such as tumors, viruses, protozoa, and bacteria. In some embodiments these pyrimidine analogs, as well as others not yet examined or synthesized, may be used in selective therapeutic methods described herein against one or more target cells.

Very few analogs of the pyridines nicotinate, nicotinamide, and quinolinate have been synthesized and examined for activity as alternative substrates for the enzymes NAPRT, NAMPRT, or QPRT and for potential as therapeutic agents. However, in some embodiments, using methods well known in the art, a large number of pyridine analog substrates for NAPRT, NAMPRT, and QPRT may be synthesized and screened for their use in the methods described herein.

The sulfur-containing amino acid methionine plays an important role in a variety of cellular functions, in addition to its role as an essential component of proteins. These cellular functions include: the initiation of protein synthesis; numerous S-adenosylmethionine-dependent transmethylation reactions; the synthesis of polyamines; the synthesis of cysteine, glutathione, and other metabolites via the transsulphuration pathway; and the supply of homocysteine, which is needed for the metabolism of intracellular folates.

A number of analogs of methionine have been synthesized and examined for biological activity. Many of these analogs have been shown to be competitive antagonists of methionine and to inhibit or kill a variety of target cells, including tumors, viruses, bacteria, fungi, and protozoa. (A. Meister, ed., *Biochemistry of the Amino Acids,* 2nd ed., Volume 1, 1965, 233-238). Although the precise mechanism of the toxic effects of these competitive antagonists of methionine varies, depending on the particular analog and its milieu, it has been shown in many cases that the toxic action is due either to incorporation of the analog into protein resulting in dysfunctional species, or because of disruption of one or more of the other critical functions of methionine mentioned above.

Figure 4:
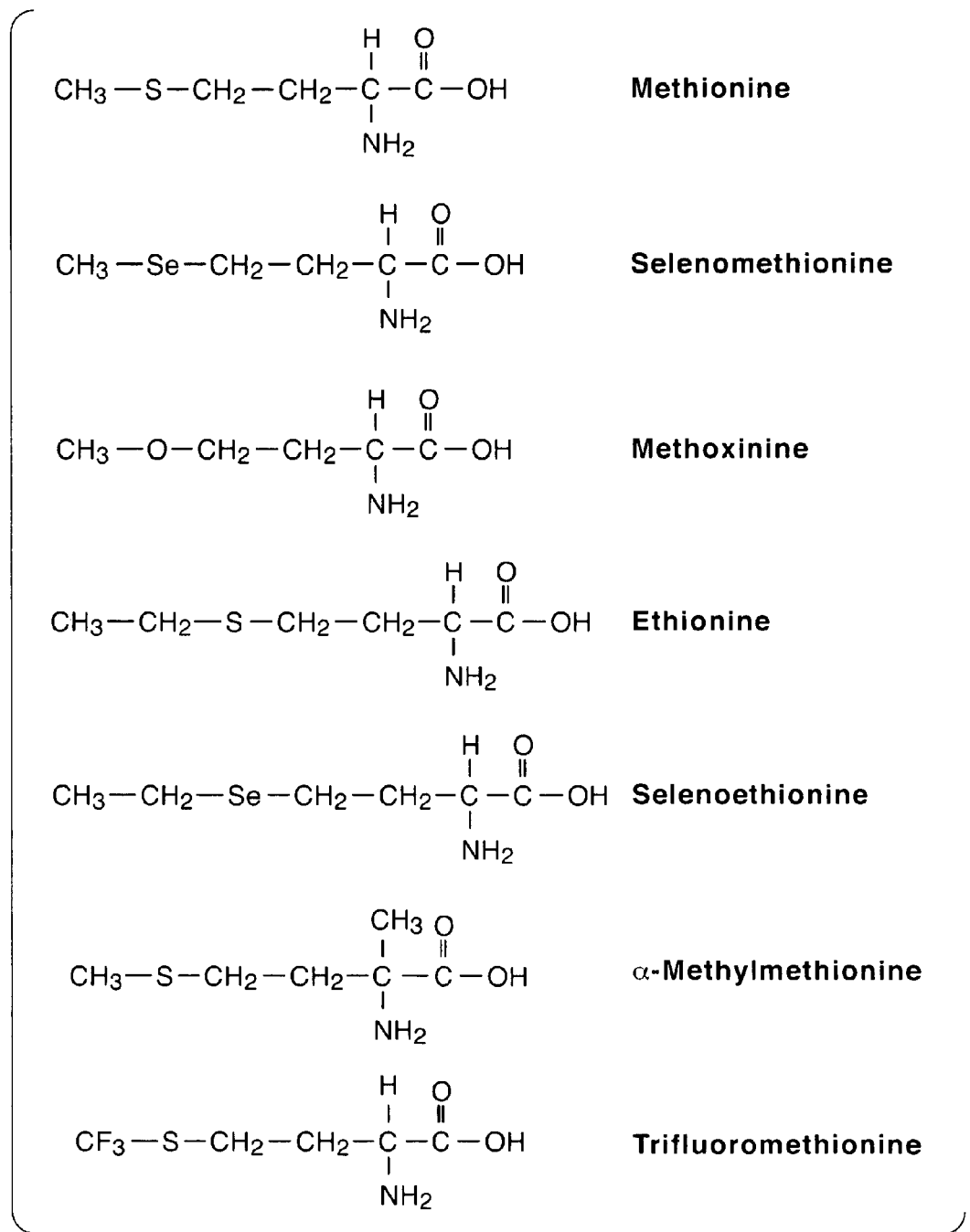
FIG. 4 depicts the structure of methionine and some methionine analogs useful in certain embodiments of the invention.

In some embodiments, certain methionine analogs which have been examined to date, may be useful in selective therapeutic methods described herein against one or more target cells; such methionine analogs include, but are not limited to: ethionine, selenomethionine, methoxinine, selenoethionine, α-methylmethionine, and trifluoromethionine. FIG. 4 depicts the chemical structure of these methionine analogs.

Many other competitive antagonists of adenine and methionine, not mentioned here, which may be synthesized by techniques well-known in the art, as well as prodrugs of adenine and methionine antagonists, may also prove useful in the methods described herein.

Prodrugs may be designed to improve physicochemical or pharmacological characteristics of an adenine or methionine antagonist. As one non-limiting example, capecitabine is an oral prodrug of 5-fluorouracil that may be advantageously used with the methods described herein.

Numerous analogs are described in the patent literature. For instance, U.S. Pat. Nos. 5,484,946; 4,782,173; 3,472,838; 5,106,837; 5,889,178; 4,663,313; 5,219,839; 5,459,255; 5,446,139 and 4,985,409 describe analogs and methods of synthesis of analogs. Each patent is incorporated by reference.

A "protective agent" as used herein is a compound that increases the activity or levels of a cell metabolite in a host cell, for instance, by any of the methods described herein, so as to protect the host cell from the toxicity of a competitive antagonist of the cell metabolite. The increased activity or levels of the cell metabolite may be accomplished, for instance, by increasing synthesis or decreasing degradation of the cell metabolite in the host cell, or by increasing influx of the cell metabolite into the cell or decreasing its efflux out of the cell. In certain preferred embodiments, the method of increasing the activity or levels of the cell metabolite in the host cells, avoids increasing the activity or levels of the metabolite in the target cell. The method may involve a selective upregulation of the synthesis of the cell metabolite in the host cells using a protective agent. In one embodiment the cell metabolite is a product of a metabolic pathway in the host cells and the protective agent increases the level of the cell metabolite in the host cells by increasing the activity of the metabolic pathway so as to increase the production of the cell metabolite. Depending on the nature of the metabolic pathway, and the host cells, there may be a variety of ways to upregulate its activity, including, but not limited to: providing increased concentrations of substrates, intermediates, cofactors, enzymes, or other reactants in the metabolic pathway; modulating a regulator of the metabolic pathway, such as a regulatory molecule or enzyme; or providing analogs of substrates or other reactants in the metabolic pathway which increase the production of the cell metabolite. Methods of increasing the concentrations of substrates, intermediates, cofactors, enzymes, or other reactants in the metabolic pathway, or of modulating a regulator of the metabolic pathway, include, but are not limited to, directly supplying these molecules, or increasing their synthesis (for instance, by increasing the transcription or translation of genes, or production of microRNAs, involved in their synthesis), In preferred embodiments, the toxic effects of the competitive antagonist in the target cell are not blocked by the protective agent. In such a circumstance the toxic effect of the competitive antagonist is exerted on the target cell and the host cell is protected from toxicity by the protective agent; in this case, the host cell is said to be "selectively protected" from the toxicity of the competitive antagonist by the protective agent. When the toxic effects are not blocked in the target cell, the target cell can be inhibited. A target cell is said to be inhibited if any target cell activity is decreased. For instance, inhibition of a target cell includes any slowing in growth of the target cell, reduction in pathogenic properties of a target cell or death of the target cell. A reduction of pathogenic properties of the target cell is a reduction in any property of the target cell that is harmful to the host. For instance if the target cell is a tumor cell, a pathogenic property is rapid cell division. If the target cell is an infectious agent, a pathogenic property is ability of the target cell to damage host cells.

The protective agent may act through any mechanism which increases the activity or levels of the cell metabolite in the host cells, whether or not it affects the activity or level of the cell metabolite in the target cell. In preferred embodiments, the effect, if any, of the protective agent on the target cell does not significantly diminish the toxicity of the competitive antagonist to the target cell; in these preferred embodiments, the protective agent thus provides selective protection of host cells (and hence the subject) from the toxicity of the competitive antagonist. A protective agent which specifically increases the intracellular levels of the cell metabolite in the host cells, but which has minimal or no effect on increasing the level of the metabolite in the target cell, might be utilized. A protective agent which selectively increases the levels of the cell metabolite in the host cells, but not in the target cell, may have a desired effect, such as neutralizing the toxicity of a competitive antagonist of the cell metabolite to the host cells but not to the target cell. A method for selectively increasing the levels of the cell metabolite in the host cells, but not in the target cell, may involve a selective upregulation of the synthesis of the cell metabolite in the host cells. In these embodiments, the cell metabolite may be the product of some metabolic pathway in the host cells, and the method of increasing the levels of cellular metabolite in the host cells may be to provide a protective agent which increases the activity of the metabolic pathway, so as to increase the production of the cellular metabolite. In some embodiment the metabolic pathway may be either a simple, single-step metabolic pathway involving one enzyme acting on one or more substrates, or a multi-step pathway involving a number of substrates, intermediates, enzymes, and enzyme cofactors. In certain embodiments, depending on the nature of the metabolic pathway, and the host cells, there may be a variety of ways to upregulate its activity. These methods may include, but are not limited to: providing increased concentrations of substrates, intermediates, cofactors, enzymes, or other reactants in the metabolic pathway; modulating a regulator of the metabolic pathway, such as a regulatory molecule or enzyme; providing precursors of some of these molecules, e.g., precursors of substrates or of intermediates in the metabolic pathway; providing analogs of some of these molecules, e.g., analogs of substrates or intermediates, or analogs of precursors of the same. Protective agents useful according to the invention thus include, but are not limited to: substrates and other reactants of the metabolic pathway; analogs of substrates and other reactants of the metabolic pathway; precursors of substrates or other reactants of the metabolic pathway; and analogs of precursors of substrates or other reactants of the metabolic pathway.

The metabolic pathway may be entirely absent, or have very low activity, in the target cell. In such an instance, administering the protective agent to the subject while treating the subject's disease with the drug, competitive antagonist, may produce increased levels of the cellular metabolite in the host cells but little or no increase in levels of the cellular metabolite in the target cell. The host cells, and hence the subject, are thus protected from the toxicity of the drug without compromising the effectiveness of the drug against the target cell.

An identical or homologous metabolic pathway, leading to the production of the cell metabolite, may exist in the target cell. Exposure of the target cell to the protective agent may thus cause an increased production of the cell metabolite in the target cell, and thus possibly reduce or eliminate the toxic effects of the competitive antagonist in the target cell (such may be the case if, e.g., the toxic effects of the competitive antagonist in the target cell are mediated in the same way as in the host cells). The methods of the invention may still be useful in such a circumstance, however, by selectively inhibiting this metabolic pathway in the target cell. In these embodiments there may be a variety of ways of achieving such selective inhibition of this pathway using a target cell inhibitory agent. A "target cell inhibitory agent" as used herein is a compound that selectively inhibits the activity of the metabolic pathway in the target cell; that is, it inhibits the identical, or homologous, metabolic pathway that leads, in the target cell, to the production of the cell metabolite, but it has substantially no effect on the activity of the metabolic pathway in the host cells. A target cell inhibitory agent of the instant invention may operate in any manner which reduces the activity of the metabolic pathway selectively in the target cell. For example, the homologous pathway in the target cell, leading to the cellular metabolite, may involve one or more enzymes which differ enough in structure from the homologous enzymes of the host cell pathway to allow the development of specific inhibitors; alternatively, the genes which produce the differing enzymes, in the target and host cells, may differ enough in sequence to allow the development of specific inhibitors of the gene, or of its mRNA transcript, in the target cell. In embodiments wherein the pathway in the target cell is identical to the pathway in the host cells, differences in the way the activities of the two pathways are regulated may allow for selective downregulation of the pathway in the target cell. For example, in some embodiments wherein the target cell is a neoplasm and the metabolic pathway is active in the tumor cells only when they are dividing, an agent might be administered which blocks a proliferation-signaling pathway in the tumor cell, thus inhibiting the activity of the metabolic pathway. For instance, one might utilize an antagonist of a tumor-specific growth factor, as a target cell inhibitory agent.

Additional sources of the cellular metabolite may be available in some target cells, even when the metabolic pathway, or a homologous pathway, is nonexistent in the target cell or has been intentionally inhibited therein. For example, the cellular metabolite may be available, exogenously, from the subject's circulation, or by synthesis through other pathways in the target cell. In such embodiments, wherein the cellular metabolite is available to the target cell through other routes, it may be advantageous to provide ways to inhibit these other routes. In embodiments wherein the cellular metabolite, or a precursor, is for example available from the subject's circulation, dietary restrictions or administration of enzymes which degrade the cellular metabolite (or a precursor) in the plasma, might be utilized. In embodiments wherein the target cell has other metabolic pathways leading to the cellular metabolite, specific inhibitors of these pathways are useful in potentiating the therapeutic method of the instant invention.

In some embodiments the protective agent is a substrate or an analog of a substrate. The substrate is processed in the host cell under normal conditions to produce the cellular metabolite. By providing additional substrate or analog of the substrate to the host cells during therapy with the competitive antagonist, the host cell is enabled to produce enough cellular metabolite to avoid the toxic effects of the competitive antagonist. A substrate or analog of a substrate as used herein refers to any compound that is acted upon by an enzyme to produce the cellular metabolite. Referring to the example described above relating to MTAP, an example of a MTAP substrate useful according to the methods of the invention is a MTA compound. MTA compounds include MTA and analogs thereof. MTA and analogs of MTA are useful as protective agents in the methods of the invention when the cell metabolite is adenine or methionine. As used herein, an "analog of MTA" refers to any compound related to MTA in physical structure or composition, or other characteristics, and which is capable of providing a cleavage site for MTAP. Synthetic analogs can be prepared to provide a substrate for cleavage by MTAP, which in turn provides adenine or methionine. Another example of a group of protective agents that are substrates or analogs thereof are substrates of the methionine salvage pathway.

The MTAP-pathway has been studied extensively in vitro and in vivo. In tissue culture experiments on many different kinds of MTAP-positive, proliferating mammalian cells, 5'-deoxy-5'-methylthioadenosine (MTA) has been shown to be rapidly taken up by the cells and to produce adenine and methionine through the MTAP-pathway, in quantities sufficient to satisfy the purine and methionine requirements of the growing cells. In in vivo studies, MTA has been shown to be non-toxic to mice and rats at very high doses, after both acute and long-term administration, and whether provided orally or parenterally. In oral feeding experiments, MTA has been shown capable of replacing the methionine requirements of young, growing rats restricted to a methionine-free diet. This indicates that MTA has good oral bioavailability, is taken up by dividing cells throughout the rat, and is metabolized in these cells to methionine and adenine.

MTA is useful according to the invention in protecting normal, proliferating cell populations from the toxicity of adenine and/or methionine competitive antagonists. The MTA analog 5'-deoxyadenosine (5'-dAdo) has also been shown to be rapidly taken up by MTAP-positive mammalian cells and to generate adenine through the MTAP-pathway. (It does not generate methionine, however, because of the lack of a methylthio group on the ribose.) 5'-dAdo has also been shown to be non-toxic at high doses in mice. Thus, 5'-dAdo is a suitable protective agent in the methods described herein.

MTA can be prepared according to known methods as disclosed in Kikugawa et al. J. Med. Chem. 15, 387 (1972) and Robins et al. Can. J. Chem. 69, 1468 (1991). An alternate method of synthesizing MTA is provided in U.S. Pat. Application 20040043959, which is incorporated by reference for disclosing the synthesis method.

Figure 5:
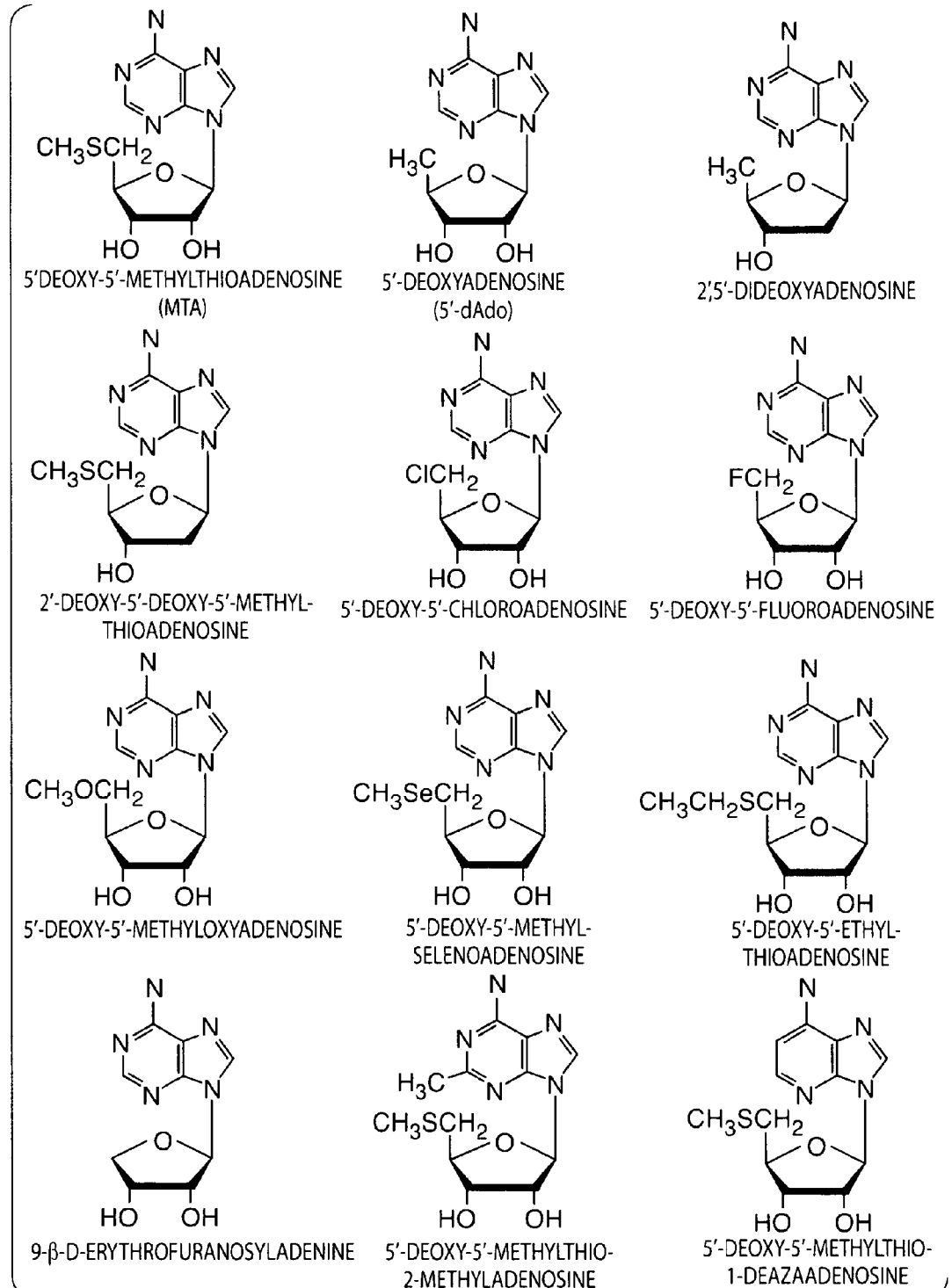
FIG. 5 depicts the structure of MTA and some MTA analogs useful in certain embodiments of the invention.

Other analogs of MTA that are excellent substrates for the enzyme MTAP, in addition to 5'-deoxyadenosine, include, but are not limited to, for instance: 2',5'-dideoxyadenosine, 2'-deoxy-5'-deoxy-5'-methylthioadenosine, 5'-deoxy-5'-chloroadenosine, 5'-deoxy-5'-fluoroadenosine, 5'-deoxy-5'-methyloxyadenosine, 5'-deoxy-5'-methylselenoadenosine, 5'-deoxy-5'-ethylthioadenosine, 9-β-D-erythrofuranosyladenine, 5'-deoxy-5'-methylthio-2-methyladenosine, and 5'-deoxy-5'-methylthio-1-deazaadenosine. The first eight of these analog substrates are modified only in the ribose portion of MTA and will generate adenine, but not methionine, through the MTAP-pathway. The last two analogs, modified only in the adenine moiety of MTA, will generate methionine, but not adenine, through the MTAP-pathway. Toxicity data and pharmacokinetic data for all of these MTA analogs can be obtained by techniques well-known in the art. Each of these MTA analogs, in addition to MTA, may be useful as a protective agent against the toxicity of adenine or methionine competitive antagonists, according to the invention. FIG. 5 depicts the chemical structure of these various MTA analogs.

In some embodiments, analogs of MTA, not mentioned here or not yet synthesized, may also be used in the methods described herein. Such analogs may be synthesized by techniques well-known in the art and tested for suitability as protective agents. Besides MTA substrates, other agents that may be utilized as protective agents in the methods described herein include, but are not limited to, precursors of MTA, analogs of such precursors of MTA, and prodrugs of MTAP substrates.

Many other MTA analogs that are substrates for MTAP and that may be useful in the methods described herein are disclosed in U.S. Pat. Publication 20040043959 and in *Design, synthesis, and biological evaluation of novel human 5'-deoxy-5'-methylthioadenosine phosphorylase (MTAP) substrates*, P P Kung et al, Bioorg Med Chem Lett, Jun. 2005; 15(11): 2829-33, which are incorporated by reference herein in their entirety.

In healthy cells, natural precursors of MTA will be converted to MTA for action by MTAP. As used herein, a "precursor" is a compound from which a target compound is formed via one or a number of biochemical reactions. A "precursor of MTA" is an intermediate which occurs in the formation of MTA. For example, precursors of MTA include, but are not limited to, S-adenosylmethionine (SAM) or decarboxylated S-adenosylmethionine (dcSAM).

In addition, synthetic analogs of MTA precursors can be prepared. As used herein, an "analog of an MTA precursor" refers to a compound related in physical structure or composition, or other characteristics, to an MTA precursor, e.g., SAM or dcSAM, and which acts as an intermediate in the formation of an MTAP substrate.

Prodrugs of MTAP substrates may also be useful in certain embodiments of the invention as protective agents. Prodrugs may be designed to improve physicochemical or pharmacological characteristics of the MTAP substrate. For example a prodrug of a MTAP substrate may have functional groups added to increase its solubility and/or bioavailability or other characteristics. Prodrugs of MTAP substrates are disclosed, for example, in J. Org. Chem. (1994) 49(3): 544-555, the disclosures of which are hereby incorporated by reference in its entirety.

Prodrugs of MTAP substrates include, but are not limited to, carbamates, esters, phosphates, and diamino acid esters of MTA or of MTA analogs. Additional prodrugs can be prepared by those skilled in the art. For example, the 2',3'-diacetate derivatives of 5'-deoxy 5'-methylthioadenosine (J. R. Sufrin et. al. J. Med. Chem. 32, 997 (1989)), 5'-deoxy 5'-ethylthioadenosine, and 5'-iso-butylthio 5'-deoxyadenosine can be prepared according to the methods described in J. Org. Chem. 59, 544 (1994).

See also, e.g., Bertolini et al., J. Med. Chem. (1997), 40:2011-2016; Shan et al., J. Pharm. Sci. (1997), 86 (7):765-767; Bagshawe, Drug Dev. Res. (1995), 34:220-230; Bodor, Advances in Drug Res. (1984), 13:224-331; Bundgaard, Design of Prodrugs (Elsevier Press 1985); Larsen, Design and Application of Prodrugs, Drug Design and Development (Krogsgaard-Larsen et al. eds., Harwood Academic Publishers, 1991); Dear et al., J. Chromatogr. B (2000), 748:281-293; Spraul et al., J. Pharmaceutical & Biomedical Analysis (1992), 10 (8):601-605; and Prox et al., Xenobiol. (1992), 3 (2):103-112.

Other protective agents that may prove useful in the methods described herein include MTR-1-P and any intermediate compounds formed from MTR-1-P in the methionine salvage pathway. Some synthetic analogs of MTR-1-P and intermediate compounds may be converted by the pathway to methionine. As used herein, MTR-1-P, intermediate compounds of the pathway, as well as synthetic analogs of the foregoing that may be converted by the pathway to methionine, are referred to as substrates of the methionine salvage pathway.

The methods described herein may be potentiated by combining them with methods for increasing the size of the host cell population. Methods for expanding the host cell population may include, but are not limited to, various hormones, growth factors, and cytokines. For instance, a variety of growth factors that can expand hematopoietic cell populations are known in the art and some, such as erythropoietin (Epogen; Amgen) and granulocyte colony-stimulating factor (Neupogen; Amgen), are already in use in clinical practice. There are also hormones and growth factors known that can promote proliferation of the gastrointestinal epithelium, e.g., keratinocyte growth factor (KGF; Amgen).

In the treatment of various diseases according to the methods described herein more than one competitive antagonist of the cellular metabolite may be administered. In such embodiments, administration of more than one competitive antagonist may provide additive or synergistic, toxic action against the target cell, without compromising the ability of the protective agent to protect the host cells. Synergistic toxic action of two competitive antagonists against the target cell may occur when two competitive antagonists antagonize the cellular metabolite by different modes (e.g., by competing for two different enzymes acting on cellular metabolite). In certain embodiments, application of two or more competitive antagonists, exerting toxicity against the target cell through different mechanisms, may also provide significant reduction in the risk of emergence of resistant strains of the target cell.

Referring to the example described above relating to MTAP, in certain embodiments an adenine and methionine competitive antagonist, both inhibitory to the target cell, may be administered together. Administration of an adenine and methionine antagonist, together, may provide additive or synergistic toxic action against a target cell, particularly wherein the adenine and methionine antagonists exert their toxic actions by different mechanisms. Such joint administration of adenine and methionine antagonists will not compromise the ability to selectively protect the host cells in embodiments wherein one or more suitable substrates for MTAP (i.e., MTA or suitable analog of MTA, which can generate sufficient adenine and methionine together) is co-administered.

In certain embodiments, wherein adenine and methionine antagonists are administered together exerting toxicity against a target cell through different mechanisms, such joint administration may also provide a significant reduction in the risk of resistant strains of the target cell emerging during treatment and defeating the therapy.

In certain embodiments synergistic toxic action against the target cell, and reducing the risk of resistance emerging, may also be obtained by the administration of two different adenine competitive antagonists (which have at least two different modes of toxicity of their analog nucleotides against a target cell) or by the administration of two different methionine competitive antagonists (which have at least two different modes of toxicity against a target cell).

The methods described herein relate to the treatment of diseases such as infectious diseases and cancer as well as diseases with overactive cell proliferation, such as, for example: non-malignant or pre-malignant lesions or proliferative diseases; inflammatory, allergic, or autoimmune diseases; atherosclerosis and vascular stenosis and restenosis; and allograft tissue rejection.

As used herein, "tumor" and "cancer" are used interchangeably. The cancer or tumor may be malignant or non-malignant. Cancers or tumors include but are not limited to biliary tract cancer; bladder cancer, brain cancer; breast cancer; cervical cancer; choriocarcinoma; colon cancer; endometrial cancer; esophageal cancer; gastric cancer; intraepithelial neoplasms; lymphomas; liver cancer; lung cancer (e.g., small cell and non-small cell); melanoma; neuroblastomas; oral cancer; ovarian cancer; pancreas cancer; prostate cancer; rectal cancer; sarcomas; skin cancer; testicular cancer; thyroid cancer; and renal cancer, as well as other carcinomas and sarcomas, hairy cell leukemia, chronic myelogenous leukemia, cutaneous T-cell leukemia, multiple myeloma, follicular lymphoma, malignant melanoma, squamous cell carcinoma, renal cell carcinoma, prostate carcinoma, bladder cell carcinoma, or colon carcinoma.

As used herein, the terms "treat," "treated," or "treating," when used with respect to an adverse condition such as a disorder or disease, for example, an infectious disease, cancer, or an allergic reaction, may refer to prophylactic treatment which increases the resistance of a subject to development of the adverse condition, in other words, decreases the likelihood that the subject will develop the adverse condition, as well as refers to the treatment after a subject has developed the adverse condition, or essentially coinciding with the development of the adverse condition, in order to fight the disease, or prevent the adverse condition from becoming worse. Desired outcomes may include a stabilization of the condition, a slowdown in progression of the disease or a full disease-free recovery of the subject.

The methods described herein may be combined with other treatment modalities. For example, in the therapy of neoplastic disease, methods described herein may be combined with other antineoplastic chemotherapies and/or with radiation therapy or surgical treatment.

For many malignant tumors of mammals, a certain proportion (in some cases, a high proportion) of the tumor cells are in a quiescent, non-dividing state. Such quiescent tumor cells are, in general, quite resistant to the toxic effects of antineoplastic drugs, including many of the toxic competitive antagonists of cell metabolites of the instant invention. Methods exist, however, that may be used to induce these quiescent tumor cells to begin proliferation, which may then make them more sensitive to treatment by the selective therapies described herein. Such methods of inducing tumor-cell proliferation include, but are not limited to, surgical debulking of a tumor mass (i.e. the surgical removal of a large portion of a tumor mass, which pushes a significant number of the remaining tumors cells from G0 to G1 phase, due to increased availability of nutrients, oxygen, etc.) and the provision of increased levels of specific growth factors, required by the tumor cells. Many viruses, bacteria, and protozoa that infect humans or other mammals, may also exist, within the subject, in a non-proliferating or "latent" state or phase. Included among the viruses that may exist in a latent condition are many with a significant impact on human health, such as, the human immunodeficiency virus, herpes viruses, hepatitis B, Epstein Barr virus, and human cytomegalovirus. Other important pathogens infecting humans, which may exist in a latent state, include members of the protozoal genus *Plasmodia* (the cause of malaria) and the bacterium, *Mycobacterium tuberculosis* (the cause of tuberculosis). Methods have been developed, or are under development, to induce various latent pathogens into a proliferative state, which would then make them more sensitive to destruction by chemotherapeutic agents including agents of the present invention. In some aspects, methods of inducing a cancer cell or an infectious pathogen out of a non-proliferating condition or latent state may be combined with certain selective therapeutic methods of the instant invention in order to eradicate the cancer cell or pathogen from the subject.

Some embodiments of the invention relate to the treatment of disease in humans, and other mammals, with competitive antagonists of adenine and/or methionine. In these embodiments, a competitive antagonist of adenine or methionine, which is known to inhibit or kill the target cell in the afflicted subject, is administered. At substantially the same time, or a somewhat earlier or later time, a protective agent such as MTA, or an analog of MTA, is administered to the subject in order to generate sufficient adenine or methionine in host cells of the subject, via the pathway initiated by the enzyme MTAP, to neutralize the toxicity of the competitive antagonist to this cell population. If the enzyme MTAP is absent from a target cell, or has lowered activity therein, or can be specifically downmodulated in the target cell, such a treatment regimen may result in protection of the subject from the toxicity of the adenine or methionine antagonist without compromising its inhibitory or lethal action against the target cell. FIG. 1 provides a schematic depiction of certain selective therapeutic methods, described herein.

Figure 2:
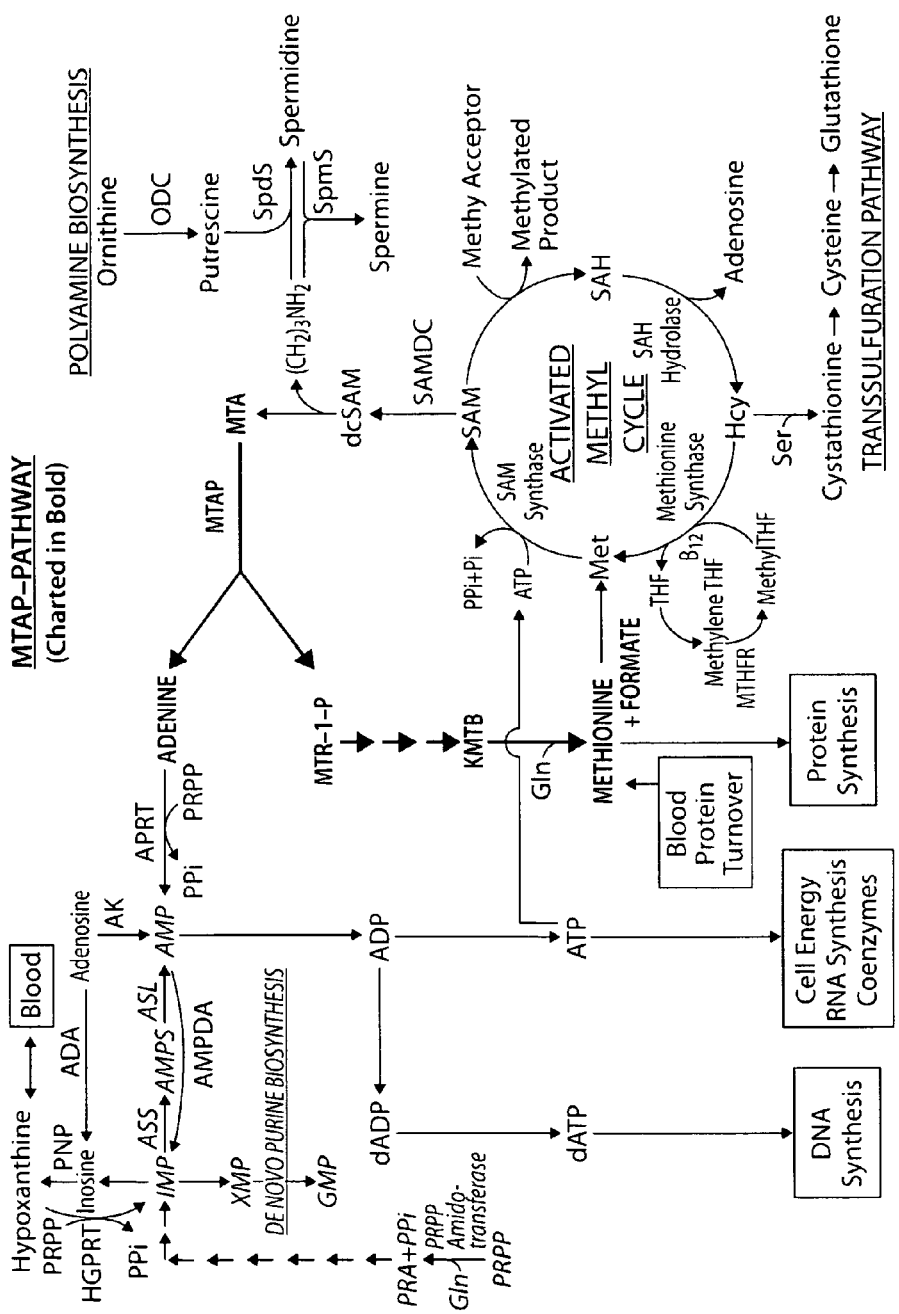
FIG. 2 is a schematic depiction of the MTAP-pathway in mammalian cells, and its interconnections with the pathways of polyamine biosynthesis, the activated methyl cycle, and purine metabolism.

FIG. 2 provides a schematic depiction of the metabolic pathway in mammalian cells that involves MTAP and MTA, as well as other intracellular metabolic pathways that may lead to adenine nucleotides and methionine. The mammalian enzyme MTAP catalyzes the phosphorolysis of the thionucleoside 5'-deoxy-5'-methylthioadenosine (methylthioadenosine; MTA), a metabolite of S-adenosyl-L-methionine (SAM) produced during the synthesis of the polyamines spermidine and spermine, to yield adenine and 5-methylthioribose-1-phosphate (MTR-1-P). Both of these products of MTAP catalysis are reused: adenine is returned to the adenine nucleotide pool via the enzyme adenine phosphoribosyltransferase (APRT, EC 2.4.2.7) and MTR-1-P is metabolized by a series of additional steps to methionine and formate. The entire metabolic pathway which leads from MTA to the formation of adenine, methionine, and formate is referred to herein as the MTAP-pathway, as its initiating step is the cleavage of MTA by the enzyme MTAP (see FIG. 2). The portion of the MTAP-pathway that leads from MTR-1-P to methionine and formate is sometimes referred to, in the art, as "the methionine salvage pathway," and is referred to as such, herein.

The MTAP-pathway appears to be highly active in all normal, proliferating, mammalian cells. Therefore, providing MTA, or a suitable analog of MTA, to these cells can generate adenine and/or methionine in these cells, thus protecting them from the toxic effects of competitive antagonists of adenine and/or methionine. In particular, cell populations critical to the health of the subject which would ordinarily be highly sensitive to adenine and methionine antagonists, such as the progenitors of the hematopoietic system and the epithelium of the gastrointestinal and oral mucosa, can be protected from toxicity by these methods.

Large numbers of adenine analogs have been synthesized and examined for activity against tumors and various infectious organisms, including viruses, bacteria, and protozoa. Many of these adenine analogs have been shown to be competitive antagonists of adenine in mammalian cells, via competition for phosphoribosylation by the adenine salvage enzyme adenine phosphoribosyltransferase (APRT), and to inhibit or kill (following their conversion, by APRT, to a nucleotide analog) a variety of target cells.

Some embodiments of the present invention relate to a selective therapy involving competitive antagonists of adenine and/or methionine, and protection of the subject with MTA (or a suitable analog), for the treatment of human tumors that are deficient in the enzyme MTAP. About thirty years ago, several murine tumors deficient in the enzyme MTAP were identified (J. I. Toohey, Biochem. Biophys. Res. Commun., 78:1273-1280, 1977). Since then, it has been found that many tumors of mammals, particularly human tumors, are entirely deficient in this enzyme, due to homozygous deletion of the MTAP gene. Tumors, or other target cells, that have no activity of the enzyme MTAP, or activity of the enzyme MTAP which is substantially lower than that of normal, proliferating cells of the subject, are referred to, herein, as MTAP negative. As used herein, "MTAP negative", "MTAP-negative", "MTAP deficient", and "MTAP-deficient" are all used interchangeably. A tumor, or other target cell, that has activity of the enzyme MTAP that is not substantially lower than that of normal, proliferating cells of the subject, is referred to, herein, as MTAP positive (or MTAP-positive, i.e., with a hyphen). In most cases, a human tumor is MTAP negative because of homozygous deletion of the MTAP gene. But in some cases, the tumor is MTAP negative because one copy of the MTAP gene is deleted and the other copy is not transcribed into functional enzyme, due to such causes as mutation of the gene or hypermethylation of the gene's promoter; and in other cases, a tumor has both copies of the gene, but is nevertheless MTAP negative because neither copy is transcribed into functional enzyme due to such causes as the foregoing.

The human MTAP gene is located on the short arm of chromosome 9, in the 9p21 band, a region which also harbors the tumor suppressor genes p16INK4a, its alternate -transcript p14ARF, and p15INK4b. Without wanting to be bound by any particular theory, it appears that because of its close proximity (100 kb telomeric) to this tumor suppressor gene locus, the MTAP gene is frequently co-deleted along with p16/p14 (and sometimes p15) in many tumors. However, MTAP deletions have also been found in many tumors that are p16-positive, apparently because of fragile sites within the MTAP gene itself (WO 99/67634).

Although definitive data is not yet available, it appears that between 10 and 25 percent of all human tumors have homozygous deletions of the MTAP gene. Homozygous deletions of the MTAP gene have been found in small cell (Merlo A., Gabrielson E., Mabry M., Vollmer R., Baylin S. B., Sidransky D., Cancer Res., 54: 2322-2326, 1994; and Olopade O. I., Buchhagen D. L., Malik K., Sherman J., Nobori T., Bader S., Nau M. M., Gazdar A. F., Minna J. D., Diaz M. O., Cancer Res. 53: 2410-2415, 1993) and non-small cell (Olopade O. I., Buchhagen D. L., Malik K., Sherman J., Nobori T., Bader S., Nau M. M., Gazdar A. F., Minna J. D., Diaz M. O., Cancer Res. 53: 2410-2415, 1993; and Schimd M., Malicki D., Nobori T., Rosenbach M. D., Campbell K., Carson D. A., Carrera C. J., Oncogene, 17: 2669-2675, 1998.) lung cancers, gliomas (Barker F. G., Chen P., Furman F., Aldape K. D., Edwards M. S., Israel M. A., *p16 deletion and mutation analysis in human brain tumors*, J. Neurooncol., 31: 17-23, 1997; Nobori T., Karras J. G., Della Ragione F., Waltz T. A., Chen P. P., Carson D. A., Cancer Res., 51(12): 3193-3197, 1991; and Zhang H., Chen Z-H., Savarese T. M., Cancer Genet. Cytogenet., 86: 22-28, 1996.), pancreatic cancers (Chen Z-H., Zhang H., Savarese T. M., Cancer Res., 56: 1083-1090, 1996; and Caldas C., Hahn S. A., and Costa L. T., Redston, Schutte M., Seymour A. B., Weinstein C. L., Hruban R. H., Yeo C. J., Kern S. E., Nature Genetics, 8: 27-32, 1994.), bladder cancers (Stadler W. M., Olopade O. I., Urol. Res., 24: 239-244, 1996; and Stadler W. M., Steinberg G., Yang X., Hagos F., Turner C., Olopade O. I., Clin. Cancer Res., 7: 1676-1682, 2001.), melanomas (Cowan J. M., Halaban R., Francke U., J. Natl. Cancer Inst., 80: 1159-1164, 1988.), acute lymphoblastic leukemias (particularly T-cell) (Batova A., Diccianni M. B., Omura-Minamisawa M., Yu J., Carrera C. J., Bridgeman L. J., Kung F. H., Pullen J., Amylon M. D., Yu A. L., Cancer Res., 59: 1492-1497, 1999; Hori Y., Hori K., Yamada Y., Carrera C. J., Tomonaga M., Kamihira S., Carson D. A., Nobori T., Int. J. Cancer, 75: 51-56, 1998; Batova A., Diccianni M. B., Nobori T., Vu T., Yu J., Bridgeman L., Yu A. L., Blood, 88(8): 3083-3090, 1996; and M'soka T. J., Nishioka J., Taga A., Kato K., Kawasaki H., Yamada Y., Yu A., Komada Y., Nobori T., Leukemia, 14(5): 935-40, 2000.), non-Hodgkin lymphomas (Dreyling M. H., Roulston D., Bohlander S. K., Vardinan J., Olopade O. I., Genes Chromosomes Cancer, 22: 72-78, 1998.), endometrial adenocarcinomas (Wong Y. F., Chung T. K., Cheung T. H., Nobori T., Chang A. M., Gynecol. Obstet. Investig., 45: 272-276, 1998.), ovarian cancers (Bello M. J., Rey J. A., Int. J. Cancer, 45: 50-54, 1990.), breast cancers (Della Ragione F., Russo G. L., Oliva A., Mastropietro S., Mancini A., Borrelli A., Casero R. A., Iolascon A., Zappia V., Oncogene 10: 827-833, 1995; Smaaland R., Schanche J. S., Kvinnsland S., Hostmark J., Ueland P. M., Breast Cancer Res. & Treatment. 9(1): 53-9, 1987.), liver cancers (Della Ragione F., Russo G. L., Oliva A., Mastropietro S., Mancini A., Borrelli A., Casero R. A., Iolascon A., Zappia. V., Oncogene 10: 827-833, 1995), head and neck cancers (van der Riet P., Nawroz H., Hruban R. H., Corio R., Tokino K., Koch W., Sidransky D., Cancer Res., 54: 1156-1158, 1994.), rectal adenocarcinomas (Fitchen J. H., Riscoe M. K., Dana B. W., Lawrence H. J., Ferro A. J., Cancer Res. 46: 5409-5412, Oct. 1986.), renal cell carcinomas (Verdorfer I, Hobisch A., Hittmair A., Duba H-C., Bartsch G., Utermann G., Erdel M., Cancer Genet Cytogenet 111: 61-70, 1999.), mesotheliomas (Illei P. B., Rusch V., Ladanyi M., U.S. and Canadian Academy of Pathology 91st Annual Meeting Feb. 23-Mar. 1, 2002.), chondrosarcomas and soft-tissue sarcomas (van der Riet P., Nawroz H., Hruban R. H., Corio R., Tokino K., Koch W., Sidransky D., Cancer Res., 54: 1156-1158, 1994; Jagasia A. A., Block J. A., Qureshi A., Diaz M. O., Nobori T., Gitelis S., Iyer A. P., Cancer Lett., 105: 91-103, 1996; Jagasia A. A., Block J. A., Diaz M. O., Nobori T., Gitelis S., Inerot S. E., Iyer A. P., Cancer Lett., 105: 77-90, 1996; Li W. W., Cole P., Martin D. S., Banerjee D., and Bertino J. R., in press, 2002.), and osteosarcomas (Garci-Castellano J. M., Villanueva A., Healey J. H., Sowers R., Cordon-Cardo C., Huvos A., Bertino J. R., Meyers P., Gorlick R., Clin. Cancer Res. 8(3): 782-287, Mar. 2002.). The incidence of homozygous deletions of MTAP appear to be particularly high in gliomas, non-small cell lung cancers, T-cell acute lymphoblastic leukemias, pancreatic cancers, mesotheliomas, bladder cancers, osteosarcomas, and soft-tissue sarcomas (among others); various reports suggest that between 30 and 80 percent of these cancers, depending on the type, are MTAP-negative. Since the first five of these cancer types are usually very aggressive clinically, with low survival rates, it may be that MTAP-negative tumors actually account for a higher percentage of cancer deaths than their percentage incidence would suggest. For example, non-small cell lung cancers (NSCLC) account for about 12 percent of all cancers in the U.S., but for about 25 percent of all cancer deaths; since the available data suggests that about 40 percent of NSCLCs are MTAP-negative, it appears that about 10 percent of all cancer deaths may be attributable to MTAP-negative non-small cell lung cancers.

Some tumors are deficient in the enzyme MTAP not as a result of homozygous deletions but rather as a result of epigenetic silencing of the MTAP gene (either of both alleles, or of one of the alleles combined with deletion of the other). Such silencing of the MTAP gene appears to occur more frequently in certain cancer types, e.g., lymphomas, hepatocellular carcinomas, and gastric adenocarcinomas.

In certain embodiments, patients whose tumors are MTAP-deficient are identified. A number of methods known in the art may be employed. These methods include, but are not limited to, hybridization assays for homozygous deletion of the MTAP gene (see, e.g., Sambrook, J., Fritsh, E. F., and Maniatis, T. Molecular Cloning: A Laboratory Manual. 2.sup.nd, ed, Cold Spring Harbor Laboratory, Cold Spring Harbor Laboratory Press, Cold Spring Harbor, N.Y. (1989), and Current Protocols in Molecular Biology, eds. Ausubel et al, John Wiley & Sons (1992)). For example, the presence of MTAP-encoding DNA or cDNA can be determined by Southern analysis, in which total DNA from a cell or tissue sample is extracted and hybridized with a labeled probe (i.e., a complementary nucleic acid molecule), and the probe is detected. The label can, for example, be a radioisotope, a fluorescent compound, an enzyme or an enzyme co-factor, but is not so limited. MTAP-encoding nucleic acid can also be detected and/or quantified using PCR methods, gel electrophoresis, column chromatography, and immunohistochemistry, or other methods, as would be known to those skilled in the art.

Other methodologies for identifying patients with an MTAP-deficient disorder may involve detection of no transcribed polynucleotide, e.g., RNA extraction from a cell or tissue sample, followed by hybridization of a labeled probe (i.e., a complementary nucleic acid molecule) specific for the target MTAP RNA, and detection of the probe (i.e., Northern blotting). The label can be a radioisotope, a fluorescent compound, an enzyme, or an enzyme co-factor, but is not so limited. The MTAP protein can also be detected using antibody screening methods, such as Western blot analysis. Monoclonal antibodies that specifically bind to MTAP protein are disclosed in U.S. Pat. No. 7,157,551 and U.S. Pat. Application 20070280946, both of which are hereby incorporated by reference in their entirety.

Another method for identifying patients with an MTAP-deficient disorder is by screening for MTAP enzymatic activity in cell or tissue samples.

An assay for MTAP-deficient cells may comprise an assay for homozygous deletions of the MTAP-encoding gene, or for lack of mRNA and/or MTAP protein. See U.S. Pat. No. 5,942,393, which is hereby incorporated by reference in its entirety. Because identification of homozygous deletions of the MTAP-encoding gene involves the detection of low, if any, quantities of MTAP, amplification may be desirable to increase sensitivity. Detection of the MTAP-encoding gene may be carried out using a probe/primer in a polymerase chain reaction (PCR), such as anchor PCR or RACE PCR, or, alternatively, in a ligation chain reaction (LCR) (see, e.g., U.S. Pat. Nos. 4,683,195; 4,683,202 Landegran et al (1988) Science 241:1077-1080; and Nakazawa et al. (1994) Proc. Mail. Acad. Sci. USA 91:360-364, each of which is hereby incorporated by reference in its entirety). PCR and/or LCR may be used as a preliminary amplification step in conjunction with any other technique used for detecting deletion of the MTAP gene. Alternative amplification methods for amplifying any present MTAP-encoding polynucleotides include self sustained sequence replication (Guatelli, J C. et al., (1990) Proc. Natl. Acad. Sci. USA 87:1874-1878), transcriptional amplification system (Kwoh, D. Y. et al., (1989) Proc. Natl. Acad. Sci. USA 86:1173-1177), Q-Beta Replicase (Lizardi, P. M. et al. (1988) Bio-Technology 6:1197), or any other nucleic acid amplification method, followed by the detection of the amplified molecules using techniques known to those of skill in the art.

The MTAP-deficient cell samples may be obtained by biopsy or surgical extraction of portions of tumor tissue or other diseased tissue or organs from the subject. In some embodiments, the cell samples are free of healthy cells and contain only MTAP-deficient cells.

In certain embodiments methods for treatments of MTAP-positive tumors are provided. In some embodiments MTAP-positive tumors may have other defects in the MTAP pathway, i.e., the pathway leading from methylthioribose-1-phosphate (MTR-1-P) to the formation of methionine and formate (the so-called methionine salvage pathway).

When one or more enzymes in this pathway are missing or defective, methods are provided to selectively treat such tumors by the coadministration of a toxic methionine analog along with MTA, or a suitable analog of MTA, that can generate methionine in normal, proliferating cells (via their intact MTAP-pathway) so as to protect them from the toxicity of the methionine analog.

MTAP-positive tumors that may be treated using the methods described herein have not suffered homozygous deletions of the MTAP locus, but in some instances they have just one copy of the gene due to a hemizygous deletion. Because of the close proximity of the MTAP gene to the p16/p14ARF tumor suppressor gene locus, it is to be expected that hemizygous deletion of the MTAP gene may be a relatively common occurrence in tumors. In general, regions around tumor suppressor genes are frequently found to be hemizygously deleted in cancers, with the remaining intact tumor suppressor gene being inactivated by another mechanism, such as hypermethylation of its promoter or by point mutations. Indeed, hemizygous deletions of the 9p21 region encompassing the p16/p14ARF and MTAP genes have been described in a variety of human tumors, but appear to be particularly frequent in acute lymphoblastic leukemia, melanoma, ovarian cancer, glioma, pancreatic cancer, mesothelioma, head and neck cancer, breast cancer, esophageal cancer, kidney cancer, bladder cancer, chondrosarcoma, and small cell and non-small cell lung cancer. In some cases the reported loss of heterozygosity of this chromosomal region has been high; for example, one study of metastatic melanoma tumor and cell line DNAs found an 86% frequency of hemizygous loss of the 9p21 locus (J. W. Fountain, et al, Proc. Natl. Acad. Sci. USA, Vol. 89:10557-10561, 1992).

MTAP-positive tumors which are hemizygous for the MTAP gene can be treated according to the selective therapy methods described herein. In certain embodiments, wherein two or more variant alleles of the MTAP gene exist, a target cell inhibitor agent can be used. The target cell inhibitor agent may be a MTAP inhibitor. MTAP inhibitors highly specific for each of these alleles or their RNA transcripts may be designed, for example, variance-specific antisense oligonucleotides, ribozymes, or small interfering RNAs (siRNAs). In certain embodiments, specific inhibitors (e.g., small molecules or peptides) of the variant MTAP-enzymes may be designed. In certain embodiments a tumor, in an MTAP-heterozygous patient, which has lost one of the alleles may be treated with a specific inhibitor of the remaining allele, or of its expressed MTAP-protein, to render the tumor effectively MTAP-negative, and treated further with selective therapeutic regimens of competitive antagonists of adenine and/or methionine combined with MTA or a suitable analog substrate for MTAP as described herein. In such embodiments, normal cells of the subject, having both variants of the MTAP alleles, may still produce MTAP since one of their alleles is insensitive to the administered inhibitor and may be protected from the toxic adenine or methionine antagonists by the supplied MTA or analog of MTA.

Thus, the invention also features the use of small nucleic acid molecules, referred to as short interfering nucleic acid (siNA) that include, for example: microRNA (miRNA), short interfering RNA (siRNA), double-stranded RNA (dsRNA), and short hairpin RNA (shRNA) molecules to knockdown expression of proteins such as MTAP. An siNA of the invention can be unmodified or chemically-modified. An siNA of the instant invention can be chemically synthesized, expressed from a vector or enzymatically synthesized. The instant invention also features various chemically-modified synthetic short interfering nucleic acid (siNA) molecules capable of modulating gene expression or activity in cells by RNA interference (RNAi). The use of chemically-modified siNA improves various properties of native siNA molecules through, for example, increased resistance to nuclease degradation in vivo and/or through improved cellular uptake. Furthermore, siNA having multiple chemical modifications may retain its RNAi activity. The siNA molecules of the instant invention provide useful reagents and methods for a variety of therapeutic applications.

Chemically synthesizing nucleic acid molecules with modifications (base, sugar and/or phosphate) that prevent their degradation by serum ribonucleases can increase their potency (see e.g., Eckstein et al., International Publication No. WO 92/07065; Perrault et al, 1990 Nature 344, 565; Pieken et al., 1991, Science 253, 314; Usman and Cedergren, 1992, Trends in Biochem. Sci. 17, 334; Usman et al., International Publication No. WO 93/15187; and Rossi et al., International Publication No. WO 91/03162; Sproat, U.S. Pat. No. 5,334,711; and Burgin et al., supra; all of these describe various chemical modifications that can be made to the base, phosphate and/or sugar moieties of the nucleic acid molecules herein). Modifications which enhance their efficacy in cells, and removal of bases from nucleic acid molecules to shorten oligonucleotide synthesis times and reduce chemical requirements are desired. (All these publications are hereby incorporated by reference herein).

There are several examples in the art describing sugar, base and phosphate modifications that can be introduced into nucleic acid molecules with significant enhancement in their nuclease stability and efficacy. For example, oligonucleotides are modified to enhance stability and/or enhance biological activity by modification with nuclease resistant groups, for example, 2'-amino, 2'-C-allyl, 2'-fluoro, 2'-O-methyl, 2'-H, nucleotide base modifications (for a review see Usman and Cedergren, 1992, TIBS. 17, 34; Usman et al., 1994, Nucleic Acids Symp. Ser. 31, 163; Burgin et al., 1996, Biochemistry, 35, 14090). Sugar modification of nucleic acid molecules have been extensively described in the art (see Eckstein et al., International Publication PCT No. WO 92/07065; Perrault et al. Nature, 1990, 344, 565 568; Pieken et al. Science, 1991, 253, 314317; Usman and Cedergren, Trends in Biochem. Sci., 1992, 17, 334 339; Usman et al. International Publication PCT No. WO 93/15187; Sproat, U.S. Pat. No. 5,334,711 and Beigelman et al., 1995, J. Biol. Chem., 270, 25702; Beigelman et al., International PCT publication No. WO 97/26270; Beigelman et al., U.S. Pat. No. 5,716,824; Usman et al.

In one embodiment, one of the strands of the double-stranded siNA molecule comprises a nucleotide sequence that is complementary to a nucleotide sequence of a target RNA or a portion thereof, and the second strand of the double-stranded siNA molecule comprises a nucleotide sequence identical to the nucleotide sequence or a portion thereof of the targeted RNA. In another embodiment, one of the strands of the double-stranded siNA molecule comprises a nucleotide sequence that is substantially complementary to a nucleotide sequence of a target RNA or a portion thereof, and the second strand of the double-stranded siNA molecule comprises a nucleotide sequence substantially similar to the nucleotide sequence or a portion thereof of the target RNA. In another embodiment, each strand of the siNA molecule comprises about 19 to about 23 nucleotides, and each strand comprises at least about 19 nucleotides that are complementary to the nucleotides of the other strand.

In some embodiments an siNA is an shRNA, shRNA-mir, or microRNA molecule encoded by and expressed from a genomically integrated transgene or a plasmid-based expression vector. Thus, in some embodiments a molecule capable of inhibiting mRNA expression, or microRNA activity, is a transgene or plasmid-based expression vector that encodes a small-interfering nucleic acid. Such transgenes and expression vectors can employ either polymerase II or polymerase III promoters to drive expression of these shRNAs and result in functional siRNAs in cells. The former polymerase permits the use of classic protein expression strategies, including inducible and tissue-specific expression systems. In some embodiments, transgenes and expression vectors are controlled by tissue specific promoters. In other embodiments transgenes and expression vectors are controlled by inducible promoters, such as tetracycline inducible expression systems.

In another embodiment, a small interfering nucleic acid of the invention is expressed in mammalian cells using a mammalian expression vector. The recombinant mammalian expression vector may be capable of directing expression of the nucleic acid preferentially in a particular cell type (e.g., tissue-specific regulatory elements are used to express the nucleic acid). Tissue specific regulatory elements are known in the art. Non-limiting examples of suitable tissue-specific promoters include the myosin heavy chain promoter, albumin promoter, lymphoid-specific promoters, neuron specific promoters, pancreas specific promoters, and mammary gland specific promoters. Developmentally-regulated promoters are also encompassed, for example the murine hox promoters and the a-fetoprotein promoter.

Other inhibitor molecules that can be used include sense and antisense nucleic acids (single or double stranded), ribozymes, peptides, DNAzymes, peptide nucleic acids (PNAs), triple helix forming oligonucleotides, antibodies, and aptamers and modified form(s) thereof directed to sequences in gene(s), RNA transcripts, or proteins. Antisense and ribozyme suppression strategies have led to the reversal of a tumor phenotype by reducing expression of a gene product or by cleaving a mutant transcript at the site of the mutation (Carter and Lemoine Br. J. Cancer. 67(5):869-76, 1993; Lange et al., Leukemia. 6(11):1786-94, 1993; Valera et al., J. Biol. Chem. 269(46):28543-6, 1994; Dosaka-Akita et al., Am. J. Clin. Pathol. 102(5):660-4, 1994; Feng et al., Cancer Res. 55(10):2024-8, 1995; Quattrone et al., Cancer Res. 55(1):90-5, 1995; Lewin et al., Nat. Med. 4(8):967-71, 1998).

For example, neoplastic reversion was obtained using a ribozyme targeted to an H-Ras mutation in bladder carcinoma cells (Feng et al., Cancer Res. 55(10):2024-8, 1995). Ribozymes have also been proposed as a means of both inhibiting gene expression of a mutant gene and of correcting the mutant by targeted trans-splicing (Sullenger and Cech Nature 371(6498):619-22, 1994; Jones et al., Nat. Med. 2(6): 643-8, 1996). Ribozyme activity may be augmented by the use of, for example, non-specific nucleic acid binding proteins or facilitator oligonucleotides (Herschlag et al., Embo J. 13(12):2913-24, 1994; Jankowsky and Schwenzer Nucleic Acids Res. 24(3):423-9, 1996). Multitarget ribozymes (connected or shotgun) have been suggested as a means of improving efficiency of ribozymes for gene suppression (Ohkawa et al., Nucleic Acids Symp Ser. (29):121-2, 1993).

Triple helix approaches have also been investigated for sequence-specific gene suppression. Triple helix forming oligonucleotides have been found in some cases to bind in a sequence-specific manner (Postel et al., Proc. Natl. Acad. Sci. U.S.A. 88(18):8227-31, 1991; Duval-Valentin et al., Proc. Natl. Acad. Sci. U.S.A. 89(2):504-8, 1992; Hardenbol and Van Dyke Proc. Natl. Acad. Sci. U.S.A. 93(7):2811-6, 1996; Porumb et al., Cancer Res. 56(3):515-22, 1996). Similarly, peptide nucleic acids have been shown to inhibit gene expression (Hanvey et al., Antisense Res. Dev. 1(4):307-17, 1991; Knudsen and Nielson Nucleic Acids Res. 24(3):494-500, 1996; Taylor et al., Arch. Surg. 132(11):1177-83, 1997). Minor-groove binding polyamides can bind in a sequence-specific manner to DNA targets and hence may represent useful small molecules for future suppression at the DNA level (Trauger et al., Chem. Biol. 3(5):369-77, 1996). In addition, suppression has been obtained by interference at the protein level using dominant negative mutant peptides and antibodies (Herskowitz Nature 329(6136):219-22, 1987; Rimsky et al., Nature 341(6241):453-6, 1989; Wright et al., Proc. Natl. Acad. Sci. U.S.A. 86(9):3199-203, 1989). In some cases suppression strategies have led to a reduction in RNA levels without a concomitant reduction in proteins, whereas in others, reductions in RNA have been mirrored by reductions in protein.

The diverse array of suppression strategies that can be employed includes the use of DNA and/or RNA aptamers that can be selected to target, for example, a protein of interest such as MTAP. Suppression and replacement using aptamers for suppression in conjunction with a modified replacement gene and encoded protein that is refractory or partially refractory to aptamer-based suppression could be used in the invention.

Human genome variation mapping has revealed several single nucleotide polymorphisms (SNPs) in the MTAP gene that occur with high frequency. Variations in the MTAP gene that are much larger than a SNP have also been found. For instance, a study of the Japanese population discovered that there are two alleles for the MTAP gene that differ by deletion of a 14-bp region of the gene promoter (T. Nobori, et al, Jpn. J. Cancer Res. 93:369-373, 2002). The alleles occur with about equal frequency, and the incidence of heterozygosity for them is around 60%. Because of these polymorphisms of the MTAP gene (both SNPs and larger variations, as exemplified in the Japanese population) many MTAP-positive human tumors might exhibit loss-of-heterozygosity of the MTAP gene and so be amenable to treatment by the methods described herein.

In some embodiments, the MTAP gene may be inactive in quiescent cells, but may be turned on in proliferating cells, e.g., in mid to late G1, or in a different phase of the cell cycle. Polyamine biosynthesis is tied to the cell cycle, and it appears likely that expression of the MTAP gene (as well as the other genes of the MTAP-pathway) is coordinately regulated with expression of the genes of polyamine biosynthesis, such as ornithine decarboxylase (ODC) and S-adenosylmethionine decarboxylase (SAMDC); both of these genes are known to be turned on in mid to late G1 of proliferating cells.

Many solid tumor cells, such as breast, colon, lung, and ovarian tumor cells, have very long cell-cycle transit times, frequently five to ten days or longer. These long cell-cycle transit times are generally a result of prolongation of the G1 phase, rather than of the other phases (S, G2, and M) of the cell cycle. In such slowly-cycling, MTAP-positive tumor cells, wherein MTAP transcription is absent until mid to late G1, the tumors may effectively be MTAP-negative for relatively long periods of their mitotic cycle and can be treated with the methods described herein.

In some embodiments, an MTAP-positive tumor is treated with an agent which causes cell cycle arrest, e.g., in early G1, the arrest is maintained with this agent for a number of days, until substantially all previously synthesized MTAP has degraded, the cell cycle arrest is lifted (by cessation of treatment with the arresting agent) and the tumor is treated by certain selective therapeutic methods described herein, e.g., toxic adenine and/or methionine competitive antagonists along with MTA (or suitable MTA analogs) to protect normal, proliferating cells of the subject. During the early period of emergence from arrest, the tumor cells may be effectively MTAP-negative, and so should be highly sensitive to killing by selective therapeutic methods described herein. The reason for releasing the tumor cells from arrest, as the toxic analogs are applied, is that quiescent cells in general are highly insensitive to antimetabolites such as adenine analogs, a primary toxic effect of which is the disruption of DNA and RNA functioning or synthesis. It should also be noted that cells emerging from G0 tend to have considerably longer G1 phases than the same type of cell which is simply cycling; such awakened cells may therefore have quite long periods of effective MTAP-deficiency, and hence prolonged sensitivity to certain selective therapy methods described herein. Applicants have found that some toxic adenine analogs, such as 2-fluoroadenine, effectively kill human tumor cells even in very short-term assays of 6 to 12 hours; such rapidly-acting and potent adenine analogs may be of particular use in the just described method of selectively killing MTAP-positive tumor cells.

There are many ways of effecting the arrest of tumor cells, and in certain embodiments, one or more of these methods of arresting tumor cells may be employed in the just described method of selectively treating MTAP-positive tumors. Methods of causing the arrest of tumor cells include, but are not limited to: radiation treatment; deprivation of nutrients; treatment with inhibitors of angiogenesis; and treatment with various other chemical agents, such as chemotherapeutic drugs. Radiation treatment, especially at lower doses, is known to arrest, rather than kill, many tumor cells. When tumor cells are deprived of essential nutrients they usually either die or arrest. A large number of inhibitors of angiogenesis, such as angiostatin and endostatin and various inhibitors of the endothelial growth factor (VEGF) or its receptor (such as Genentech's Avastin), are under investigation to cut off the blood supply to tumors and kill or arrest them. One may also deprive certain tumors of nutrients essential to their growth by dietary restriction and/or enzymatic degradation of the nutrient in the plasma. For example, many tumor cells are known to be dependent on high levels of methionine to support growth; such tumors arrest in either G1 or G2 when deprived of sufficient methionine. There are numerous drugs, some of them in use in the cancer clinic, that are known to arrest cells at various stages of the cell cycle by interruption of one or more metabolic processes or mitotic functions.

In certain embodiments, methods for arresting MTAP-positive tumor cells, so that they may be treated by the selective therapeutic method described above, entail antagonizing a growth-signaling pathway and/or stimulating a growth-inhibitory pathway. In these embodiments, antagonizing a growth-signaling pathway for a tumor may be accomplished, depending on the tumor and its proliferation-signal transduction pathways, by antagonizing one or more growth factors or hormones on which the tumor depends for proliferation, or antagonizing (e.g., by blocking or downmodulating) the receptors for these growth factors or hormones, or antagonizing their downstream effectors (such as various intracellular kinases or phosphatases in their growth-signaling cascades), or antagonizing the upstream inducers and modulators of these growth factors or hormones and their receptors. Such modulation of hormones and their receptors has been the basis, for many years, of the clinical management of tumors originating from the reproductive organs. For example, the antiestrogen tamoxifen has long been used in the treatment or prevention of breast cancer, and the antiandrogens, flutamide and bicalutamide, have been employed in the therapy of prostate cancer. For breast cancer, other estrogen receptor antagonists, in addition to tamoxifen, such as raloxifene and faslodex, have recently been introduced into the cancer clinic. A number of aromatase inhibitors, which block production of estrogen, e.g., anastrozole (Arimidex; AstraZeneca), letrozole (Femara; Novartis), and exemestane (Aromasin; Pharmacia), have also been approved for clinical use. And for prostate cancer, drugs which block the production of testosterone, such as Abarelix, Lupron, and Zoladex, have been approved or are being investigated. Any of the aforementioned compounds and drugs may be used in the selective therapeutic methods described herein. In the past decade, an enormous amount of research has been devoted to the development of inhibitors of other, nonhormonal, growth-signaling pathways. Efforts have been particularly directed to inhibition of two members of the epidermal growth factor (EGF) receptor family, namely ErbB1 (also termed EGFR or HER1) and ErbB2 (also termed Neu or HER2). HER2 is overexpressed in a variety of solid tumors, especially breast cancer, and Herceptin (trastuzumab; Genentech), an antibody to HER2 has been approved in the treatment of this cancer. EGFR signaling appears to be involved in an even wider range of solid tumors, including cancers of the lung, pancreas, head and neck, breast, prostate, colon, stomach, ovaries, brain, kidney, and bladder. Promising inhibitors of the tyrosine kinase activity of EGFR include the small-molecule inhibitors Iressa (ZD1839; AstraZeneca) and Tarceva (OSI-774; OSI Pharmaceuticals) and the monoclonal antibodies Erbitux (C225; ImClone Systems) and ABX-EGF (AbGenix). Pfizer and GlaxoSmithKline have developed drugs which inhibit both EGFR and HER2. Considerable work is being done on antibody and small molecule inhibitors of other receptors as well as their intracellular effectors, including the platelet derived growth factor receptor (PDGF-R) and fibroblast growth factor receptor (FGF-R). Gleevec (Novartis) is a small-molecule inhibitor of the internal kinase abl, as well as of the receptor kinases c-kit and PDGF-R-beta, which in 2002 was approved in the treatment of chronic myelogenous leukemia. Other growth-signal transduction inhibitors under investigation include those targeting the RAS pathway and inhibitors of sphingosine kinase. Any one of the aforementioned compounds or drugs may be used in the selective therapeutic methods described herein.

Inhibitors of proliferation-signal transduction, such as antiestrogens and inhibitors of EGFR and HER2 tend to be mostly cytostatic rather than cytotoxic, so in general they merely halt or slow tumor progression, but do not eradicate the tumor. Thus these agents require long-term use (which can be costly) and, in any case, eventually resistance may emerge. Some of the agents that have been introduced into the cancer clinic, e.g., Herceptin and tamoxifen, have been found to have some serious long-term toxicities. Consequently, it is widely believed that these new inhibitors of growth signals will need to be combined with cytotoxic chemotherapies, if they are to have a significant impact on curing cancer rather than just prolonging life. Traditional cytotoxic chemotherapies, however, generally have significant acute and long-term toxicities. In some embodiments, inhibitors of growth-signal transduction are used to treat MTAP-positive tumors, applying said inhibitors relatively short-term to arrest MTAP-positive tumors, so as to sensitize them to certain non-toxic selective therapeutic methods described herein.

Any one of these methods for arresting tumor cells, such as radiation treatment, nutrient deprivation, angiogenesis inhibitors, antagonists of hormones or growth factors driving tumor proliferation, or other drugs that disrupt cell proliferation or metabolism, might be useful in sensitizing MTAP-positive tumors to certain selective therapeutic methods described herein and thus are all target cell inhibitor agents of the invention.

It should be noted that many of the same methods for inducing cell cycle arrest, e.g., radiation therapy, nutrient deprivation, metabolism-disrupting or proliferation-disrupting drugs (including antagonists of hormones or growth factors), may also, under some circumstances, produce not full arrest, but only a temporary inhibition of the cell cycle; that is, they may result in a lengthening of cell cycle transit rather than full cessation. Such lengthening of the cell cycle transit time, depending on which phases of the cell cycle are lengthened, and provided the delay is long enough, may also be a useful means of downmodulating MTAP levels in enzyme-positive tumor cells. Use of these various methods of growth disruption to lengthen tumor cell cycle transit, and downmodulate MTAP levels, in MTAP-positive neoplasms, are contemplated here and can be used with the therapeutic methods described herein.

In summary, there may be a number of ways of effectively treating many MTAP-positive neoplasms according to the selective therapeutic methods described herein. In certain embodiments, other ways of rendering MTAP-positive neoplasms susceptible to the selective therapeutic methods described herein comprise directly, and selectively, delivering inhibitors of the MTAP enzyme (or of its gene or mRNA) to MTAP-positive tumors, for example through targeting with tumor-specific antibodies, peptides, liposomes, or viral-vectors, so as to render these tumors MTAP-negative.

The vast majority of cells in mammals are not proliferating, but rather are quiescent. Many types of viruses infect quiescent cells, either exclusively or primarily.

In some embodiments, wherein quiescent mammalian cells are MTAP-deficient, any virus infecting such a cell may be treated by certain selective therapeutic methods described herein, wherein viral-induction of subject enzymes does not include MTAP. In some embodiments, wherein a virus induces full host cell proliferation, or at least induces a repertoire of host enzymes including MTAP, the virus is treated by certain selective methods described herein, wherein the initial stages of the life-cycle of such viruses, after cell penetration, but before induction of host cell proliferation or of cellular MTAP, involves some synthesis of viral protein and/or viral nucleic acids, either or both of these viral syntheses may be disrupted by appropriate adenine or methionine competitive antagonists. Virus infections that may be treatable according to these methods include, but are not limited to, human immunodeficiency virus, hepatitis viruses (such as hepatitis B and C), herpes simplex viruses, cytomegaloviruses, and dengue virus.

Other pathogens that are treatable according to these embodiments may include rickettsiae and chlamydiae, wherein the status of quiescent infected cells is MTAP-negative. In certain embodiments, wherein such pathogens do induce host cell proliferation, or at least expression of the MTAP enzyme, said pathogens may be selectively treatable according to certain methods described herein, wherein an essential parasite metabolic or reproductive function which precedes the induction of cellular MTAP and which is inhibitable by an adenine or methionine competitive antagonist is present.

Many prokaryotes and some lower eukaryotes, particularly protozoa, catabolize MTA, as well as S-adenosylhomocysteine (SAH), in a manner distinct from that of mammals. These microorganisms utilize a single nucleosidase (denoted MTA/SAH nucleosidase) to hydrolyze the glycosidic bond of both nucleosides to yield adenine and the corresponding thiopentose, i.e., methylthioribose (MTR) or S-ribosyl-homocysteine, respectively. An additional enzyme, methylthioribose kinase (MTR kinase) is also generally present and converts the MTR, derived from MTA, to methylthioribose-1-phosphate, which is subsequently recycled into methionine via a pathway similar to that in mammalian cells. In contrast, in the cells of mammals, MTA and SAH are catabolized by two distinct enzymes: MTAP and SAH hydrolase. Among the microorganisms which have been reported to utilize MTA/SAH nucleosidase and MTR kinase, rather than MTAP, to recycle the adenine and methylthio groups of MTA, are the following: *Enterobacter aerogenes, Enterobacter cloacae, Klebsiella pneumoniae, Ochromonas malhamensis, Giardia lamblia, Plasmodium falciparum, Entamoeba invadens, Candida albicans, Escherichia coli* (which has a nucleosidase but may be lacking MTR kinase), and *Staphylococcus aureus* (Riscoe M. K., Ferro A. J., Fitchen J. H., Parasitology Today, 5(10):330-333, 1989; and Sufrin J. R., Bacchi C. J., Porter C. W., Nathan H, Spiess A. J., Yarlett N., U.S. Pat. No. 5,180,714). In some embodiments any pathogenic organism which depends on alternative pathways for the salvage of the adenine and methionine consumed in polyamine biosynthesis is sensitized to be treated according to certain selective therapy methods described herein, wherein an inhibitor is administered that is specific for the MTA/SAH nucleosidase, or the MTR kinase, of the pathogen so that the organism is rendered incapable of generating adenine and/or methionine from the MTA (or suitable MTA analog) that serves to protect the critical cells of the subject from the toxic adenine or methionine competitive antagonist. Powerful, and specific, inhibitors of the MTA/SAH nucleosidase of *E. coli* which may be used in these embodiments have been reported in the literature (Della Ragione F., Porcelli M., Carteni-Farina M., Zappia V., Biochem. J. 232:335-341, 1985; and Cornell K. A., Swartz W. E., Barry R. D, Riscoe M. K., Biochem. Biophys. Res. Comm. 228:724-732, 1996). Other selective and potent inhibitors of the MTA/SAH nucleosidase, and of the MTR kinase, present in various pathogenic microbes may be developed by methods well-known in the art and could be used according to the methods provided herein.

Many other prokaryotes, protozoa, and other lower eukaryotes recycle the adenine and methylthio moieties of MTA in a manner very similar to that of mammals and other higher organisms, i.e., via an MTA phosphorylase. However, the phosphorylases in these organisms, which have been reported on in the literature, have all exhibited very significant differences from the mammalian MTAP in terms of substrate specificities and enzyme activity. In certain embodiments, infections of prokaryotes, protozoa and other lower eukaryotes are treated according to methods provided herein, wherein MTAPs of lower organisms differ sufficiently in structure from their mammalian counterpart that they are affected by specific inhibitors that do not affect mammalian MTAP, administering such inhibitors that are specific for the microbial but not the mammalian MTAP, to render such MTAP-containing pathogenic microorganisms sensitive to certain selective therapy methods described herein. Among the pathogenic microorganisms, of major significance to human health, which have been found to possess an MTA phosphorylase that may be treated by the methods described herein, are members of the genus *Trypanosome*, of the genus *Leishmania*, and of the genus *Trichomonas*.

Parasitic helminths are the cause of severe human illnesses, such as schistosomiasis and fascioliasis, which affect the health of hundreds of millions of people worldwide. An MTAP or MTA/SAH hydrolase comparable to that of other lower eukaryotes has not yet been reported in parasitic helminths. As a group, the parasitic helminths may lack either of these enzymes, for it has been suggested that they do not have an active biosynthetic pathway for polyamine production and instead depend on uptake of polyamines from their subjects (Sharma V., Tekwani B. L., Saxena J. K., Gupta S., Katiyar J. C., Chatterjee R. K., Ghatak S., Shukla O. P., Experimental Parasitology 72:15-23, 1991; and Tekwani B. L., Mishra M., Chatterjee R. K., Int. J. Biochem. and Cell Biol. 27:851-855, 1995). However, many helminths may have other enzymes which can degrade MTA. For instance, in the trematode Fasciola hepatica, two enzymes that act on MTA have been isolated: an adenosine phosphorylase and an adenosine deaminase, both of broad specificity. The phosphorylase can generate adenine from MTA (and presumably many MTA analogs), whereas the deaminase cannot. In certain embodiments, wherein the deaminase activity predominates, trematodes or other helminths carrying this deaminase may be selectively treatable by certain methods described herein, wherein the deaminated MTA (or MTA analog) cannot generate protective adenine. In embodiments wherein the phosphorylase activity towards MTA (or MTA analogs) is comparable or greater than that of the deaminase, a specific inhibitor of the phosphorylase is administered in order to treat a helminthic infection according to certain methods described herein.

In certain embodiments, wherein fungi actively synthesize polyamines and do possess either an MTA/SAH hydrolase or an MTAP (e.g., *Candida albicans* possesses the former, whereas *Saccharomyces cerevisiae* displays the latter enzyme) infections caused by pathogenic fungi can be treated by certain selective methods described herein by co-administering a drug which specifically inhibits the MTA-degrading enzyme of the fungus. In certain embodiments, wherein a fungus, such as *Aspergillus oryzae*, possesses a non-specific adenosine deaminase that converts MTA to the corresponding inosine derivative, infections caused by these fungi are selectively treated by certain methods described herein utilizing toxic adenine antagonists and MTA (or suitable MTA analog) without administering a sensitizing agent.

In certain embodiments, wherein pathogens such as bacteria, protozoa, fungi, and helminths exhibit significant differences, from mammalian cells, in their transport mechanisms for nucleosides, pathogens are sensitized to certain selective therapy methods described herein, depending on the mechanism and carriers responsible for nucleoside transport into a pathogen, a specific inhibitor that will prevent uptake of MTA compounds will be administered. In such embodiments, prevention of the uptake of MTA compounds into the pathogen obviates the need for any direct inhibition of the MTA-degrading pathway within the pathogen.

There are a number of other ways in which tumors and infectious pathogens (such as viruses, bacteria, protozoa, fungi, and helminths) may obtain adenine nucleotides and methionine, in addition to salvage from MTA. In certain embodiments, wherein such target cells in mammals are treated with toxic adenine analogs and/or methionine analogs, in accordance with certain methods described herein, the selective therapy is potentiated by inhibiting one or more of these alternative sources of adenine nucleotides and methionine.

For example, in mammalian cells there are three sources of adenine nucleotides, in addition to the MTAP/APRT-coupled pathway (as indicated in FIG. 2). The first is production of AMP through the twelve-step pathway of de novo purine biosynthesis.

The last two steps of this pathway, commencing at the so-called IMP-branch point, are: the synthesis of adenylosuccinate from inosinate (IMP) and aspartate, catalyzed by adenylosuccinate synthetase (ASS), followed by the removal of fumarate, by the enzyme adenylosuccinate lyase (ASL), to produce AMP.

The second source of adenine nucleotides is through the salvage of hypoxanthine. Hypoxanthine is available to cells both exogenously (i.e., from the mammalian circulation, where it is present in a concentration of between 1 and 10 $\mu$M) and endogenously, as a product of the degradation of cellular purine nucleotides. This hypoxanthine is salvaged to IMP by the enzyme HGPRT, and the IMP so produced may be converted to AMP via the sequential action of the enzymes ASS and ASL (as described above). It should be noted that adenine, in contrast to hypoxanthine, is normally not available from the human circulation in any significant quantity, as its concentration is generally less than 20 nM.

The third source of AMP is through the phosphorylation of adenosine by the enzyme adenosine kinase (AK). Cellular adenosine is produced by the hydrolysis of S-adenosylhomocysteine (SAH), the latter compound being formed in the "activated methyl cycle" when the methyl group of SAM is transferred to an acceptor. Adenosine is present in serum at only relatively low levels—generally at a concentration between 10 and 150 nM.

Specific and potent inhibitors of all three of these additional sources of adenine nucleotides are well known in the art and any of these inhibitors may be used with certain selective therapeutic methods described herein. For instance, the glutamine analogs azaserine and 6-diazo-5-oxo-L-norleucine (DON), and the antifolates methotrexate, aminopterin, and lometrexol are all excellent inhibitors of de novo purine synthesis. Hadacidin and L-alanosine are excellent inhibitors of adenylosuccinate synthetase (ASS), and 5'-iodotubercidin and 5'-amino-5'-deoxyadenosine are very good inhibitors of adenosine kinase. Also known in the art are effective inhibitors of the transport of hypoxanthine and of adenosine into mammalian cells, and serum hypoxanthine levels can be reduced by restricting dietary intake of purines.

As with adenine nucleotides, there are several sources of methionine available to mammalian cells, in addition to its production through the MTAP-pathway (see FIG. 2). Methionine is available from the mammalian circulation. In humans, the serum concentration is around 20 $\mu$M. It is also available endogenously from the turnover of intracellular proteins and it is available through the transmethylation of homocysteine by the enzyme methionine synthase. Homocysteine is produced endogenously through the "activated methyl cycle"—it is the co-product, along with adenosine, of the hydrolysis of SAH; homocysteine, like methionine, can also be taken up from the mammalian circulation, where its concentration is around 10 $\mu$M. Direct inhibitors of methionine synthase are known in the art, as well as antagonists of the two cofactors that the enzyme requires: its coenzyme methylcobalamin and N5-methyltetrahydrofolate (the donor of the methyl group to cobalamin) all of which can be used with certain selective therapeutic methods described herein. For instance, both methotrexate and aminopterin inhibit methionine synthase through their disruption, as inhibitors of dihydrofolate reductase, of the production of reduced folates. The availability of serum methionine to mammalian cells may be reduced, in some embodiments, by dietary restriction of the amino acid, preferably combined with dietary restriction also of choline and homocysteine. It may also be reduced by intravenous administration of a methionine-degrading enzyme, such as recombinant L-methioninase (derived, e.g., from E. coli).

In certain embodiments, the selective therapeutic methods described herein are combined with one or more of the above described methods for reducing the availability of adenine nucleotides and/or methionine to the tumor cells; this may significantly potentiate said selective therapeutic methods for the treatment of tumors in mammals, and for the treatment of various infectious pathogens in mammals, such as viruses, bacteria, protozoa, fungi, and helminths.

In certain embodiments, the selective therapeutic methods described herein are combined with one or more of the above-described methods of reducing the availability of adenine nucleotides and/or methionine to tumors (or other target cells) so as to potentiate said selective therapeutic methods, wherein such a combination reduces the risk of resistance emerging in a target cell and wherein, by increasing the systemic demand in the subject for purine nucleotides and methionine, any potential for metabolic cooperation between tumor (or other target cell) and normal, MTAP-positive cells of the subject, is minimized or eliminated.

In certain embodiments, wherein excess adenine or methionine is excreted in sufficient quantities by MTAP-positive cells of the treated subject to significantly reduce the effectiveness of certain selective therapy methods described herein, various means may be employed to minimize or eliminate this problem. Such means include, but are not limited to: administering an adenine-degrading enzyme or a methionine-degrading enzyme, such as a recombinant adenase or a recombinant methioninase, derived e.g., from a microorganism; administering an agent which increases the renal excretion of adenine or methionine; directly blocking the uptake of serum adenine or methionine into cells by administering an inhibitor of adenine or methionine transport; increasing the systemic demand for purines or methionine, by restricting dietary intake of purines or methionine, or by administering inhibitors of the synthesis of adenine nucleotides or of methionine (such as those described above).

In certain embodiments, certain selective therapy methods described herein may be combined with the antifolate, methotrexate, to potentiate said methods. Methotrexate inhibits not only de novo purine synthesis (DNPS), but the synthesis of methionine as well (through its depletion of the reduced folate cofactor required by the enzyme methionine synthase). Methotrexate, by its general inhibition of DNPS, has also been shown to reduce significantly the level of serum hypoxanthine, and it also appears to inhibit the transport of methionine into cells. In these embodiments, methotrexate, when used in combination with adenine and methionine antagonists, may provide a particularly strong potentiation of the selective therapy methods described herein, and wherein thymidine may be added to the drug regimen to overcome the nonspecific, methotrexate-induced inhibition of thymidylate synthesis.

Pathogenic prokaryotes and lower eukaryotes, such as protozoa, fungi, and helminths, generally have mechanisms for providing their purine and amino acid requirements that are quite distinct from those in mammalian cells. For instance, it appears that all parasitic helminths and many (if not all) parasitic protozoa are completely lacking in a pathway for the de novo synthesis of purines. They rely instead on obtaining purines from their subject, and have elaborate purine and purine nucleoside transport and salvage pathways to efficiently accomplish this. Parasitic helminths also obtain most (or perhaps all) of their amino acids from their subjects by excreting proteases which break down host proteins. In certain embodiments, selective inhibitors of the aforementioned enzymes and transport molecules are employed that deprive pathogenic organisms of purine nucleotides and/or methionine wherein said inhibitors potentiate the selective therapy methods described herein.

In certain embodiments, wherein the selective therapy methods described herein utilize, instead of toxic adenine analogs or methionine analogs, or in addition to, competitive antagonists of adenine drawn from the broader class of analog substrates of the other mammalian phosphoribosyltransferases (HGPRT, OPRT, NAPRT, NAMPRT, QPRT), a method for reducing the availability to the target cell of the corresponding natural substrates for these PRTs, or the availability of the natural nucleotides which these PRTs produce, may be employed to potentiate the therapeutic methods. In some embodiments, wherein toxic analog substrates of the purine salvage enzyme HGPRT are utilized, many of the same potentiating methods discussed above, for example, inhibitors of de novo purine synthesis, or of hypoxanthine transport, may be used. In other embodiments, other methods of potentiating said selective therapies are indicated with this broader class of adenine competitive antagonists which are substrates of the other mammalian phosphoribosyltransferases.

In some embodiments, certain selective therapeutic methods based on upregulating the MTAP-pathway may also provide selective protection of host cells from competitive antagonists of intermediate products of the pathway, e.g., from toxic analogs of MTR-1-P or of 2-keto-4-methylthiobutyrate (KMTB) or selective protection of host cells from competitive antagonists of derivatives of the pathway, in particular from competitive antagonists of purine nucleosides or nucleotides, all of which may be derived from the adenine product of the MTAP-pathway through nucleoside and nucleotide interconversions. In these embodiments, the purine nucleoside or nucleotide may be regarded as derived from an extended metabolic pathway beginning with the MTAP-catalyzed cleavage of MTA to adenine, followed by the APRT-salvage pathway and one or more pathways of purine nucleotide or nucleoside interconversions.

The methods described herein may also be useful in the ex vivo treatment of graft tissues, for example, during transplantation. The methods described herein could be applied ex vivo to the graft tissue, which may eliminate a known or suspected target cell in the graft tissue (for example, cancer cells, viruses, bacteria, protozoa, mycoplasmas, or fungi) before the graft tissue is transplanted into the recipient. Graft tissues include, but are not limited to, those cells, tissues, or organs obtained from a donor for transplantation into a recipient, wherein the donor may be a human or animal and the recipient may be the same as the donor or another subject. The donor may be a living subject, a fetus, or a recently deceased subject. The graft cells, tissues, and organs may include, but are not limited to: stem cells, whole blood, blood cells or other blood components or fractions; bone marrow cells; placental cells; sperm and ova; reproductive organs; heart, lung, kidney, liver, brain and other nervous system tissues, skin, skeletal muscle, and corneas; as well as other organs, tissues, and cells. The graft tissues in some embodiments may also include cells, tissues, and organs which have been grown or expanded ex vivo (e.g., in cell culture) before transplantation into the recipient.

The dosage and timing of administration of toxic agents and protective agents of the instant invention will depend upon the disease being treated, the particular agents used, their method of administration, and on patient-specific factors. It will be apparent to those skilled in the art how to determine, by routine experimentation, the dosage and timing of the administration of a particular toxic agent and protective agent.

Methods of administering the therapeutic agents of the present invention will vary depending upon the specific agents used and the disease being treated, as would either be known to those skilled in the art or can be established by routine experimentation using methods commonly employed in the art. Dependent upon these factors, the agents may be administered orally or parenterally. Parenteral modes of administration include intravenous, intramuscular, subcutaneous, intradermal, intraperitoneal, intralesional, intrapleural, intrathecal, intra-cerebral, intra-arterial, and into lymphatic vessels or nodes and to bone or bone marrow. The therapeutic agents of the invention may also be administered topically or transdermally, buccally or sublingually, or by a nasal, pulmonary, vaginal, urethral, or anal route. In some embodiments, toxic agents and protective agents may be administered by different routes. For example, in the case of a neoplasm, a competitive antagonist may be injected directly into the tumor or tissues immediately surrounding the tumor, or into an anatomic compartment containing it or a blood vessel supplying it, while the protective agent may be administered systemically (e.g., orally or by intravenous injection).

The therapeutic agents described herein may be administered alone, or may be formulated as standard pharmaceutical compositions in solid, semi-solid, or liquid dosage forms. Such forms include, for example, tablets, pills, capsules, suppositories, powders, liquids, or suspensions, preferably in unit dosage form suitable for single administration of a precise dosage. The compositions will include an effective amount of the therapeutic agent in combination with a pharmaceutically acceptable carrier or excipient and, in addition, may include other medicinal agents, pharmaceutical agents, carriers, or diluents. The pharmaceutical formulation described herein will depend on the particular agent and its intended application and mode of administration.

A protective agent may be administered either before or after, or substantially concurrently, with a competitive antagonist, so as to protect the host cells from the toxic effects of the latter drug. In some embodiments a protective agent may be administered at a time distinctly prior to administration of a competitive antagonist. This prior administration of a protective agent would result in a prior increase in the intracellular pool of the metabolite in the host cells which may attenuate the toxicity of the competitive antagonist of the cellular metabolite to a significantly greater degree than that attained with simultaneous administration of the two drugs. Such a prior expansion in the intracellular pool of the metabolite may potentiate the competitive inhibition, by the cellular metabolite, of the toxic action of the competitive antagonist; it may, as well, inhibit transport of the competitive antagonist into the host cells, especially in circumstances wherein the cellular metabolite and the competitive antagonist share a common transport mechanism (e.g., a common transport carrier).

Administration of a protective agent may occur some time after a drug and may still provide sufficient protection for the host cells. The effectiveness of administration of a protective agent after a drug may, in some embodiments, depend on the methods of administration of the two agents and their in vivo pharmacokinetics.

When the two agents, protective agent and competitive antagonist, are concurrently administered, the two may in certain circumstances be mixed or formulated prior to administration so that there is a single composition to be administered (e.g., as an oral tablet or injectable liquid). Similarly, in certain embodiments, more than one competitive antagonist or more than one protective agent may be utilized, and in some of these instances it may be preferable that multiple competitive antagonists, or multiple protective agents, be formulated as a single composition.

Agents useful in certain methods described herein may include any pharmaceutically acceptable salts, prodrugs, solvates or pharmaceutically active metabolites thereof. As used herein, a "prodrug" is a compound that may be converted under physiological conditions or by solvolysis to a specified compound or to a pharmaceutically acceptable salt of such compound. An "active metabolite" is a pharmacologically active product produced through metabolism of a specified compound or salt thereof. Prodrugs and active metabolites of a compound may be routinely identified using techniques known in the art. See, e.g., Bertolini et al., J. Med. Chem. (1997), 40:2011-2016; Shan et al., J. Pharm. Sci. (1997), 86 (7):765-767; Bagshawe, Drug Dev. Res. (1995), 34:220-230; Bodor, Advances in Drug Res. (1984), 13:224-331; Bundgaard, Design of Prodrugs (Elsevier Press 1985); Larsen, Design and Application of Prodrugs, Drug Design and Development (Krogsgaard-Larsen et al. eds., Harwood Academic Publishers, 1991); Dear et al., J. Chromatogr. B (2000), 748: 281-293; Spraul et al., J. Pharmaceutical & Biomedical Analysis (1992), 10 (8):601-605; and Prox et al., Xenobiol. (1992), 3 (2):103-112. A "pharmaceutically acceptable salt" is intended to mean a salt that retains the biological effectiveness of the free acids and bases of a specified compound and that is not biologically or otherwise undesirable. Examples of pharmaceutically acceptable salts include sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, (hydroxybutyrates, glycollates, tartrates, methane-sulfonates (mesylates), propane-sulfonates, naphthalene-1-sulfonates, naphthalene-2-sulfonates, and mandelates. A "solvate" is intended to mean a pharmaceutically acceptable solvate form of a specified compound that retains the biological effectiveness of such compound. Examples of solvates include compounds of the invention in combination with water, isopropanol, ethanol, methanol, DMSO, ethyl acetate, acetic acid, or ethanolamine.

In the case of compounds, salts, or solvates that are solids, it is understood by those skilled in the art that the useful compounds, salts, and solvates of the invention may exist in different crystal forms, all of which are intended to be within the scope of the present invention.

Some of the compounds of the present invention may have chiral centers and therefore exist in different enantiomeric forms. All such optical isomers and stereoisomers of said compounds, as well as racemic and non-racemic mixtures of said optical isomers and stereoisomers, are intended to be within the scope of the present invention. It is also possible that some compounds of the present invention may exist in different tautomeric forms. All tautomers of compounds of the present invention are included within the scope of the present invention.

For any compound described herein the "effective amount" can be initially determined from animal models, or can initially be determined in vitro. A therapeutically effective dose can also be determined from data for compounds which are known to exhibit similar pharmacological activities.

In certain embodiments a "maximum rescuable dose" of the various adenine and methionine competitive antagonists of therapeutic interest is established for the selective therapeutic methods described herein. This may be investigated initially in vitro, and/or in an animal model, such as a mouse model, or any other animal model known in the art, and subsequently in man, e.g., in clinical trial studies. In certain embodiments, the "maximum rescuable dose" for each antagonist is established by the following: for each protective agent (e.g., an MTA compound), a maximum tolerated dose of the protective agent is established through a standard dose-escalation study; then for each adenine or methionine antagonist of therapeutic interest, a dose-escalation study establishes a maximum rescuable dose of the antagonist when it is co-administered with the maximum tolerated dose of the protective agent. A "maximum tolerated dose" of an agent, as used herein, means the highest dose that can be administered to a subject without significant harm to the subject. The "maximume rescuable dose" of a competitive antagonist will, in general, be dependent on such factors as the modes and timing of the administration of the two agents, competitive antagonist and protective agent.

Delivery of multiple doses of the agents, competitive antagonists of adenine or methionine, and MTA compound, are contemplated. Multiple doses may be administered in a single day, as well as over several days, weeks, or months. In the case of such multiple dosing, the "maximum rescuable dosing" of a competitive antagonist, and the "maximum tolerated dosing" of the protective agent may be established first in an animal model, and then in a human (or other vertebrate) subject, by methods analogous to that used to establish a "maximal rescuable dose" of a competitive antagonist and a "maximum tolerated dose" of a MTA compound.

These maximum rescuable doses, or dosing, of competitive antagonists of adenine or methionine, can serve as a guide for dosing determinations in the treatment of various diseases as described herein.

A person of skill in the art would know how to define and determine certain parameters critical to the effective treatment of diseases according to the methods of the instant invention, such as mode of administration of the agents, frequency and duration of the dosing, precise interval of drug sequencing (e.g., the protective agent can be given concurrently with the toxic adenine or methionine antagonist, or at some interval prior to dosing with the toxic antagonist) as well as the acceptable minimization of the acute and long-term toxicities of an antagonist.

In each clinical case under treatment, the dosage and timing of administration of the therapeutic and protective agents (e.g., adenine or methionine antagonists, and MTA compounds) will depend upon thedisease being treated, the particular agents used, their method of administration, and also on patient-specific factors. Combined with the teachings provided herein, by choosing among the various active compounds and weighing factors such as potency, relative bio-availability, patient body weight, severity of adverse side-effects and preferred mode of administration, an effective treatment regimen can be planned which does not cause substantial toxicity and yet is entirely effective to treat the particular subject. It will be apparent to those skilled in the art how to determine the dosage and scheduling of the administration of a particular therapeutic agent and protective agent as described herein.

Based on the results of in vitro tissue culture experiments by Applicants on the protection of MTAP-positive cells from toxic adenine and methionine analogs, for certain embodiments, in vivo application of certain selective therapeutic methods described herein to the treatment of human neoplasms, dosages resulting in plasma concentrations within the following ranges may be effectively employed: for 2-fluoroadenine, 0.1 to 10 µM; for 6-methylpurine, 0.5 to 100 µM; for 2,6-diaminopurine, 10 to 1000 µM; for ethionine, 10 to 1000 µM; for selenomethionine, 10 to 1000 µM; however, lower and higher concentrations of these agents may also be employed. Plasma concentrations of MTA which may confer sufficient protection of host cells from the toxicity of the aforementioned plasma concentrations of the adenine and methionine analogs may be within the range of 1 to 250 µM, and preferably in the range of 5-100 µM; however, lower and higher concentrations may also be employed. Plasma concentrations of 5'-dAdo which may confer sufficient protection of host cells from the toxicity of the aforementioned plasma concentrations of the adenine analogs may be in the range of 1 to 500 µM, and preferably in the range of 5-200 µM; however, lower and higher concentrations may also be employed. The precise plasma concentration of MTA or 5'-dAdo required to effectively neutralize the toxic effects of the adenine or methionine analogs will depend on the particular analog employed and the dosage, timing, and method of its administration. The applied dose can be adjusted based on the relative bioavailability and potency of the administered compound. Adjusting the dose to achieve maximal efficacy based on the methods described above and other methods as are well-known in the art is well within the capabilities of the ordinarily skilled artisan.

In some instances, when the agents of the invention are administered with other cancer medicaments, a sub-therapeutic dosage of either the agents described herein or the other cancer medicaments, or a sub-therapeutic dosage of both, is used in the treatment of a subject having, or at risk of developing, cancer. When the two classes of drugs are used together, the cancer medicament may be administered in a sub-therapeutic dose to produce a desirable therapeutic result. A "sub-therapeutic dose" as used herein refers to a dosage which is less than that dosage which would produce a therapeutic result in the subject if administered in the absence of the other agent. Thus, the sub-therapeutic dose of a cancer medicament is one which would not produce the desired therapeutic result in the subject in the absence of the administration of the agents of the invention. Therapeutic doses of cancer medicaments are well known in the field of medicine for the treatment of cancer. These dosages have been extensively described in references such as Remington's Pharmaceutical Sciences, 18th ed., 1990; as well as many other medical references relied upon by the medical profession as guidance for the treatment of cancer.

The compounds of the invention can be administered by any ordinary route for administering medications. Depending upon the type of disease to be treated, and the agents used, compounds of the invention may be delivered locally or systemically. They may be ingested, injected, inhaled, infused, applied topically, or delivered by other means such as by a transdermal patch or a suppository. Preferred routes of administration include, but are not limited to: oral, intravenous, intra-arterial, intramuscular, subcutaneous, intradermal, transdermal, intranasal, intratracheal, intrathecal, intracerebral, intrapleural, intraperitoneal, intralesional, sublingual, buccal, ocular, vaginal, urethral, rectal, topical, and into lymphatic vessels or nodes and to bone or bone marrow. For use in therapy, an effective amount of the compounds of the invention can be administered to a subject by any mode that delivers the agents of the invention to the affected organ or tissue. "Administering" the pharmaceutical composition of the present invention may be accomplished by any means known to the skilled artisan. Parenteral modes of administration include intravenous, intramuscular, subcutaneous, intradermal, intraperitoneal, intralesional, intrapleural, intrathecal, intra-cerebral, intra-arterial, and into lymphatic vessels or nodes and to bone or bone marrow. The therapeutic agents of the invention may also be administered topically or transdermally, buccally or sublingually, or by a nasal, pulmonary, vaginal, urethral, or anal route.

According to the methods of the invention, the agents described herein may be administered in a pharmaceutical composition. In general, a pharmaceutical composition comprises the described herein and a pharmaceutically-acceptable carrier. Pharmaceutically-acceptable carriers are well-known to those of ordinary skill in the art. As used herein, a pharmaceutically-acceptable carrier means a non-toxic material that does not interfere with the effectiveness of the biological activity of the active ingredients.

Pharmaceutically acceptable carriers include diluents, fillers, salts, buffers, stabilizers, solubilizers and other materials which are well-known in the art. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

The agents described herein may be formulated into preparations in solid, semi-solid, liquid or gaseous forms such as tablets, capsules, powders, granules, ointments, solutions, depositories, inhalants and injections, and usual ways for oral, parenteral or surgical administration. The invention also embraces pharmaceutical compositions which are formulated for local administration, such as by implants.

Compositions suitable for oral administration may be presented as discrete units, such as capsules, tablets, lozenges, each containing a predetermined amount of the active agent. Other compositions include suspensions in aqueous liquids or non-aqueous liquids such as a syrup, elixir or an emulsion.

The agents described herein may be administered directly to a tissue. Preferably, the tissue is one in which the target cells are found. Alternatively, the tissue is one in which the target cell is likely to arise. Direct tissue administration may be achieved by direct injection. The agents may be administered once, or alternatively they may be administered in a plurality of administrations. If administered multiple times, the agents may be administered via different routes. For example, the first (or the first few) administrations may be made directly into the affected tissue while later administrations may be systemic.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers for neutralizing internal acid conditions or may be administered without any carriers.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

When the compounds described herein are used therapeutically, in certain embodiments a desirable route of administration may be by pulmonary aerosol. Techniques for preparing aerosol delivery systems containing compounds are well known to those of skill in the art. Inhaled medications are preferred in some embodiments because of the direct delivery to the lung, particularly wherein the disease being treated is lung cancer. Several types of metered dose inhalers are regularly used for administration by inhalation. These types of devices include metered dose inhalers (MDI), breath-actuated MDI, dry powder inhaler (DPI), spacer/holding chambers in combination with MDI, and nebulizers. For administration by inhalation, the compounds for use according to the present invention may, for instance, be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch. Techniques for preparing aerosol delivery systems are well known to those of skill in the art. Generally, such systems should utilize components which will not significantly impair the biological properties of the active agent (see, for example, Sciarra and Cutie, "Aerosols," in *Remington's Pharmaceutical Sciences,* 18th edition, 1990, pp 1694-1712; incorporated by reference). Those of skill in the art can readily determine the various parameters and conditions for producing aerosols without resort to undue experimentation.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antifungals, anti-oxidants, chelating agents, and inert gases and the like.

In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of compounds. In yet other embodiments, the preferred vehicle is a biocompatible microparticle or implant that is suitable for implantation into the mammalian recipient. Exemplary bioerodible implants that are useful in accordance with this method are described in PCT International Application No. PCT/US/03307 (Publication No. WO 95/24929, entitled "Polymeric Gene Delivery System", claiming priority to U.S. patent application Ser. No. 213,668, filed Mar. 15, 1994). PCT/US/0307 describes a biocompatible, preferably biodegradable polymeric matrix for containing a biological macromolecule. The polymeric matrix may be used to achieve sustained release of the agent in a subject. In accordance with one aspect of the instant invention, the agent described herein may be encapsulated or dispersed within the biocompatible, preferably biodegradable polymeric matrix disclosed in PCT/US/03307. The polymeric matrix preferably is in the form of a microparticle such as a microsphere (wherein the agent is dispersed throughout a solid polymeric matrix) or a microcapsule (wherein the agent is stored in the core of a polymeric shell). Other forms of the polymeric matrix for containing the agent include films, coatings, gels, implants, and stents. The size and composition of the polymeric matrix device is selected to result in favorable release kinetics in the tissue into which the matrix device is implanted. The size of the polymeric matrix device further is selected according to the method of delivery which is to be used, typically injection into a tissue or administration of a suspension by aerosol into the nasal and/or pulmonary areas. The polymeric matrix composition can be selected to have both favorable degradation rates and also to be formed of a material which is bioadhesive, to further increase the effectiveness of transfer when the device is administered to a vascular, pulmonary, or other surface. The matrix composition also can be selected not to degrade, but rather, to release by diffusion over an extended period of time.

Both non-biodegradable and biodegradable polymeric matrices can be used to deliver the agents of the invention to the subject. Biodegradable matrices are preferred. Such polymers may be natural or synthetic polymers. Synthetic polymers are prefaced. The polymer is selected based on the period of time over which release is desired, generally in the order of a few hours to a year or longer. Typically, release over a period ranging from between a few hours and three to twelve months is most desirable. The polymer optionally is in the form of a hydrogel that can absorb up to about 90% of its weight in water and further, optionally is cross-linked with multivalent ions or other polymers.

In general, the agents of the invention may be delivered using the bioerodible implant by way of diffusion, or more preferably, by degradation of the polymeric matrix. Exemplary synthetic polymers which can be used to form the biodegradable delivery system include: polyamides, polycarbonates, polyalkylenes, polyalkylene glycols, polyalkylene oxides, polyalkylene terepthalates, polyvinyl alcohols, polyvinyl ethers, polyvinyl esters, poly-vinyl halides, polyvinylpyrrolidone, polyglycolides, polysiloxanes, polyurethanes and co-polymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), polyvinyl acetate, poly vinyl chloride, polystyrene and polyvinylpyrrolidone.

Examples of non-biodegradable polymers include ethylene vinyl acetate, poly(meth)acrylic acid, polyamides, copolymers and mixtures thereof.

Examples of biodegradable polymers include synthetic polymers such as polymers of lactic acid and glycolic acid, polyanhydrides, poly(ortho)esters, polyurethanes, poly(butic acid), poly(valeric acid), and poly(lactide-cocaprolactone), and natural polymers such as alginate and other polysaccharides including dextran and cellulose, collagen, chemical derivatives thereof (substitutions, additions of chemical groups, for example, alkyl, alkylene, hydroxylation, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

Bioadhesive polymers of particular interest include bioerodible hydrogels described by H. S. Sawhney, C. P. Pathak and J. A. Hubell in Macromolecules, 1993, 26, 581-587, the teachings of which are incorporated herein, polyhyaluronic acids, casein, gelatin, glutin, polyanhydrides, polyacrylic acid, alginate, chitosan, poly(methyl methacrylates), poly (ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

Other delivery systems can include time-release, delayed release or sustained release delivery systems. Such systems can avoid repeated administrations of the agent, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; silastic systems; peptide based systems; wax coatings; compressed tablets using conventional binders and excipients; partially fused implants; and the like. Specific examples include, but are not limited to: (a) erosional systems in which the platelet reducing agent is contained in a form within a matrix such as those described in U.S. Pat. Nos. 4,452,775, 4,675,189, and 5,736,152 and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

Use of a long-term sustained release implant may be particularly suitable for prophylactic treatment of subjects at risk of developing a recurrent cancer. Long-term release, as used herein, means that the implant is constructed and arranged to delivery therapeutic levels of the active ingredient for at least 30 days, and preferably 60 days. Long-term sustained release implants are well-known to those of ordinary skill in the art and include some of the release systems described above.

A protective agent is administered either before, or substantially concurrently, with the competitive antagonist, so as to protect the host cells from the toxic effects of the latter drug(s). In certain embodiments, there may be particular advantages in beginning administration of the protective agent at a time distinctly prior to administration of the competitive antagonist, wherein prior administration of the protective agent results in a prior increase in the intracellular pools of cellular metabolites such as adenine, adenine nucleotides, and/or methionine in the host cells which may attenuate the toxicity of the adenine/methionine analogs to a significantly greater degree than with simultaneous administration of the drugs, wherein such a prior expansion in the intracellular pool of adenine and/or methionine in the host cells may have one or more of the following effects: inhibition of the transport of the toxic analogs into the host cells, wherein they share a transport carrier in common with their natural homolog, reduction in cellular levels of PRPP and hence in the activity of the enzyme APRT (which is necessary for activation of the adenine analog to its toxic nucleotide form), and an increase in the competitive neutralization of the toxic adenine or methionine analog by the expanded pool of adenine and adenine nucleotides, or methionine.

In certain preferred embodiments of the instant invention, the selective therapy is implemented by a treatment protocol comprising the administration of very high bolus doses of competitive antagonists of adenine or methionine and very high bolus doses of the protective agent, such as MTA or other MTA compound. These high bolus doses may be delivered either orally or parenterally, and they may be administered one or more times a day, and repeated over the course of several days, weeks, or months, according to a dosing schedule guided by previous preclinical studies (e.g. in animal models of the disease being treated) and clinical trials. These high bolus doses of the competitive antagonist may approach, or equal, the maximal rescuable dose or dosing, previously established by the methods described herein. Similarly, the high bolus dose or dosing of the protective MTA compound may approach or equal its maximal tolerable dose or dosing previously established. Applicants have found that three competitive antagonists of adenine, namely, the adenine analogs, 2,6-diaminopurine, 2-fluoroadenine, and 6-methylpurine, all exhibit very rapid and potent killing of human and mouse tumor cells. Applicants have also found that the toxicity, to normal human and mouse cells, of even very high doses of any of these adenine analogs, may be effectively blocked by MTA (or other MTA compounds, such as 5'-deoxyadenosine). As a consequence, Applicants believe that competitive antagonists of adenine that may be particularly effective in the selective therapeutic method, just described, that utilizes high bolus doses or dosing, include (but are not limited to) the adenine analogs, 2,6-diaminopurine, 2-fluoroadenine, and 6-methylpurine. In certain such embodiments, this high bolus dose, selective therapy of mammalian tumors may prove effective after even relatively short-term treatment schedules of perhaps just a few weeks or a few months (in contrast to conventional cancer chemotherapies, where the treatment schedule frequently extends over many months, and in some cases, over many years).

The present invention is described herein, in detail, with reference to a particular presently preferred embodiment, wherein the cellular metabolite is adenine or methionine. However, any difference in metabolism of essential cellular metabolites such as nucleobases, nucleosides, amino acids, or enzyme cofactors, between a target cell and critical cells of the subject, may serve as a basis of a selective therapy according to the methods described herein, wherein such difference in metabolism between a target cell and host cells may be either constitutive (i.e., preexisting) or may be induced by appropriate methods. In certain embodiments, other nucleoside phosphorylases (besides methylthioadenosine phosphorylase), present in mammalian cells, which catalyze the cleavage of nucleosides to nucleobases, such as, for example, purine nucleoside phosphorylase, uridine phosphorylase, and/or thymidine phosphorylase, and the metabolic pathways these enzymes initiate, form the basis of a selective therapy according to the methods described herein, directed against tumors or certain infectious pathogens. In certain embodiments, other enzymatic pathways that might provide such selective therapies, according to the methods described herein, include those initiated by adenosine deaminase, adenosine kinase and/or other nucleoside kinases, or purine and pyrimidine nucleotidases. Mammalian cells have various pathways for amino acid synthesis and interconversions (for example: transamination pathways; the synthesis of arginine in the urea cycle, catalyzed by argininosuccinate lyase; the synthesis of tyrosine from phenylalanine, catalyzed by phenylalanine hydroxylase; the synthesis of asparagine and glutamine), as well as many other pathways required for maintaining amino acids at levels adequate for protein synthesis. Mammalian cells also have many folate interconversion pathways that serve to synthesize and maintain adequate levels of the various folate cofactors required for metabolism. There are also a multitude of intracellular pathways for the synthesis or interconversion of other coenzymes. In certain embodiments, any of the above-mentioned pathways in mammalian cells, leading to nucleobases, nucleosides, amino acids, or enzyme cofactors, form the basis of a selective therapy according to the methods described herein, wherein said pathway is absent, different, or can be downmodulated in a tumor or other target cell.

A non-limiting example of the application of the above-mentioned selective therapeutic methods relates to acute lymphoblastic leukemia. Many acute lymphoblastic leukemias (as well as some other leukemias, malignant melanomas, T-cell lymphomas, multiple myelomas, and ovarian cancers) are known to be deficient in the enzyme asparagine synthase, and these tumors depend on an exogenous supply of asparagine. Treatment of such tumors, by depleting serum asparagine with administration of the asparagine-degrading enzyme L-asparaginase, has met with limited success and prolonged L-asparaginase treatment can be highly toxic. To overcome such toxicity in such neoplasms, in certain embodiments, a toxic competitive antagonist of asparagine along with an agent (e.g., aspartate) to upregulate the asparagine synthase pathway in normal proliferating cells of the subject is administered, so as to protect them from the effects of the toxic asparagine antagonist wherein optionally L-asparaginase is co-administered to deplete serum asparagine, and wherein the serious toxicities of prolonged L-asparaginase exposure are avoided.

In addition to all of the specific agents and pathways exemplified herein, additional metabolic pathways and/or specific agents, useful in the treatment of diseases of humans and other vertebrates, according to the selective therapeutic methods of the instant invention, may be identified based on the guidance provided herein using routine methods known in the art. For instance, a method for developing a selective therapy of a disease associated with a particular target cell in a vertebrate subject may include one or more of the following screening assays and other steps:

(i) Identification of an essential cell metabolite whose levels may be selectively upregulated in host cells, but not in the target cell. Identification of such a selectively-inducible cell metabolite may involve identifying, in the host cells, a metabolic pathway leading to the cellular metabolite which is specifically active in the host cells but not the target cell; that is, in the target cell this pathway is either absent, has lowered activity, or can be selectively inhibited. If a homologous pathway leading to the cellular metabolite exists in the target cell, additional steps of synthesizing and screening potential selective inhibitors of this pathway may be performed.

(ii) Identification of various agents which can upregulate the activity of the identified metabolic pathway in the host cells, This may involve synthesizing substrates, and analogs of substrates for the metabolic pathway and screening these agents for their ability to upregulate the activity of the metabolic pathway in the host cells.

(iii) Screening of identified agents to identify those agents with acceptable toxicity to the subject and those with unacceptable toxicity.

(iv) Synthesis of analogs of the cell metabolite, screening of these analogs for inhibitory activity against the target cell, and testing of any such target cell-inhibitory analogs to determine whether their toxicity to the host cells can be competitively blocked by increasing levels of metabolite.

All screening, identifying and synthesis steps can be carried out using methods well-known in the art, and are well within the reach of one skilled in the art.

The agents described herein may, in some embodiments, be assembled into pharmaceutical kits to facilitate their use in therapeutic applications. A kit may include one or more containers housing the components of the invention and instructions for use. Specifically, such kits may include one or more competitive antagonists of a cell metabolite and/or one or more host protective agents, along with instructions describing the intended therapeutic application and the proper administration of these agents. In certain embodiments agents in a kit may be in a pharmaceutical formulation and dosage suitable for a particular application and for a method of administration of the agents.

The kit may be designed to facilitate use of the methods described herein by physicians, or other health care providers, and can take many forms. Each of the compositions of the kit, where applicable, may be provided in liquid form (e.g., in solution), or in solid form, (e.g., a dry powder). In certain cases, some of the compositions may be constitutable or otherwise processable (e.g., to an active form), for example, by the addition of a suitable solvent or other species (for example, water or a cell culture medium), which may or may not be provided with the kit. As used herein, "instructions" can define a component of instruction and/or promotion, and typically involve written instructions on or associated with packaging of the invention. Instructions also can include any oral or electronic instructions provided in any manner such that a user will clearly recognize that the instructions are to be associated with the kit, for example, audiovisual (e.g., videotape, DVD, etc.), Internet, and/or web-based communications, etc. The written instructions may be in a form prescribed by a governmental agency regulating the manufacture, use or sale of pharmaceuticals or biological products, which instructions can also reflects approval by the agency of manufacture, use or sale for human or animal administration.

The kit may contain any one or more of the components described herein in one or more containers. As an example, in one embodiment, the kit may include instructions for mixing one or more components of the kit and/or isolating and mixing a sample and applying to a subject. The kit may include a container housing agents described herein. The agents may be in the form of a liquid, gel or solid (powder). The agents may be prepared sterilely, packaged in syringe, and shipped refrigerated or frozen. Alternatively they may be housed in a vial or other container for storage. A second container may have other agents such as a protective agent prepared sterilely. Alternatively the kit may include the active agents premixed and shipped in a syringe, vial, tube, or other container. The kit may have one or more or all of the components required to administer the agents to a patient, such as a syringe or iv needle, tubing and bag, or a catheter.

The kit may have a variety of forms, such as a blister pouch, a shrink wrapped pouch, a vacuum sealable pouch, a sealable thermoformed tray, or a similar pouch or tray form, with the accessories loosely packed within the pouch, one or more tubes, containers, a box or a bag.

The kit may be sterilized after the accessories are added, thereby allowing the individual accessories in the container to be otherwise unwrapped. The kits can be sterilized using any appropriate sterilization techniques, such as radiation sterilization, heat sterilization, or other sterilization methods known in the art.

The kit may also contain any other component needed for the intended purpose of the kit. Thus, other components may be a fabric, such as gauze, for applying or removing a disinfecting agent. Other optional components of the kit are disposable gloves, a support for the agents prior to administration.

The kit may include disposable components supplied sterile in disposable packaging. The kit may also include other components, depending on the specific application, for example, containers, cell media, salts, buffers, reagents, syringes, needles, etc.

The following is a list of abbreviations used in the application. ADA: adenosine deaminase, Ade: adenine, AK: adenosine kinase, AMPDA: adenylate deaminase, AMPS: adenylosuccinate, APRT: adenine phosphoribosyltransferase, ASL: adenosylosuccinate lyase, ASS: adenosylosuccinate synthetase, AzaG: 8-azaguanine, CAP: competitive antagonist of metabolite, HCs: host cells (e.g., progenitors of hematopoietic system and gastrointestinal epithelium), 5'-dAdo: 5'-deoxyadenosine, DAP: 2,6-diaminopurine, dcSAM: decarboxylated S-adenosylmethionine, Eth: ethionine, F-Ade: 2-fluoroadenine, FU: 5-fluorouracil, Gln: glutamine, HGPRT: hypoxanthine-guanine phosphoribosyltransferase, Hyc: homocysteine, IMP: inosinate, KMTB: 2-keto-4-methylthiobutyrate, MeP: 6-methylpurine, Met: methionine, MethyleneTHF: 5,10-methylenetetrahydrofolate, MethylTHF: 5-methyltetrahydrofolate, MP: 6-mercaptopurine, MPW: a metabolic pathway in the HCs which produces cellular metabolite, MTA: 5'-deoxy-5'-methylthioadenosine, MTAP: 5'-deoxy-5'-methylthioadenosine phosphorylase, MTR-1-P: 5-methylthioribose-1-phosphate, MTX: methotrexate, ODC: ornithine decarboxylase, P: a cellular metabolite (e.g., a nucleobase, nucleoside, amino acid, or enzyme cofactor), PAT: a target cell (e.g., a tumor or infectious organism) PNP: purine nucleoside phosphorylase, PRA: 5-phosphoribosylamine, PRPP: 5-phosphoribosyl-1-pyrophosphate, PRAG: protective agent (increases the level of cellular metabolite in the HCs), SAH: S-adenosylhomocysteine, SAM: S-adenosylmethionine, SAMDC: S-adenosylmethionine decarboxylase, SeMet: selenomethionine, Ser: serine, SpdS: spermidine synthetase, SpmS: spermine synthetase, TG: 6-thioguanine, and THF: tetrahydrofolate.

The following examples are intended to illustrate certain aspects of certain embodiments of the present invention, but do not exemplify the full scope of the invention.

EXAMPLES

The data presented herein demonstrate that protective agents such as MTA and 5'-dAdo protect a variety of MTAP-positive mammalian cells from very high doses of toxic competitive antagonists of adenine such as the adenine analogs 2,6-diaminopurine (DAP), 6-methylpurine (MeP), 2-fluoroadenine (F-Ade). The data also demonstrate the ability of protective agents such as MTA to protect MTAP-positive mammalian cells from high doses of the toxic methionine analog ethionine. The same treatment method, utilizing MTA and/or 5'-dAdo, will not confer protection on MTAP-negative cells from the toxicity of these adenine and methionine analogs, because these cells lack the ability to generate adenine and methionine from MTA, or adenine from 5'-dAdo. In similar experiments, the data demonstrated that MTA and 5'-dAdo can provide selective protection of MTAP-positive mammalian cells, but not MTAP-negative cells, from competitive antagonists of adenine drawn from the broader class of analog substrates of the other mammalian phosphoribosyltransferases. In particular, it is shown in the Examples that selective protection of MTAP-positive mammalian cells, but not MTAP-negative cells, is achieved using very high doses of the guanine analog 6-thioguanine (TG), which is converted to its corresponding nucleotide by HGPRT, and the pyrimidine analog 5-fluorouracil (FU), which is converted to its nucleotide by OPRT.

The MTAP-positive cells and cells lines in which Applicants have shown the ability of MTA and 5'-dAdo to provide protection from highly toxic doses of adenine and/or methionine competitive antagonists include: human fibroblasts (HF), obtained from newborn foreskin (fibroblasts serve as a model for normal, proliferating human cells); colony-forming hematopoietic cell progenitors (obtained from mouse bone marrow); HT-29 (a human colon carcinoma cell line, used as a model of gastrointestinal epithelial cells); ML-1 (a human myeloblastic leukemia cell line); EJ (a human bladder carcinoma cell line, which is also sometimes denoted T24); and the cell lines T-47D, ZR-75-1, and MDA-MB-468 (all established from human carcinomas of the breast).

The MTAP-negative cell lines in which Applicants have also demonstrated killing by adenine and methionine competitive antagonists include: L1210 (a mouse leukemia); HL-60 (a human promyelocytic leukemia); K-562 (a human chronic myelogenous leukemia); MCF7 and MDA-MB-231 (both human breast carcinomas); A549 (a human lung carcinoma); and PANC-1 (a human pancreatic carcinoma). In these cell lines Applicants have demonstrated the inability of MTA and/or 5'-dAdo to protect against the toxicity of adenine and/or methionine antagonists.

In additional experiments, it was demonstrated that two or more adenine antagonists and/or methionine antagonists can be combined and achieve very potent synergistic killing of tumor cells, and that MTAP-positive mammalian cells can be selectively protected from this potent synergistic toxicity, but MTAP-negative cells are not protected, by co-administering substrates for MTAP such as MTA or 5'-dAdo. In still other experiments, it is shown that the selective killing of MTAP-negative cells by adenine and methionine antagonists can be potentiated, by co-administering inhibitors of de novo purine synthesis such as methotrexate, hadacidin, or alanosine.

Materials and Methods

In general, methods for cell culture and manipulation followed standard procedures as described in many sources, such as the textbook Animal Cell Culture: A Practical Approach, edited by R. I. Freshney, Oxford University Press, 1992.

Cell Culture:

For adherent cell types (e.g., HF, A549, MCF7) cells were plated in 60 mm -diameter plastic tissue culture dishes and incubated at 37° C. in a humidified 5% $CO_2$ atmosphere, in Dulbecco's Modified Eagle's Medium (DME) with 10% fetal bovine serum (FBS). At the start of an experiment, medium was replaced with DME and 10% dialyzed FBS.

For cell types that grow in suspension (e.g., ML-1, HL-60, K-562) medium was RPMI-1640 with 10% FBS (undialyzed).

Penicillin and streptomycin were added to all media.

Media, chemicals, and drugs were obtained from Sigma Chemical Co. (St. Louis, Mo.) or the Drug Synthesis Branch of the National Cancer Institute.

Growth and Viability:

For adherent cell types, cell numbers were determined periodically by releasing cells with trypsin (dead cells that were no longer adherent were removed by two prior rinses of the culture dish) and placing a portion of the resulting cell suspension in a Coulter counter. For cell types that grow in suspension, portions of the culture were counted directly, without trypsin treatment. Coulter counts of cells from each dish were done twice, and almost all experiments were done in duplicate. In the presentation of results, raw data for Coulter counts is given in some cases, while in others, counts have been rounded off to two to three significant figures. (Background Coulter counts—i.e., counts of diluent alone—were insignificant.)

Cell viability of adherent cell types was measured by clonogenic assay as follows: after releasing cells with trypsin and removing a portion of the cell suspension for Coulter counting, the remainder of the cell suspension was plated in serial dilutions in growth medium, without drugs. After a period sufficient for clones to reach a size visible by eye (usually 2 to 3 weeks), clones were stained with crystal violet in a saline/methanol solution. Dishes that had fewer than 100 clones were deemed suitable for counting. From these counts and from the dilution factors, the approximate number of viable cells, in the parent treatment dishes, was calculated. Only 1/16 of the trypsinized cell suspension was removed for the first of the serial dilutions; hence this sampling fraction sets the limit of detection of viable cells. In clonogenic assays, clone size was often variable, especially after treatment with toxic drugs. Moreover, many of the very small clones may have arisen from cells detached during the weeks of incubation. Hence the viable cell numbers (shown in Tables of results) should be regarded as approximate—perhaps with an error of 25%. Cloning efficiency for healthy, growing A549 cells was about 50%; for HF cells, efficiency was quite variable, ranging from 25 to 75% (perhaps because the HF cell stock varied, from experiment to experiment, in passage number).

Often cell numbers, after drug treatment, as measured by Coulter count, were much greater than the number of viable cells, as determined by clonogenic assay. This is to be expected since Coulter counting does not distinguish between adherent dead (or dying) cells and adherent viable cells.

For cells that grow in suspension, the effect of treatments was assessed solely by changes in Coulter count.

In some cases, experimental procedures differed from those described above; if so, these are described with the corresponding Table of results.

Example 1

Figure 6A:
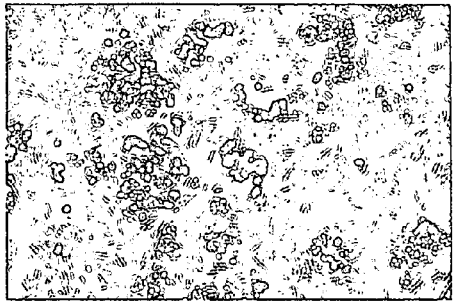
FIGS. 6A and 6B present photographs of experiments examining the efficacy of a selective therapeutic method described herein in two human-tissue coculture experiments. Both experiments demonstrate a very selective killing of MCF7, an MTAP-negative human breast carcinoma cell line, grown in coculture with MTAP-positive human fibroblasts, by the toxic competitive antagonist of adenine, 2,6-diaminopurine (DAP), in the presence of MTA.
Figure 6A:
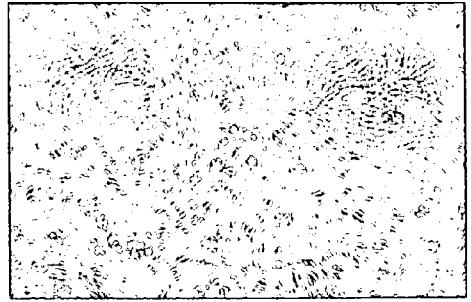
Figure 6A:
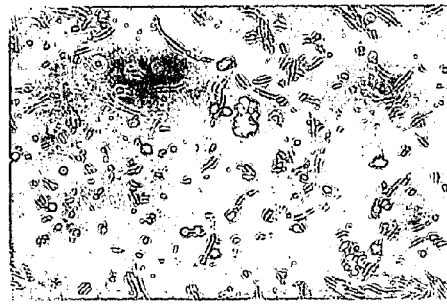
Figure 6A:
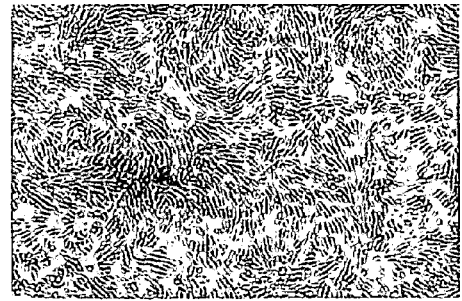
Figure 6B:
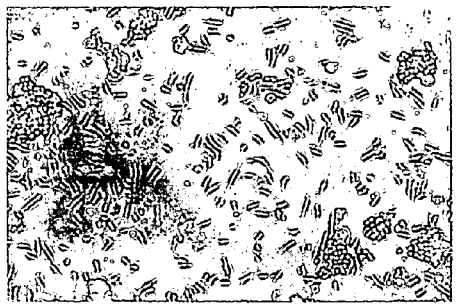
Figure 6B:
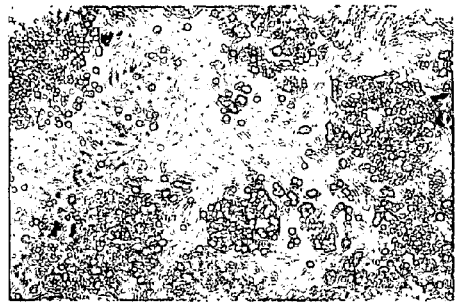
Figure 6B:
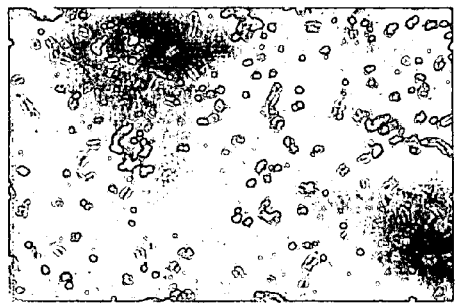
Figure 6B:
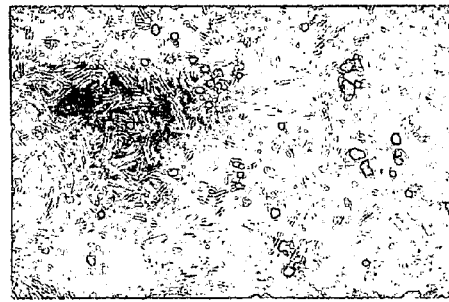

In Coculture, MTA Selectively Protects MTAP(+) HF Cells, but not MTAP(−) MCF7 Cells, from DAP Toxicity FIGS. 6A and 6B present photographs of experiments examining the efficacy of the selective therapeutic method of the invention in two human-tissue coculture experiments. In both experiments human fibroblasts (HF cells), which are MTAP-positive, and MCF7 cells, an MTAP-negative human breast adenocarcinoma cell line, were seeded together into culture dishes, in DME supplemented with 10% dialyzed fetal bovine serum.

In the experiment of FIG. 6A the cell coculture was treated for four days with 100 μM DAP and 25 μM MTA. At the end of this period, some of the culture dishes were fixed, to be photographed. Other dishes were trypsinized and diluted five-fold into fresh (drug-free) medium with adenine added (to stop any further toxic action of DAP) and allowed to grow for two more, or five more, days, before being fixed for photography. A comparison of the photos of the dish fixed immediately after the four days of drug treatment, with the photos of the dishes split 1:5, and then fixed two and five days later, clearly shows that only the fibroblasts grew. In fact, the photo of the dish grown out for five days (after the 1:5 split) shows a confluent sheet of fibroblasts but no MCF7 clonal masses—just a few isolated, and presumably non-viable, MCF7 cells or cell remnants.

In the experiment of FIG. 6B cell cocultures were treated for three days with 200 μM DAP alone or with the addition of 50 μM MTA, or with no drugs at all. As shown in the photo of the dish without any drugs added to the culture medium, both HF and MCF7 grew very well; many large masses of MCF7 cells are visible, with the elongated HF cells interspersed, confluently, between the MCF7 masses. In the photo of the dish with DAP present in the culture medium, little except cellular remnants and debris are visible; it appears that very few, if any, HF or MCF7 cells have survived. The final photo—of a coculture treated with both DAP and MTA—shows a nearly confluent sheet of fibroblasts with a small number of isolated, and presumably non-viable, MCF7 cells or cell remnants.

In coculture, a few days of treatment with 100-200 μM DAP effectively killed both MCF7, an MTAP-negative human breast carcinoma cell line, and HF cells, which are MTAP-positive. With the addition of 25-50 μM MTA, HF cells were selectively protected from DAP toxicity.

Example 2

In Coculture, 5'-dAdo Selectively Protects MTAP(+) Hf Cells, but not MTAP(−) A549-ouaR Cells, from DAP Toxicity HF and A549-ouaR (a ouabain-resistant derivative of the human lung carcinoma cell line A549, isolated by Applicants) cells were cultured together in a medium containing DAP, and with or without 5'-dAdo. After 3 days, cultures were trypsinized and serially diluted into fresh medium for clonogenic assays. Some dishes were treated with 0.1 μM ouabain to kill HF cells and permit easy visualization of surviving A549-ouaR clones. Initial viable cells: HF cells, 11,000; A549-ouaR cells, 40,000.

Results are Shown below:

| DAP (μM) | 5'-Ado (μM) | Viable HF | Viable A549-ouaR* |
|---|---|---|---|
| 125 | 0 | 240 | 0 |
| 125 | 7.5 | 13,200 | 3 |

*See Methods for limit of detection.

In coculture, DAP alone effectively killed both HF and A549-ouaR cells, as expected. With the addition of 5'-dAdo, DAP killed A549-ouaR cells, but HF cells were protected by intracellular adenine produced by the action of MTAP on 5'-dAdo.

Example 3

5'-dAdo and MTA Both Protect MTAP(+) Hf Cells from MEP Toxicity

Cell cultures were treated with MeP, with or without 5'-dAdo or MTA, for 4 days. The cell cultures were then changed to fresh medium, with the addition of 30 μM Ade to inhibit further action of the analog. Two days later cultures were trypsinized and a portion of the suspension was counted. Raw data are shown below.

Initial Coulter counts at start of experiment: 1,157

| MeP (μM) | 5'-dAdo (μM) | MTA (μM) | Coulter counts* |
|---|---|---|---|
| 0 | 0 | 0 | 22,548 |
| 5 | 0 | 0 | 2,885 |
| 5 | 20 | 0 | 25,750 |
| 5 | 0 | 10 | 12,407 |
| 5 | 0 | 20 | 21,038 |
| 10 | 20 | 0 | 21,993 |
| 10 | 0 | 10 | 6,535 |
| 10 | 0 | 20 | 32,078 |

*For total number of cells/dish, multiply by 56.

MeP was strongly toxic to HF cells. Both 5'-dAdo and MTA effectively protected HF cells against MeP toxicity, and permitted substantial proliferation of these cells.

Example 4

Adenine, but not MTA or 5'-dAdo, Protects MTAP(−) A549 Cells from MeP Toxicity

A549 cells were incubated for 4 days with additions shown below, and viable cells measured by clonogenic assay. (Results shown are approximate; see Methods) Cell count in dish at start: 40,000

| MeP (μM) | MTA (μM) | 5'-dAdo (μM) | Ade (μM) | Viable Cells* |
|---|---|---|---|---|
| 0 | 0 | 0 | 0 | ~1,000,000 |
| 10 | 0 | 0 | 0 | 0 |
| 10 | 20 | 0 | 0 | 0 |
| 10 | 0 | 20 | 0 | 200** |
| 10 | 0 | 0 | 20 | ~1,000,000 |

*See Methods for limit of detection.
**After 5 days of incubation, assay of cultures with 10 μM MeP and 20 μM 5'-dAdo showed no colonies.

10 μM MeP was highly toxic to A549 cells, as measured by clonogenic assay. This toxicity was blocked by adenine, but not by MTA or 5'-Ado, because A549 cells lack MTAP and hence can not produce adenine from these MTAP-substrates.

Example 5

5'-dAdo protects MTAP(+) HF cells from F-Ade toxicity, as determined both by cell counts and clonogenic assay.

A. F-Ade was added to cultures of HF cells, with varying amounts of 5'-dAdo. After 3 days, cell numbers were counted.

Initial cell count: 1,100

After three days:

| F-Ade (μM) | 5'-dAdo (μM) | Coulter counts* |
|---|---|---|
| 0.3 | 0 | 1478 |
| 0.3 | 7.5 | 4945 |
| 0.3 | 15 | 6725 |
| 0.3 | 30 | 6872 |
| 0.6 | 0 | 976 |
| 0.6 | 7.5 | 2045 |
| 0.6 | 15 | 2482 |
| 0.6 | 30 | 4575 |
| 0 | 60 | 8150 |

*For total number of cells/dish, multiply by 56.

B. F-Ade was added to cultures of MTAP(+) HF cells, with or without 5'-dAdo, for 3 days. Cultures were then trypsinized and serially diluted for clonogenic assay.

Initial number of viable cells per dish: 45,000

Viable cells after 3 days shown below:

| F-Ade (μM) | 5'-dAdo (μM) | Viable Cells |
|---|---|---|
| 2 | 0 | 0* |
| 2 | 30 | 92,000 |

*See Methods for limit of detection

Increasing concentrations of F-Ade caused increasing inhibition of HF cell growth. As the concentration of 5'-dAdo increases, so does protection from toxicity of F-Ade. At 2 μM F-Ade, after 3 days, no HF cells survive; 30 μM 5'-dAdo effectively blocks this toxicity.

Example 6

Adenine, but not MTA or 5'-dAdo, Protects MTAP(−) A549 Tumor Cells from F-Ade Toxicity MTAP(−) A549 lung tumor cell cultures were treated with F-Ade, with or without MTA, 5'-dAdo, or adenine (Ade), for three days. Coulter counts of cells, and viable cells as determined by clonogenic assay, are shown below:

Initial cell number: 10,340*

| F-Ade (μM) | MTA (μM) | 5'-dAdo (μM) | Ade (μM) | Coulter counts* | Viable Cells** |
|---|---|---|---|---|---|
| 1 | 0 | 0 | 0 | 7,980 | 64 |
| 1 | 40 | 0 | 0 | 10,160 | 496 |
| 1 | 0 | 40 | 0 | 8,440 | 288 |
| 1 | 0 | 0 | 40 | 39,600 | 44,000*** |
| 2 | 0 | 0 | 0 | 7,890 | 0 |
| 2 | 40 | 0 | 0 | 10,640 | 0 |
| 2 | 0 | 40 | 0 | 5,480 | 0 |
| 2 | 0 | 0 | 40 | 33,880 | 99,000*** |

*To obtain total number of cells per dish multiply Coulter counts by 4.
**See Methods for limit of detection.
***Viable cell calculation was based on a small number of clones per dish in final dilution of clonogenic assay; hence difference between 44,000 and 99,000 may be due to random error.

1 to 2 μM F-Ade is highly toxic to A549 tumor cells, as measured by clonogenic assay. This toxicity was blocked by adenine, but not by MTA or 5'-dAdo, because A549 cells cannot generate adenine from these MTAP substrates.

Example 7

Adenine, but not 5'-dAdo, Protects MTAP(−) A549 Tumor Cells from DAP Toxicity

A549 cell cultures were treated with DAP, with or without 5'-dAdo or adenine, for three days. After trypsinization, one-fourth of the cell suspension was counted, and raw data is shown below, with duplicate counts for each sample. The cell suspension was also serially diluted for clonogenic assay.

Counts at start of experiment: Dish one: 36,480; 39,160; Dish two: 52,680; 51,360.

Initial viable cells by clonogenic assay: 180,000.

| DAP (μM) | 5'-dAdo (μM) | Ade (μM) | Coulter counts* | Viable Cells** |
|---|---|---|---|---|
| 0 | 0 | 0 | 280,120; 306,360 | 590,000*** |
| 100 | 0 | 0 | 17,320; 17,480 | 0 |
| 100 | 30 | 0 | 16,800; 17,000 | 0 |
| 100 | 0 | 30 | 190,520; 191,760 | 550,000 |

*For total cells per dish, multiply by 4.
**See Methods for limit of detection.
***Viable cells in control dish (no drugs added) after three days of incubation, estimated from Coulter count above and cloning efficiency of A549 (~50%).

100 μM DAP is highly toxic to MTAP(−) A549 cells. 5'-dAdo did not block this toxicity, though adenine did. In other experiments, MTA, as with 5'-dAdo, did not block DAP toxicity in A549 cells.

Example 8

5'-dAdo, MTA, and Adenine all Protect MTAP(+) HF Cells from DAP Toxicity, and from Combined DAP/MTX Toxicity Cultures of human fibroblasts were treated with DAP, 5'-dAdo, MTA, adenine, or MTX. Thymidine (15 μM) was added to all cultures.

Initial count was: 1807

Counts, as raw data, after 3 days of incubation, are shown below:

| MTX (μM) | DAP (μM) | 5'-dAdo (μM) | MTA (μM) | Ade (μM) | Coulter Counts* |
|---|---|---|---|---|---|
| 0 | 0 | 0 | 0 | 0 | 13,819 |
| 0 | 100 | 0 | 0 | 0 | 2,483 |
| 0 | 100 | 15 | 0 | 0 | 11,090 |

-continued

| MTX (μM) | DAP (μM) | 5'-dAdo (μM) | MTA (μM) | Ade (μM) | Coulter Counts* |
|---|---|---|---|---|---|
| 0 | 100 | 0 | 15 | 0 | 12,006 |
| 0 | 100 | 0 | 0 | 15 | 11,441 |
| 10 | 0 | 0 | 0 | 0 | 3,455 |
| 10 | 100 | 0 | 0 | 0 | 1,481 |
| 10 | 100 | 15 | 0 | 0 | 12,628 |
| 10 | 100 | 0 | 15 | 0 | 11,510 |
| 10 | 100 | 0 | 0 | 15 | 11,609 |

*For total cells/dish, multiply figures by 56.

MTAP(+) HF cells were inhibited by DAP, but this toxicity was blocked by 5'-dAdo, MTA, or adenine. Inhibition was stronger when both MTX and DAP were present. Protection from DAP occurred equally well, with or without MTX.

Example 9

Both MTX and Alanosine Potentiate Killing of MTAP(−) A549 Cells by DAP

Cell cultures were treated with MTX or alanosine for one day. DAP was then added and 3 days later, cells were trypsinized and serially diluted for clonogenic assay. Results are shown below:
Initial viable cells: 146,000

| DAP (μM) | MTX (μM) | Alanosine (μM) | Viable Cells |
|---|---|---|---|
| 0 | 1 | 0 | 89,000 |
| 0 | 0 | 3 | 118,000 |
| 40 | 0 | 0 | 59,000 |
| 40 | 1 | 0 | 9,000 |
| 40 | 0 | 3 | 5,900 |

Inhibitors of de novo purine biosynthesis, such as MTX and alanosine, strongly potentiated killing of A549 cells by DAP Example 10

MTA Protects MTAP(+) HF Cells from L-Ethionine Toxicity

HF cells were plated, and after they had adhered to the substrate, medium was changed to methionine-free medium, with 10% dialyzed serum.
Initial Coulter count: 73,000*; viable cells: 88,000
After 3 days in methionine-free medium, with or without L-ethionine (Eth) or MTA:

| Eth (μM) | MTA (μM) | Coulter counts* (duplicate dishes) | Viable Cells** |
|---|---|---|---|
| 0 | 0 | 112,280; 124,200 | 72,000 |
| 40 | 0 | 28,400; 36,440 | 1,600 |
| 0 | 15 | 132,880; 150,560 | not done |
| 40 | 15 | 156,720; 150,800 | 176,000 |

*To convert Coulter counts to cells/dish, multiply figures above by 4.
**By clonogenic assay. Note that cell number by Coulter count is about three times greater than viable cells by clonogenic assay; as indicated in Methods, cloning efficiency for healthy HF cells is variable, and, from one experiment to the next, may range from 25 to 75%.

40 μM L-ethionine was very toxic to HF cells in methionine-free medium. 15 μM MTA effectively blocked this toxicity.

Example 11

MTA does not Protect MTAP(−) A549 Tumor Cells from L-Ethionine Toxicity

A549 cells were plated, and after they had adhered to the substrate, medium was changed to methionine-free medium with 10% dialyzed serum. L-ethionine (Eth) and MTA were added, and after 4 days, cell cultures were trypsinized and serially diluted for clonogenic assay.
Initial number of viable cells: 160,000*

| Eth (μM) | MTA (μM) | Viable Cells** |
|---|---|---|
| 0 | 0 | 37,000 |
| 40 | 0 | 24,000 |
| 40 | 30 | 21,000 |
| 80 | 0 | 5,000 |
| 80 | 30 | 5,300 |

*Initial viable cells estimated from Coulter count and cloning efficiency of A549 (~50%).
**In this experiment, data were obtained from dishes with relatively small numbers of clones, ranging from 8 to 39. Hence sampling error is presumably higher than in other experiments.

Because A549 lacks MTAP, it cannot generate methionine from MTA. Hence MTA did not block L-ethionine toxicity in A549.

Example 12

5'-dAdo Protects MTAP(+) HT29 Cells from FU Toxicity

5'-dAdo was added to cultures of MTAP(+) HT29 colon carcinoma cells for one day. 5-fluorouracil (FU) was then added and 4 days later cultures were trypsinized, thoroughly dispersed into mostly single cells by vigorous pipetting, and counted.
Initial Coulter count at time of addition of FU: 46,000

| FU (μM) | 5'-dAdo (μM) | Coulter counts* |
|---|---|---|
| 3 | 0 | 65,300 |
| 10 | 0 | 36,600 |
| 30 | 0 | 25,500 |
| 3 | 60 | 107,000 |
| 10 | 60 | 82,200 |
| 30 | 60 | 42,500 |
| 0 | 0 | 129,000 |

*For total number of cells/dish, multiply Coulter counts by 4.

In MTAP(+) HT29 cells, FU toxicity was blocked by 5'-dAdo

Example 13

5'-dAdo does not Protect MTAP(−) HL-60 Cells from FU Toxicity, Although Adenine does HL-60 cells were grown in RPMI 1640 with 10% FBS. 5'-dAdo, adenine, or neither were added, and after 3 hours, 5-fluorouracil (FU) was added to selected dishes. Six days later, cell numbers were assessed in a Coulter counter.

Initial cell number/ml: 8,160

| 5'-dAdo (μM) | Ade (μM) | FU (μM) | Coulter counts/ml |
|---|---|---|---|
| 0 | 0 | 0 | 1,178,000 |
| 0 | 0 | 10 | 125,200 |
| 60 | 0 | 10 | 149,000 |
| 0 | 60 | 10 | 640,000 |
| 0 | 0 | 30 | 62,400 |
| 60 | 0 | 30 | 70,000 |
| 0 | 60 | 30 | 130,200 |

HL-60 cells are not protected from FU toxicity by 5'-dAdo because, lacking MTAP, they cannot produce adenine from 5'-dAdo.

Example 14

5'-dAdo Protects MTAP(+) ML-1 Cells from Toxicity of FU, TG, and DAP

ML-1 cells were incubated in RPMI 1640 with 10% FBS with 5'-dAdo (60 μM) for 6 hours. 5-fluorouracil (FU), 6-thioguanine (TG), or 2,6-diaminopurine (DAP) were then added, and after 2 additional days, 0.5 ml was taken for Coulter counts. Initial Coulter count/ml: 308,000

| FU (μM) | TG (μM) | DAP (μM) | Increase in cell number/ml* | |
|---|---|---|---|---|
| | | | No 5'-dAdo | 60 μM 5'-dAdo |
| 0 | 0 | 0 | 1,160,000 | 918,000 |
| 3 | 0 | 0 | 436,000 | 884,000 |
| 0 | 20 | 0 | 114,000 | 812,000 |
| 0 | 0 | 50 | 220,000 | 862,000 |
| 3 | 20 | 0 | 96,000 | 578,000 |
| 0 | 20 | 50 | 118,000 | 774,000 |
| 3 | 0 | 50 | 164,000 | 786,000 |
| 3 | 20 | 50 | 88,000 | 588,000 |

*Counts were averaged from data of duplicate dishes, with each dish also counted in duplicate. Numbers are given to 2-3 significant figures.

FU, TG, and DAP all inhibited growth of MTAP(+) ML-1 cells. 5'-dAdo effectively protected against growth inhibition caused by these three drugs, both individually and in combination.

Example 15

5'-dAdo Protects MTAP(+) HF Cells from TG and DAP Toxicity

Human fibroblasts in culture were treated with 6-thioguanine (TG), 2,6-diaminopurine (DAP), or 5'-dAdo for 3 days. After trypsinization, cell numbers were counted.
Initial cell number: 296,000

| TG (μM) | DAP (μM) | 5'-dAdo (μM) | Increase in cells/dish* |
|---|---|---|---|
| 0 | 0 | 0 | 1,104,000 |
| 40 | 0 | 0 | 72,000 |
| 0 | 50 | 0 | 254,000 |
| 40 | 50 | 0 | 0 |
| 40 | 0 | 60 | 568,000 |
| 0 | 50 | 60 | 912,000 |
| 40 | 50 | 60 | 680,000 |

*Numbers were rounded to 2-3 significant figures.

TG and DAP inhibited HF cell growth. 5'-dAdo blocked inhibition by TG and by DAP. 5'-dAdo also protected HF cells from the combined, strongly synergistic, toxicity of TG and DAP.

Example 16

TG and DAP Produce Strong Synergistic Killing of MTAP(−) A549 Cells

A549 cultures were treated with 6-thioguanine (TG) or 2,6-diaminopurine (DAP), or both, for 3 days.
Initial viable cells: 275,000
After 3 days:

| TG (μM) | DAP (μM) | Viable Cells |
|---|---|---|
| 40 | 0 | 200,000 |
| 0 | 50 | 12,000 |
| 40 | 50 | 540 |

When added together, TG and DAP produced a strong synergistic killing of A549 cells.

Example 17

Figure 7:
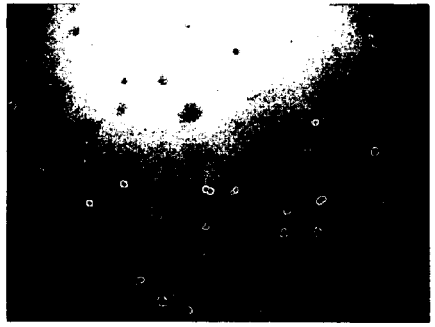
FIG. 7 presents photographs of an experiment examining the ability of 5'-deoxyadenosine (5'-dAdo) to protect MTAP-positive mouse hematopoietic cell progenitors from the toxic competitive antagonist of adenine, 6-methylpurine (MeP).
Figure 7:
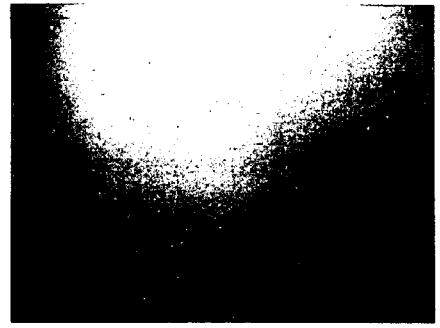
Figure 7:
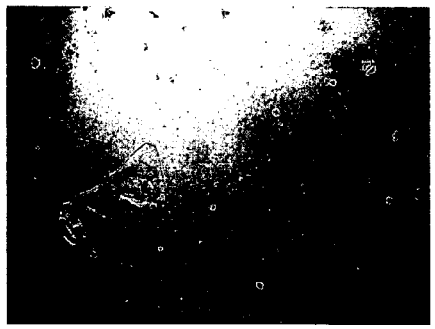
Figure 7:
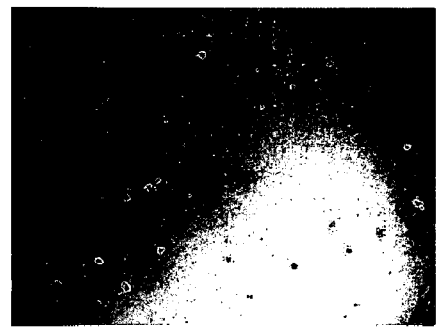
Figure 7:
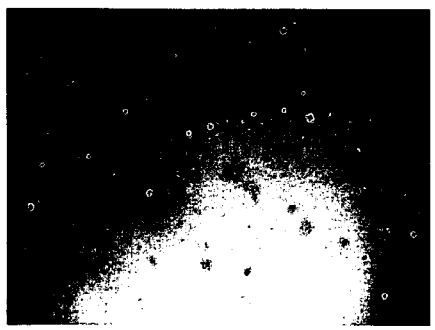
Figure 7:

5'-dAdo Protects MTAP(+) Hematopoietic Cell Progenitors, Obtained from Mouse Bone Marrow, from MeP Toxicity Method: The procedure for assay of colony-forming cells from mouse bone marrow was similar to methods described in the literature (see e.g., B. A. Teicher et al, Cancer Research, 47:513-518, 1987). In brief, cells were flushed from the femurs of Swiss mice, counted, and seeded into six-well tissue culture plates with supplemented McCoy's 5A medium, 15% FBS, 10 to 20% L929-cell conditioned medium as a source of colony-stimulating activity (L929 is MTAP-negative), 0.3% agar, and penicillin/streptomycin (op. cit. B. A. Teicher et al). Cells were seeded at two different densities: 50,000 and 250,000 cells per well. Control wells contained either no drugs, or adenine at 15 or 30 μM, or 5'-deoxyadenosine (5'-dAdo) at 15, 30, or 45 μM. Treatment wells contained 6-methylpurine (MeP) at 5 or 15 μM, 5'-deoxyadenosine (5'-dAdo) at 15 or 30 μM, and adenine at 15 or 30 μM, in various combinations. After eight days of incubation at 37° C. in a humidified 5% $CO_2$ atmosphere, wells were fixed by the addition of 1 ml of 5% glutaraldehyde. Photographs were taken of a randomly selected portion of each well, as viewed (at fixed magnification) through a Nikon inverted microscope equipped with a camera.
Results:
For the wells seeded at 250,000 cells/well: In the control wells, with no drugs added, approximately 40-50 colonies were observed (in each field of view). With either 5 or 15 μM MeP present, no colonies were seen, indicating complete killing of colony-forming progenitors by this drug. When either adenine or 5'-dAdo was also present at 15 or 30 μM, numerous colonies grew out, about as many as in the control dishes. A portion of these results is presented in the six photographs of FIG. 7.
For the wells seeded at 50,000 cells: The various drug treatments produced effects very similar to those obtained with the more heavily-seeded wells. The only difference was that colony-formation in each of these wells was reduced to approximately one-fifth that of the corresponding, denselyseeded well. MeP at doses of 5 and 15 µM was highly toxic to colony-forming murine hematopoietic progenitors. 5'-dAdo, at doses as low as 15 µM, effectively blocked this toxicity.

REFERENCES

Numbered references cited herein are listed on the following pages and are incorporated herein by reference.

1. Merlo A., Gabrielson E., Mabry M., Vollmer R., Baylin S. B., Sidransky D., *Homozygous deletion on chromosome 9p and loss of heterozygosity on 9q, 6p, and 6q in primary human small cell lung cancer*, Cancer Res., 54: 2322-2326, 1994.

2. Olopade O. I., Buchhagen D. L., Malik K., Sherman J., Nobori T., Bader S., Nau M. M., Gazdar A. F., Minna J. D., Diaz M. O., *Homozygous loss of the interferon genes defines the critical region on 9p that is deleted in lung cancers*, Cancer Res. 53: 2410-2415, 1993.

3. Schimd M., Malicki D., Nobori T., Rosenbach M. D., Campbell K., Carson D. A., Carrera C. J., *Homozygous deletions of methylthioadenosine phosphorylase (MTAP) are more frequent than p16INK4a (CDKN2) homozygous deletions in primary non-small cell lung cancers (NSCLC)*, Oncogene, 17: 2669-2675, 1998.

4. Barker F. G., Chen P., Furman F., Aldape K. D., Edwards M. S., Israel M. A., *p16 deletion and mutation analysis in human brain tumors*, J. Neurooncol., 31: 17-23, 1997.

5. Nobori T., Karras J. G., Della Ragione F., Waltz T. A., Chen P. P., Carson D. A., *Absence of methylthioadenosine phosphorylase in human gliomas*, Cancer Res., 51(12): 3193-3197, 1991.

6. Zhang H., Chen Z-H., Savarese T. M., *Codeletion of the genes for p16INK4a, methylthioadenosine phosphorylase, interferon-1, interferon-β1, and other 9p21 markers in human malignant cell lines*, Cancer Genet. Cytogenet., 86: 22-28, 1996.

7. Chen Z-H., Zhang H., Savarese T. M., *Gene deletion chemoselectivity: codeletion of the genes for p16INK4a, methylthioadenosine phosphorylase, and the-and β-interferons in human pancreatic cell carcinoma cell lines and its implications for chemotherapy*, Cancer Res., 56: 1083-1090, 1996.

8. Caldas C., Hahn S. A., da Costa L. T., Redston, Schutte M., Seymour A. B., Weinstein C. L., Hruban R. H., Yeo C. J., Kern S. E., *Frequent somatic mutations and homozygous deletions of the p16 (MTS1) gene in pancreatic adenocarcinoma*, Nature Genetics, 8: 27-32, 1994.

9. Stadler W. M., Olopade O. I., *The 9p21 region in bladder cancer cell lines: large homozygous deletion inactivate the CDKN2, CDKN2B and MTAP genes*, Urol. Res., 24: 239-244, 1996.

10. Stadler W. M., Steinberg G., Yang X., Hagos F., Turner C., Olopade O. I., *Alterations of the 9p21 and 9q33 chromosomal bands in clinical bladder cancer specimens by fluorescence in situ hybridization*, Clin. Cancer Res., 7: 1676-1682, 2001.

11. Cowan J. M., Halaban R., Francke U., *Cytogenetic analysis of melanocytes from premalignant nevi and melanomas*, J. Natl. Cancer Inst., 80: 1159-1164, 1988.

12. Batova A., Diccianni M. B., Omura-Minamisawa M., Yu J., Carrera C. J., Bridgeman L. J., Kung F. H., Pullen J., Amylon M. D., Yu A. L., *Use of alanosine as a methylthioadenosine phosphorylase-selective therapy for T-cell acute lymphoblastic leukemia in vitro*, Cancer Res., 59: 1492-1497, 1999.

13. Hori Y., Hori K., Yamada Y., Carrera C. J., Tomonaga M., Kamihira S., Carson D. A., Nobori T., *The methylthioadenosine phosphorylase gene is frequently co-deleted with the p16INK4a gene in acute type adult T-cell leukemia*, Int. J. Cancer, 75: 51-56, 1998.

14. Batova A., Diccianni M. B., Nobori T., Vu T., Yu J., Bridgeman L., Yu A. L., *Frequent deletion in the methylthioadenosine phosphorylase gene in T-cell acute lymphoblastic leukemia: Strategies for enzyme-targeted therapy*, Blood, 88(8): 3083-3090, 1996.

15. M'soka T. J., Nishioka J., Taga A., Kato K., Kawasaki H., Yamada Y., Yu A., Komada Y., Nobori T., *Detection of methylthioadenosine phosphorylase (MTAP) and p16 gene deletion in T cell acute lymphoblastic leukemia by real-time quantitative PCR assay*, Leukemia, 14(5): 935-40, 2000.

16. Dreyling M. H., Roulston D., Bohlander S. K., Vardinan J., Olopade O. I., *Codeletion of CDKN2 and MTAP genes in a subset of non-Hodgkin's Lymphoma may be associated with histologic transformation from low-grade to diffuse large-cell lymphoma*, Genes Chromosomes Cancer, 22: 72-78, 1998.

17. Wong Y. F., Chung T. K., Cheung T. H., Nobori T., Chang A. M., *MTAP gene deletion in endometrial cancer*, Gynecol. Obstet. Investig., 45: 272-276, 1998.

18. Bello M. J., Rey J. A., *Chromosome aberrations in metastatic ovarian cancer: relationship with abnormalities in primary tumors*, Int. J. Cancer, 45: 50-54, 1990.

19. Della Ragione F., Russo G. L., Oliva A., Mastropietro S., Mancini A., Borrelli A., Casero R. A., Iolascon A., Zappia V., *5'Deoxy-5'-methylthioadenosine phosphorylase and p16INK4 deficiency in multiple tumor cell lines*, Oncogene 10: 827-833, 1995.

20. Smaaland R., Schanche J. S., Kvinnsland S., Hostmark J., Ueland P. M., *Methylthioadenosine phosphorylase in human breast cancer*, Breast Cancer Res. & Treatment. 9(1): 53-9, 1987.

21. van der Riet P., Nawroz H., Hruban R. H., Corio R., Tokino K., Koch W., Sidransky D., *Frequent loss of chromosome 9p21-22 early in head and neck cancer progression*, Cancer Res., 54: 1156-1158, 1994.

22. Fitchen J. H., Riscoe M. K., Dana B. W., Lawrence H. J., Ferro A. J., *Methylthioadenosine phosphorylase deficiency in human leukemias and solid tumors*, Cancer Res. 46: 5409-5412, Oct. 1986.

23. Verdorfer I, Hobisch A., Hittmair A., Duba H-C., Bartsch G., Utermann G., Erdel M., *Cytogenetic characterization of 22 human renal cell tumors in relation to a histopathological classification*, Cancer Genet Cytogenet 111: 61-70, 1999.

24. Illei P. B., Rusch V., Ladanyi M., *Detection of homozygous deletion of CDKN2A and methylthioadenosine phosphorylase (MTAP) by FISH in 95 cases of pleural mesothelioma*, U.S. and Canadian Academy of Pathology 91st Annual Meeting Feb. 23-Mar. 1, 2002.

25. Jagasia A. A., Block J. A., Qureshi A., Diaz M. O., Nobori T., Gitelis S., Iyer A. P., *Chromosome 9 related aberrations and deletions of the CDKN2 and MTS2 putative tumor suppressor genes in human chondrosarcoma*, Cancer Lett., 105: 91-103, 1996.

26. Jagasia A. A., Block J. A., Diaz M. O., Nobori T., Gitelis S., Inerot S. E., Iyer A. P., *Partial deletions of the CDKN2 and MTS2 putative tumor suppressor genes in a myxoid chondrosarcoma*, Cancer Lett., 105: 77-90, 1996.

27. Li W. W., Cole P., Martin D. S., Banerjee D., and Bertino J. R., *Selective cell killing induced by L-alanosine is dependent on methylthioadenosine phosphorylase status in human soft-tissue sarcoma cells and is enhanced by 6-methylmercaptopurine riboside*, in press, 2002.

28. Garci-Castellano J. M., Villanueva A., Healey J. H., Sowers R., Cordon-Cardo C., Huvos A., Bertino J. R., Meyers P., Gorlick R., *Methylthioadenosine phosphorylase gene deletions are common in osteosarcoma*, Clin. Cancer Res. 8(3): 782-287, Mar. 2002.

29. Riscoe M. K., Ferro A. J., Fitchen J. H., *Methionine recycling as a target for antiprotozoal drug development*, Parasitology Today 5(10):330-333, 1989.

30. Sufrin J. R., Bacchi C. J., Porter C. W., Nathan H, Spiess A. J., Yarlett N., U.S. Pat. No. 5,180,714.

31. Della Ragione F., Porcelli M., Carteni-Farina M., Zappia V., *Escherichia coli S-adenosylhomocysteine/5'methylthioadenosine nucleosidase*, Biochem. J. 232:335-341, 1985.

32. Cornell K. A., Swartz W. E., Barry R. D, Riscoe M. K., *Characterization of recombinant Escherichia coli S-adenosylhomocysteine/5'methylthioadenosine nucleosidase: analysis of enzymatic activity and substrate specificity*, Biochem. Biophys. Res. Comm. 228:724-732, 1996.

33. Sharma V., Tekwani B. L., Saxena J. K., Gupta S., Katiyar J. C., Chatterjee R. K., Ghatak S., Shukla O. P., *Polyamine metabolism in some helminth parasites*, Experimental Parasitology 72:15-23, 1991.

34. Tekwani B. L., Mishra M., Chatterjee R. K., *Polyamine uptake by a rodent filariid, Acanthocheilonema viteae (Nematoda: Filarioidea)*, Int. J. Biochem. and Cell Biol. 27:851-855, 1995.

All references recited herein are incorporated by reference.

The invention having been fully described, modifications and extensions thereof may become obvious to those of ordinary skill in the art. All such modifications and extensions are within the scope of the invention.

What is claimed is:

1. A method for treating a subject having a cancer or infectious disease comprising:
    (a) administering to the subject a competitive antagonist of adenine or methionine in an amount effective to treat the cancer or infectious disease, wherein the competitive antagonist of adenine is a substrate for a phosphoribosyltransferase selected from the group consisting of adenine phosphoribosyltransferase (APRT), hypoxanthine-guanine phosphoribosyltransferase (HGPRT), orotate phosphoribosyltransferase (OPRT), quinolinate phosphoribosyltransferase (QPRT), nicotinate phosphoribosyltransferase (NAPRT) and nicotinamide phosphoribosyltransferase (NAMPRT); and
    (b) administering to the subject a protective agent in an amount effective to increase the level of adenine or methionine in a population of host cells of the subject, thereby reducing the toxicity of the competitive antagonist to the subject, wherein the subject has a methylthioadenosine phosphorylase (MTAP) negative target cell and wherein the protective agent is a MTAP substrate.

2. The method of claim 1 wherein step (b) is initiated prior to step (a).

3. The method of claim 1 wherein step (a) and step (b) are carried out at least in part concurrently.

4. The method of claim 1 wherein the competitive antagonist is a structural analog of adenine or methionine.

5. The method of claim 1 wherein the protective agent is selected from the group consisting of 5'-deoxy-5'-methylthioadenosine, 5'-deoxyadenosine, 2',5'-dideoxyadenosine, 2'-deoxy-5'-deoxy-5'-methylthioadenosine, 5'-deoxy-5'-chloroadenosine, 5'-deoxy-5'-fluoroadenosine, 5'-deoxy-5'methyloxyadenosine, 5'-deoxy-5'-methylselenoadenosine, 5'-deoxy-5'-ethylthioadenosine, 9-β-D-erythrofuranosyladenine, 5'-deoxy-5'-methylthio-2-methyladenosine, and 5'-deoxy-5'-methylthio-1-deazaadenosine.

6. The method of claim 1 wherein the protective agent is a methionine salvage pathway substrate.

7. The method of claim 1 wherein the competitive antagonist is an analog of adenine, wherein the analog of adenine is selected from the group consisting of 2,6-diaminopurine, 6-methylpurine, 2-fluoroadenine, 8-azaadenine, 2-azaadenine, 4-aminopyrazolo[3,4-d]pyrimidine, 8-aza-2,6-diaminopurine, 1-methyladenine, 7-deaza-8-azaadenine, 6-methylaminopurine, 6-N-hydroxylaminopurine, 6-hydrazinopurine, 7-methyladenine, 8-methyladenine, 8-hydroxyadenine, and the 2-methyl-, 2-chloro-, 2-iodo-, 2-hydroxy, 2-methylthio, and 2-mercapto- derivatives of adenine.

8. The method of claim 1 wherein the competitive antagonist is a structural analog of methionine.

9. The method of claim 8 wherein the analog of methionine is selected from the group consisting of ethionine, selenomethionine, methoxinine, selenoethionine, α-methylmethionine, and trifluoromethionine.

10. A method for selective protection of a MTAP positive host cell exposed to a competitive antagonist of adenine or methionine, comprising contacting the host cell with a protective agent in an amount effective to increase the level of adenine or methionine in the host cell thereby reducing the toxicity of the competitive antagonist to the host cell, wherein the competitive antagonist of adenine is a substrate for a phosphoribosyltransferase selected from the group consisting of adenine phosphoribosyltransferase (APRT), hypoxanthine-guanine phosphoribosyltransferase (HGPRT), orotate phosphoribosyltransferase (OPRT), quinolinate phosphoribosyltransferase (QPRT), nicotinate phosphoribosyltransferase (NAPRT) and nicotinamide phosphoribosyltransferase (NAMPRT), and wherein the protective agent is a MTAP substrate.

* * * * *